United States Patent
Yan et al.

(10) Patent No.: US 10,752,693 B2
(45) Date of Patent: Aug. 25, 2020

(54) METHODS FOR TREATING OBESITY AND NONALCOHOLIC FATTY LIVER DISEASE OR NONALCOHOLIC STEATOHEPATITIS USING GLUCAGON RECEPTOR ANTAGONISTIC ANTIBODIES

(71) Applicant: REMD Biotherapeutics, Inc., Camarillo, CA (US)

(72) Inventors: Hai Yan, Thousand Oaks, CA (US); Jim Shi, Thousand Oaks, CA (US); Jeong Oh, Newbury Park, CA (US)

(73) Assignee: REMD Biotherapeutics, Inc., Camarillo, CA (US)

( * ) Notice: Subject to any disclaimer, the term of this patent is extended or adjusted under 35 U.S.C. 154(b) by 16 days.

(21) Appl. No.: 15/563,162

(22) PCT Filed: Mar. 31, 2016

(86) PCT No.: PCT/US2016/025336
§ 371 (c)(1),
(2) Date: Sep. 29, 2017

(87) PCT Pub. No.: WO2016/161154
PCT Pub. Date: Oct. 6, 2016

(65) Prior Publication Data
US 2018/0079820 A1 Mar. 22, 2018

Related U.S. Application Data

(60) Provisional application No. 62/142,257, filed on Apr. 2, 2015.

(51) Int. Cl.
*C07K 16/28* (2006.01)
*A61K 39/395* (2006.01)
*A61K 45/06* (2006.01)
*A61K 39/00* (2006.01)

(52) U.S. Cl.
CPC ...... *C07K 16/2869* (2013.01); *A61K 39/3955* (2013.01); *A61K 45/06* (2013.01); *A61K 2039/505* (2013.01); *A61K 2039/545* (2013.01); *C07K 2317/21* (2013.01); *C07K 2317/56* (2013.01); *C07K 2317/76* (2013.01); *C07K 2317/92* (2013.01)

(58) Field of Classification Search
CPC .............................. A61K 39/3955; A61K 45/06
See application file for complete search history.

(56) References Cited

U.S. PATENT DOCUMENTS

| 8,501,686 B2 | 8/2013 | Oral et al. |
| 2011/0223160 A1 | 9/2011 | Yan et al. |
| 2014/0335091 A1 | 11/2014 | Forgie et al. |

OTHER PUBLICATIONS

Boza et al., Obesity Surg. 15: 1148-1153, 2005.*
Browning et al. (Hepatology, 40: 1387-1395, 2004.*
Chamow and Ashkenazi, TIBTECH 14: 52-60, 1996.*
Rudikoff et al., Proc. Natl. Acad. Sci. 79: 1979-1983, 1982.*
Dhir and Cusi, "Glucagon like peptide-1 receptor agonists for the management of obesity and non-alcoholic fatty liver disease: a novel therapeutic option", J Investig Med, 66:7-10, Sep. 15, 2017.
Ding et al, "Exendin-4, a Glucagon-Like Protein-1 (GLP-1) Receptor Agonist, Reverses Hepatic Steatosis in ob/ob Mice", Hepatology, 43(1):173-181, Jan. 2006.
Lee et al, "Hyperglycemia in rodent models of type 2 diabetes requires insulin-resistant alpha cells", PNAS, 111(36):13217-13222, Sep. 9, 2014.
Liu et al., "GLP-1 receptor agonists: effects on the progression of non-alcoholic fatty liver disease", Diabetes Metab Res Rev., 31:329-335, Sep. 14, 2014.
PCT Written Opinion of the International Search Authority, dated Aug. 22, 2016.
Wortham et al., "The Transition From Fatty Liver to Nash Associates with SAMe depletion in db/db Mice Fed a Methionine Choline-Deficient Diet", Dig Dis Sci., 53(10):2761-2774, Oct. 2008.

* cited by examiner

*Primary Examiner* — Gyan Chandra
(74) *Attorney, Agent, or Firm* — Craig A Crandall, APC; Craig A Crandall

(57) ABSTRACT

The present disclosure relates to methods for treating or preventing obesity and/or nonalcoholic fatty liver diseases (NAFLDs) and/or nonalcoholic steatohepatitis (NASH) using a glucagon receptor blocking agent. In various embodiments, the present disclosure relates to methods for treating or preventing NAFLD/NASH using antigen binding and antagonizing proteins, e.g., fully human antibodies, that specifically bind to and antagonize the function of the human glucagon receptor.

8 Claims, 16 Drawing Sheets
Specification includes a Sequence Listing.

Note: **p<0.01 Compared With Vehicle Group.

SEQUENCE LISTING

<160> NUMBER OF SEQ ID NOS: 52

<210> SEQ ID NO 1
<211> LENGTH: 477
<212> TYPE: PRT
<213> ORGANISM: Homo sapiens

<400> SEQUENCE: 1

Met Pro Pro Cys Gln Pro Gln Arg Pro Leu Leu Leu Leu Leu Leu
1               5                   10                  15

Leu Ala Cys Gln Pro Gln Val Pro Ser Ala Gln Val Met Asp Phe Leu
            20                  25                  30

Phe Glu Lys Trp Lys Leu Tyr Gly Asp Gln Cys His His Asn Leu Ser
        35                  40                  45

Leu Leu Pro Pro Pro Thr Glu Leu Val Cys Asn Arg Thr Phe Asp Lys
    50                  55                  60

Tyr Ser Cys Trp Pro Asp Thr Pro Ala Asn Thr Thr Ala Asn Ile Ser
65                  70                  75                  80

Cys Pro Trp Tyr Leu Pro Trp His His Lys Val Gln His Arg Phe Val
                85                  90                  95

Phe Lys Arg Cys Gly Pro Asp Gly Gln Trp Val Arg Gly Pro Arg Gly
            100                 105                 110

Gln Pro Trp Arg Asp Ala Ser Gln Cys Gln Met Asp Gly Glu Glu Ile
        115                 120                 125

Glu Val Gln Lys Glu Val Ala Lys Met Tyr Ser Ser Phe Gln Val Met
    130                 135                 140

Tyr Thr Val Gly Tyr Ser Leu Ser Leu Gly Ala Leu Leu Leu Ala Leu
145                 150                 155                 160

Ala Ile Leu Gly Gly Leu Ser Lys Leu His Cys Thr Arg Asn Ala Ile
                165                 170                 175

His Ala Asn Leu Phe Ala Ser Phe Val Leu Lys Ala Ser Ser Val Leu
            180                 185                 190

Val Ile Asp Gly Leu Leu Arg Thr Arg Tyr Ser Gln Lys Ile Gly Asp
        195                 200                 205

Asp Leu Ser Val Ser Thr Trp Leu Ser Asp Gly Ala Val Ala Gly Cys
    210                 215                 220

Arg Val Ala Ala Val Phe Met Gln Tyr Gly Ile Val Ala Asn Tyr Cys
225                 230                 235                 240

Trp Leu Leu Val Glu Gly Leu Tyr Leu His Asn Leu Leu Gly Leu Ala
            245                 250                 255

Thr Leu Pro Glu Arg Ser Phe Phe Ser Leu Tyr Leu Gly Ile Gly Trp
        260                 265                 270

Gly Ala Pro Met Leu Phe Val Val Pro Trp Ala Val Val Lys Cys Leu
    275                 280                 285

Phe Glu Asn Val Gln Cys Trp Thr Ser Asn Asp Asn Met Gly Phe Trp
290                 295                 300

Trp Ile Leu Arg Phe Pro Val Phe Leu Ala Ile Leu Ile Asn Phe Phe
305                 310                 315                 320

Ile Phe Val Arg Ile Val Gln Leu Leu Val Ala Lys Leu Arg Ala Arg
                325                 330                 335

Gln Met His His Thr Asp Tyr Lys Phe Arg Leu Ala Lys Ser Thr Leu
            340                 345                 350

Thr Leu Ile Pro Leu Leu Gly Val His Glu Val Val Phe Ala Phe Val
        355                 360                 365

Thr Asp Glu His Ala Gln Gly Thr Leu Arg Ser Ala Lys Leu Phe Phe
370                 375                 380

Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg Arg Trp His
                405                 410                 415

Arg Trp Arg Leu Gly Lys Val Leu Trp Glu Glu Arg Asn Thr Ser Asn
            420                 425                 430

His Arg Ala Ser Ser Ser Pro Gly His Gly Pro Pro Ser Lys Glu Leu
        435                 440                 445

Gln Phe Gly Arg Gly Gly Gly Ser Gln Asp Ser Ser Ala Glu Thr Pro
450                 455                 460

Leu Ala Gly Gly Leu Pro Arg Leu Ala Glu Ser Pro Phe
465                 470                 475

<210> SEQ ID NO 2
<211> LENGTH: 128
<212> TYPE: PRT
<213> ORGANISM: Homo sapiens

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Trp Tyr Asp Gly Ser Asn Lys Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Glu Lys Asp His Tyr Asp Ile Leu Thr Gly Tyr Asn Tyr Tyr
            100                 105                 110

Tyr Gly Leu Asp Val Trp Gly Gln Gly Thr Thr Val Thr Val Ser Ser
        115                 120                 125

```
<210> SEQ ID NO 3
<211> LENGTH: 107
<212> TYPE: PRT
<213> ORGANISM: Homo sapiens

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Val Gln Pro
65                  70                  75                  80

Glu Asp Phe Val Thr Tyr Tyr Cys Leu Gln His Asn Ser Asn Pro Leu
            85                  90                  95

Thr Phe Gly Gly Gly Thr Lys Val Glu Ile Lys
            100                 105

<210> SEQ ID NO 4
<211> LENGTH: 128
<212> TYPE: PRT
<213> ORGANISM: Homo sapiens

<400> SEQUENCE: 4

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Trp Tyr Asp Gly Ser Asn Lys Asp Tyr Val Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Glu Lys Asp His Tyr Asp Ile Leu Thr Gly Tyr Asn Tyr Tyr
            100                 105                 110

Tyr Gly Leu Asp Val Trp Gly Gln Gly Thr Thr Val Thr Val Ser Ser
        115                 120                 125

<210> SEQ ID NO 5
<211> LENGTH: 107
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45
```

```
Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Val Thr Tyr Tyr Cys Leu Gln His Asn Ser Asn Pro Leu
                85                  90                  95

Thr Phe Gly Gly Gly Thr Lys Val Glu Ile Lys
                100                 105
```

<210> SEQ ID NO 6
<211> LENGTH: 128
<212> TYPE: PRT
<213> ORGANISM: Homo sapiens

<400> SEQUENCE: 6

```
Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
                35                  40                  45

Ala Val Met Trp Tyr Asp Gly Ser Asn Lys Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Glu Lys Asp His Tyr Asp Ile Leu Thr Gly Tyr Asn Tyr Tyr
                100                 105                 110

Tyr Gly Leu Asp Val Trp Gly Gln Gly Thr Thr Val Thr Val Ser Ser
                115                 120                 125
```

<210> SEQ ID NO 7
<211> LENGTH: 107
<212> TYPE: PRT
<213> ORGANISM: Homo sapiens

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
                35                  40                  45

Tyr Ala Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Val Gln Pro
65                  70                  75                  80

Glu Asp Phe Val Thr Tyr Tyr Cys Leu Gln His Asn Ser Asn Pro Leu
                85                  90                  95

Thr Phe Gly Gly Gly Thr Lys Val Glu Ile Lys
                100                 105
```

<210> SEQ ID NO 8
<211> LENGTH: 471
<212> TYPE: PRT
<213> ORGANISM: Artificial Sequence
<220> FEATURE:

<223> OTHER INFORMATION: heavy chain of a chimeric antibody that binds GCGR

<400> SEQUENCE: 8

| Met | Glu | Phe | Gly | Leu | Ser | Trp | Val | Phe | Leu | Val | Ala | Leu | Leu | Arg | Gly |
|---|---|---|---|---|---|---|---|---|---|---|---|---|---|---|---|
| 1 | | | | 5 | | | | | 10 | | | | | 15 | |

| Val | Gln | Cys | Gln | Val | Gln | Leu | Val | Glu | Ser | Gly | Gly | Gly | Val | Val | Gln |
| | | 20 | | | | | 25 | | | | | 30 | | | |

| Pro | Gly | Arg | Ser | Leu | Arg | Leu | Ser | Cys | Ala | Ala | Ser | Gly | Phe | Thr | Phe |
| | | 35 | | | | | 40 | | | | | 45 | | | |

| Ser | Ser | Tyr | Gly | Met | His | Trp | Val | Arg | Gln | Ala | Pro | Gly | Lys | Gly | Leu |
| | 50 | | | | | 55 | | | | | 60 | | | | |

| Glu | Trp | Val | Ala | Val | Met | Trp | Tyr | Asp | Gly | Ser | Asn | Lys | Asp | Tyr | Val |
| 65 | | | | | 70 | | | | | 75 | | | | | 80 |

| Asp | Ser | Val | Lys | Gly | Arg | Phe | Thr | Ile | Ser | Arg | Asp | Asn | Ser | Lys | Asn |
| | | | | 85 | | | | | 90 | | | | | 95 | |

| Thr | Leu | Tyr | Leu | Gln | Met | Asn | Arg | Leu | Arg | Ala | Glu | Asp | Thr | Ala | Val |
| | | | 100 | | | | | 105 | | | | | 110 | | |

| Tyr | Tyr | Cys | Ala | Arg | Glu | Lys | Asp | His | Tyr | Asp | Ile | Leu | Thr | Gly | Tyr |
| | | 115 | | | | | 120 | | | | | 125 | | | |

| Asn | Tyr | Tyr | Gly | Leu | Asp | Val | Trp | Gly | Gln | Gly | Thr | Thr | Val | Thr |
| 130 | | | | | 135 | | | | | 140 | | | | | |

| Val | Ser | Ser | Ala | Lys | Thr | Thr | Pro | Pro | Ser | Val | Tyr | Pro | Leu | Ala | Pro |
| 145 | | | | | 150 | | | | | 155 | | | | | 160 |

| Gly | Ser | Ala | Ala | Gln | Thr | Asn | Ser | Met | Val | Thr | Leu | Gly | Cys | Leu | Val |
| | | | | 165 | | | | | 170 | | | | | 175 | |

| Lys | Gly | Tyr | Phe | Pro | Glu | Pro | Val | Thr | Val | Thr | Trp | Asn | Ser | Gly | Ser |
| | | | 180 | | | | | 185 | | | | | 190 | | |

| Leu | Ser | Ser | Gly | Val | His | Thr | Phe | Pro | Ala | Val | Leu | Gln | Ser | Asp | Leu |
| | | 195 | | | | | 200 | | | | | 205 | | | |

| Tyr | Thr | Leu | Ser | Ser | Ser | Val | Thr | Val | Pro | Ser | Ser | Thr | Trp | Pro | Ser |
| | 210 | | | | | 215 | | | | | 220 | | | | |

| Glu | Thr | Val | Thr | Cys | Asn | Val | Ala | His | Pro | Ala | Ser | Ser | Thr | Lys | Val |
| 225 | | | | | 230 | | | | | 235 | | | | | 240 |

| Asp | Lys | Lys | Ile | Val | Pro | Arg | Asp | Cys | Gly | Cys | Lys | Pro | Cys | Ile | Cys |
| | | | | 245 | | | | | 250 | | | | | 255 | |

| Thr | Val | Pro | Glu | Val | Ser | Ser | Val | Phe | Ile | Phe | Pro | Pro | Lys | Pro | Lys |
| | | | 260 | | | | | 265 | | | | | 270 | | |

| Asp | Val | Leu | Thr | Ile | Thr | Leu | Thr | Pro | Lys | Val | Thr | Cys | Val | Val | Val |
| | | 275 | | | | | 280 | | | | | 285 | | | |

| Asp | Ile | Ser | Lys | Asp | Asp | Pro | Glu | Val | Gln | Phe | Ser | Trp | Phe | Val | Asp |
| | 290 | | | | | 295 | | | | | 300 | | | | |

| Asp | Val | Glu | Val | His | Thr | Ala | Gln | Thr | Gln | Pro | Arg | Glu | Glu | Gln | Phe |
| 305 | | | | | 310 | | | | | 315 | | | | | 320 |

| Asn | Ser | Thr | Phe | Arg | Ser | Val | Ser | Glu | Leu | Pro | Ile | Met | His | Gln | Asp |
| | | | | 325 | | | | | 330 | | | | | 335 | |

| Trp | Leu | Asn | Gly | Lys | Glu | Phe | Lys | Cys | Arg | Val | Asn | Ser | Ala | Ala | Phe |
| | | | 340 | | | | | 345 | | | | | 350 | | |

| Pro | Ala | Pro | Ile | Glu | Lys | Thr | Ile | Ser | Lys | Thr | Lys | Gly | Arg | Pro | Lys |
| | | 355 | | | | | 360 | | | | | 365 | | | |

| Ala | Pro | Gln | Val | Tyr | Thr | Ile | Pro | Pro | Pro | Lys | Glu | Gln | Met | Ala | Lys |
| | 370 | | | | | 375 | | | | | 380 | | | | |

| Asp | Lys | Val | Ser | Leu | Thr | Cys | Met | Ile | Thr | Asp | Phe | Phe | Pro | Glu | Asp |
| 385 | | | | | 390 | | | | | 395 | | | | | 400 |

Ile Thr Val Glu Trp Gln Trp Asn Gly Gln Pro Ala Glu Asn Tyr Lys
            405                 410                 415

Asn Thr Gln Pro Ile Met Asp Thr Asp Gly Ser Tyr Phe Val Tyr Ser
        420                 425                 430

Lys Leu Asn Val Gln Lys Ser Asn Trp Glu Ala Gly Asn Thr Phe Thr
    435                 440                 445

Cys Ser Val Leu His Glu Gly Leu His Asn His Thr Glu Lys Ser
450                 455                 460

Leu Ser His Ser Pro Gly Lys
465                 470

<210> SEQ ID NO 9
<211> LENGTH: 236
<212> TYPE: PRT
<213> ORGANISM: Artificial Sequence
<220> FEATURE:
<223> OTHER INFORMATION: light chain of a chimeric antibody that binds
      GCGR

<400> SEQUENCE: 9

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Glu Ser Gly Val
65                  70                  75                  80

Pro Ser Arg Phe Ser Gly Ser Gly Ser Gly Thr Glu Phe Thr Leu Thr
                85                  90                  95

Ile Ser Ser Val Gln Pro Glu Asp Phe Val Thr Tyr Tyr Cys Leu Gln
            100                 105                 110

His Asn Ser Asn Pro Leu Thr Phe Gly Gly Gly Thr Lys Val Glu Ile
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235

<210> SEQ ID NO 10
<211> LENGTH: 125
<212> TYPE: PRT
<213> ORGANISM: Homo sapiens

<400> SEQUENCE: 10

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
            35                  40                  45

Ala Val Ile Leu Ser Asp Gly Arg Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Asp Tyr Glu Ile Leu Thr Gly Tyr Gly Tyr Tyr Gly Met
            100                 105                 110

Asp Val Trp Gly Gln Gly Thr Thr Val Thr Val Ser Ser
            115                 120                 125

<210> SEQ ID NO 11
<211> LENGTH: 125
<212> TYPE: PRT
<213> ORGANISM: Homo sapiens

<400> SEQUENCE: 11

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Leu Asn Asp Gly Arg Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Asp Tyr Glu Ile Leu Thr Gly Tyr Gly Tyr Tyr Gly Met
            100                 105                 110

Asp Val Trp Gly Gln Gly Thr Thr Val Thr Val Ser Ser
            115                 120                 125

<210> SEQ ID NO 12
<211> LENGTH: 129
<212> TYPE: PRT
<213> ORGANISM: Homo sapiens

<400> SEQUENCE: 12

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Gly Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Tyr Asp Tyr Ala
            50                  55                  60

Gly Ser Val Lys Ser Arg Ile Asn Ile Asn Pro Asp Thr Ser Lys Asn
65                  70                  75                  80

Gln Phe Ser Leu Gln Val Asn Ser Val Thr Pro Glu Asp Thr Ala Val
                85                  90                  95

Tyr Tyr Cys Thr Arg Asp Arg Ser Ser Gly Trp Asn Glu Gly Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 13
<211> LENGTH: 128
<212> TYPE: PRT
<213> ORGANISM: Homo sapiens

<400> SEQUENCE: 13

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Pro Gly Lys Gly Leu Glu Trp Val
        35                  40                  45

Ala Val Leu Ser Ser Asp Gly Asn Asn Lys Tyr Cys Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Glu Glu Val Tyr Tyr Asp Ile Leu Thr Gly Tyr Tyr Asp Tyr
            100                 105                 110

Tyr Gly Met Asp Val Trp Gly Gln Gly Thr Thr Val Thr Val Ser Ser
        115                 120                 125

<210> SEQ ID NO 14
<211> LENGTH: 126
<212> TYPE: PRT
<213> ORGANISM: Homo sapiens

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30

Phe Trp Thr Trp Ile Arg Gln Phe Pro Gly Lys Gly Leu Glu Trp Ile
        35                  40                  45

Gly Tyr Ile Phe Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Tyr Tyr Asp Ile Leu Thr Gly Glu Asp Tyr Ser Tyr Gly
            100                 105                 110

Met Asp Val Trp Gly Gln Gly Thr Thr Val Thr Val Ser Ser
        115                 120                 125

<210> SEQ ID NO 15
<211> LENGTH: 129

-continued

<212> TYPE: PRT
<213> ORGANISM: Homo sapiens

<400> SEQUENCE: 15

Gln Val Gln Leu Gln Gln Ser Gly Pro Gly Leu Val Lys Pro Ser Gln
1               5                   10                  15

Ile Leu Ser Leu Thr Cys Ala Ile Ser Gly Asp Arg Val Ser Ser Asn
            20                  25                  30

Gly Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Tyr Asp Tyr Ala
    50                  55                  60

Gly Ser Val Lys Ser Arg Ile Asn Ile Asn Pro Asp Thr Ser Lys Asn
65                  70                  75                  80

Gln Phe Ser Leu Gln Val Asn Ser Val Thr Pro Glu Asp Thr Ala Val
                85                  90                  95

Tyr Tyr Cys Ala Arg Asp Arg Ser Ser Gly Trp Asn Glu Gly Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 16
<211> LENGTH: 126
<212> TYPE: PRT
<213> ORGANISM: Homo sapiens

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Thr Tyr
            20                  25                  30

Phe Trp Thr Trp Ile Arg Gln Phe Pro Gly Glu Gly Leu Glu Trp Ile
        35                  40                  45

Gly Tyr Ile Phe Tyr Ser Gly Asn Thr Asn Tyr Asn Pro Ser Leu Thr
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Tyr Tyr Asp Ile Leu Thr Gly Glu Asp Tyr Ser Tyr Gly
            100                 105                 110

Ile Asp Val Trp Gly Gln Gly Thr Thr Val Thr Val Ser Ser
        115                 120                 125

<210> SEQ ID NO 17
<211> LENGTH: 125
<212> TYPE: PRT
<213> ORGANISM: Homo sapiens

<400> SEQUENCE: 17

Gln Val Gln Leu Val Glu Ser Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Gly Met His Trp Val Arg Gln Ala Pro Gly Lys Gly Leu Glu Trp Val
        35                  40                  45

```
Ala Val Ile Ser Asn Asp Gly Ser Asn Lys Tyr Tyr Ala Asp Phe Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Asp Tyr Asp Ile Leu Thr Gly Asn Gly Val Tyr Gly Met
            100                 105                 110

Asp Val Trp Gly Gln Gly Thr Thr Val Thr Val Ser Ser
            115                 120                 125
```

<210> SEQ ID NO 18
<211> LENGTH: 122
<212> TYPE: PRT
<213> ORGANISM: Homo sapiens

<400> SEQUENCE: 18

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Thr Met Asn Trp Val Arg Gln Ala Pro Gly Lys Gly Leu Glu Trp Val
         35                  40                  45

Ser Tyr Ile Ser Gly Ser Ser Leu Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu His Met Asn Ser Leu Arg Asp Glu Asp Thr Ala Val Tyr Tyr Cys
                 85                  90                  95

Ala Arg Ala Arg Tyr Asn Trp Asn Asp Tyr Tyr Gly Met Asp Val Trp
            100                 105                 110

Gly Gln Gly Thr Thr Val Thr Val Ser Ser
            115                 120
```

<210> SEQ ID NO 19
<211> LENGTH: 116
<212> TYPE: PRT
<213> ORGANISM: Homo sapiens

<400> SEQUENCE: 19

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ala Phe Ser Ser Tyr
             20                  25                  30

Gly Ile His Trp Val Arg Gln Ala Pro Gly Lys Gly Leu Glu Trp Val
         35                  40                  45

Ala Gly Ile Trp Tyr Asp Gly Ser Asn Lys Tyr Tyr Ala Asp Ser Val
     50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Phe Asp Ala Phe Asp Ile Trp Gly Gln Gly Thr Met Val
            100                 105                 110

Thr Val Ser Ser
            115
```

```
<210> SEQ ID NO 20
<211> LENGTH: 128
<212> TYPE: PRT
<213> ORGANISM: Homo sapiens

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Thr Met Asn Trp Val Arg Gln Ala Pro Gly Lys Gly Leu Glu Trp Val
        35                  40                  45

Ser Tyr Ile Ser Ser Ser Ser Leu Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Ser Asp Tyr Tyr Gly Ser Gly Ser Tyr Tyr Lys Gly Asn Tyr
                100                 105                 110

Tyr Gly Met Asp Val Trp Gly Gln Gly Thr Thr Val Thr Val Ser Ser
            115                 120                 125

<210> SEQ ID NO 21
<211> LENGTH: 128
<212> TYPE: PRT
<213> ORGANISM: Homo sapiens

<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Thr Ile Ile Trp Ser Asp Gly Ile Asn Lys Tyr Tyr Ala Asp Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Arg Glu Arg Gly Leu Tyr Asp Ile Leu Thr Gly Tyr Tyr Asp Tyr
                100                 105                 110

Tyr Gly Ile Asp Val Trp Gly Gln Gly Thr Thr Val Thr Val Ser Ser
            115                 120                 125

<210> SEQ ID NO 22
<211> LENGTH: 128
<212> TYPE: PRT
<213> ORGANISM: Homo sapiens

<400> SEQUENCE: 22

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

```
Gly Met His Trp Val Arg Gln Ala Pro Gly Lys Gly Leu Glu Trp Val
         35                  40                  45

Thr Ile Ile Trp Ser Asp Gly Ile Asn Lys Tyr Tyr Ala Asp Ser Val
     50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                 85                  90                  95

Ala Arg Glu Arg Gly Leu Tyr Asp Ile Leu Thr Gly Tyr Tyr Asp Tyr
                100                 105                 110

Tyr Gly Ile Asp Val Trp Gly Gln Gly Thr Thr Val Thr Val Ser Ser
        115                 120                 125
```

<210> SEQ ID NO 23
<211> LENGTH: 116
<212> TYPE: PRT
<213> ORGANISM: Homo sapiens

<400> SEQUENCE: 23

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Ile Thr Phe Arg Ser Tyr
                 20                  25                  30

Ser Met Asn Trp Val Arg Gln Ala Pro Gly Lys Gly Leu Glu Trp Val
             35                  40                  45

Ser Ala Ile Ser Ser Ser Ser Tyr Ile Tyr Tyr Ala Asp Ser Val
         50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                 85                  90                  95

Ala Arg Gly Arg Tyr Gly Met Asp Val Trp Gly Gln Gly Thr Thr Val
                100                 105                 110

Thr Val Ser Ser
        115
```

<210> SEQ ID NO 24
<211> LENGTH: 125
<212> TYPE: PRT
<213> ORGANISM: Homo sapiens

<400> SEQUENCE: 24

```
Gln Val Gln Leu Val Glu Ser Gly Gly Gly Val Val Gln Pro Gly Arg
1               5                   10                  15

Ser Leu Arg Leu Ser Cys Ala Ala Ser Gly Ser Thr Phe Arg Ser Tyr
                 20                  25                  30

Asp Met His Trp Val Arg Gln Ala Pro Gly Lys Gly Leu Glu Trp Val
             35                  40                  45

Ala Val Ile Ser Tyr Asp Gly Ser Asn Lys Tyr Tyr Gly Asp Ser Val
         50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Asp Gln Tyr Asp Ile Leu Thr Gly Tyr Ser Ser Asp Ala Phe
                100                 105                 110
```

Asp Ile Trp Gly Gln Gly Thr Met Val Thr Val Ser Ser
            115                 120                 125

<210> SEQ ID NO 25
<211> LENGTH: 127
<212> TYPE: PRT
<213> ORGANISM: Homo sapiens

<400> SEQUENCE: 25

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser His Lys Tyr Tyr Glu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Gly Val Tyr Tyr Cys
                85                  90                  95

Ala Arg Val Gly Tyr Gly Ser Gly Trp Tyr Glu Tyr Tyr His Tyr
            100                 105                 110

Gly Met Asp Val Trp Gly Gln Gly Thr Thr Val Thr Val Ser Ser
            115                 120                 125

<210> SEQ ID NO 26
<211> LENGTH: 128
<212> TYPE: PRT
<213> ORGANISM: Homo sapiens

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Trp Tyr Asp Gly Ser Asn Lys Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Glu Lys Asp His Tyr Asp Ile Leu Thr Gly Tyr Asn Tyr Tyr
            100                 105                 110

Tyr Gly Leu Asp Val Trp Gly Gln Gly Thr Thr Val Thr Val Ser Ser
            115                 120                 125

<210> SEQ ID NO 27
<211> LENGTH: 128
<212> TYPE: PRT
<213> ORGANISM: Homo sapiens

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr

```
                    20                  25                  30
Gly Met His Trp Val Arg Gln Ala Pro Gly Lys Gly Leu Glu Trp Val
            35                  40                  45
Ala Val Met Trp Tyr Asp Gly Ser Asn Lys Asp Tyr Val Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Arg Leu Arg Ala Glu Asp Thr Ala Val Tyr Tyr Cys
                85                  90                  95
Ala Arg Glu Lys Asp His Tyr Asp Ile Leu Thr Gly Tyr Asn Tyr Tyr
            100                 105                 110
Tyr Gly Leu Asp Val Trp Gly Gln Gly Thr Thr Val Thr Val Ser Ser
            115                 120                 125

<210> SEQ ID NO 28
<211> LENGTH: 116
<212> TYPE: PRT
<213> ORGANISM: Homo sapiens

<400> SEQUENCE: 28

Gln Val Gln Leu Val Glu Ser Gly Gly Gly Val Val Gln Pro Gly Arg
1               5                   10                  15
Ser Leu Arg Leu Ser Cys Ala Ala Ser Gly Ile Thr Phe Ser Ser Tyr
            20                  25                  30
Gly Met His Trp Val Arg Gln Ala Pro Gly Lys Gly Leu Glu Trp Val
        35                  40                  45
Ala Ser Ile Trp Tyr Asp Gly Ser Asn Lys Tyr Tyr Val Asp Ser Val
    50                  55                  60
Lys Gly Arg Phe Thr Ile Phe Arg Asp Asn Ser Lys Lys Thr Leu Tyr
65                  70                  75                  80
Leu Gln Met Asn Arg Leu Arg Ala Glu Asp Thr Ala Val Tyr Tyr Cys
                85                  90                  95
Ala Arg Leu Gly Gly Gly Phe Asp Tyr Trp Gly Gln Gly Thr Leu Val
            100                 105                 110
Thr Val Ser Ser
            115

<210> SEQ ID NO 29
<211> LENGTH: 108
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Asn Tyr
            20                  25                  30
Leu Ala Trp Phe Gln Lys Pro Gly Lys Ala Pro Lys Ser Leu Ile
        35                  40                  45
Tyr Val Val Ser Ser Leu Gln Ser Gly Val Pro Ser Arg Phe Ser Gly
    50                  55                  60
Ser Gly Ser Gly Thr Asp Phe Thr Leu Thr Ile Asn Asn Leu Gln Pro
65                  70                  75                  80
Glu Asp Phe Ala Thr Tyr Tyr Cys Gln Gln Tyr Asn His Tyr Pro Leu
                85                  90                  95
Thr Phe Gly Gly Gly Thr Arg Val Glu Ile Lys Arg
```

<210> SEQ ID NO 30
<211> LENGTH: 108
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Gln Arg Pro Gly Lys Ala Pro Lys Ser Leu Ile
        35                  40                  45

Tyr Val Val Ser Ser Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Phe Cys Gln Gln Tyr Asn His Tyr Pro Leu
                85                  90                  95

Thr Phe Gly Gly Gly Thr Lys Val Glu Ile Lys Arg
            100                 105

<210> SEQ ID NO 31
<211> LENGTH: 108
<212> TYPE: PRT
<213> ORGANISM: Homo sapiens

<400> SEQUENCE: 31

Asp Ile Gln Met Thr Gln Phe Pro Ser Ser Leu Ser Ala Ser Ile Gly
1               5                   10                  15

Asp Arg Val Thr Ile Thr Cys Gln Ala Ser Gln Asp Ile Ser Asn Phe
            20                  25                  30

Leu Asn Trp Phe Gln Gln Lys Pro Gly Lys Ala Pro Lys Leu Leu Ile
        35                  40                  45

Tyr Asp Ala Ser Asp Leu Glu Thr Gly Val Pro Ser Arg Phe Ser Gly
    50                  55                  60

Ser Gly Ala Gly Thr Asp Phe Thr Phe Thr Ile Ser Ser Leu Gln Pro
65                  70                  75                  80

Glu Asp Ile Ala Thr Tyr Phe Cys Gln Gln Tyr Asp Asp Leu Pro Leu
                85                  90                  95

Thr Phe Gly Gly Gly Thr Arg Val Asp Ile Lys Arg
            100                 105

<210> SEQ ID NO 32
<211> LENGTH: 108
<212> TYPE: PRT
<213> ORGANISM: Homo sapiens

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

```
Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Asn Pro Leu
                85                  90                  95

Thr Phe Gly Gly Gly Thr Lys Val Glu Ile Lys Arg
            100                 105
```

<210> SEQ ID NO 33
<211> LENGTH: 109
<212> TYPE: PRT
<213> ORGANISM: Homo sapiens

<400> SEQUENCE: 33

```
Gln Asn Val Leu Thr Gln Ser Pro Gly Thr Leu Ser Leu Ser Pro Gly
1               5                   10                  15

Glu Arg Val Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Phe Gly Val Ser Ser Arg Ala Thr Gly Ile Pro Asp Arg Phe Ser
50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Phe Thr Phe Gly Pro Gly Thr Lys Val Asp Ile Lys Arg
            100                 105
```

<210> SEQ ID NO 34
<211> LENGTH: 108
<212> TYPE: PRT
<213> ORGANISM: Homo sapiens

<400> SEQUENCE: 34

```
Asp Ile Gln Met Thr Gln Phe Pro Ser Ser Leu Ser Ala Ser Ile Gly
1               5                   10                  15

Asp Arg Val Thr Ile Thr Cys Gln Ala Ser Gln Asp Ile Ser Asn Phe
                20                  25                  30

Leu Asn Trp Phe Gln Gln Lys Pro Gly Lys Ala Pro Lys Leu Leu Ile
            35                  40                  45

Tyr Asp Ala Ser Asp Leu Glu Thr Gly Val Pro Ser Arg Phe Ser Gly
        50                  55                  60

Ser Gly Ala Gly Thr Asp Phe Thr Phe Thr Ile Ser Ser Leu Gln Pro
65                  70                  75                  80

Glu Asp Val Ala Thr Tyr Phe Cys Gln Gln Tyr Asp Asn Leu Pro Leu
                85                  90                  95

Thr Phe Gly Gly Gly Thr Lys Val Asp Ile Lys Arg
            100                 105
```

<210> SEQ ID NO 35
<211> LENGTH: 109
<212> TYPE: PRT
<213> ORGANISM: Homo sapiens

<400> SEQUENCE: 35

```
Glu Asn Val Leu Thr Gln Ser Pro Gly Thr Leu Ser Leu Ser Pro Gly
1               5                   10                  15
```

-continued

```
Glu Arg Ala Thr Leu Ser Cys Arg Ala Ser Gln Ser Val Ser Ser
                20                  25                  30
Tyr Leu Ala Trp Tyr Gln Gln Lys Pro Gly Gln Ala Pro Arg Leu Leu
            35                  40                  45
Ile Phe Gly Val Ser Ser Arg Ala Thr Gly Ile Pro Asp Arg Phe Ser
 50                  55                  60
Gly Ser Gly Ser Gly Thr Asp Phe Ser Leu Thr Ile Ser Arg Leu Glu
 65                  70                  75                  80
Pro Glu Asp Phe Ala Val Tyr Tyr Cys Gln Gln Tyr Gly Asn Ser Pro
                 85                  90                  95
Phe Thr Phe Gly Pro Gly Thr Lys Val Asp Ile Lys Arg
                100                 105
```

<210> SEQ ID NO 36
<211> LENGTH: 108
<212> TYPE: PRT
<213> ORGANISM: Homo sapiens

<400> SEQUENCE: 36

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Asp Met Tyr
                20                  25                  30
Leu Ala Trp Phe Gln Gln Lys Pro Gly Lys Ala Pro Lys Ser Leu Ile
            35                  40                  45
Tyr Ala Ala Ser Ser Leu Gln Ser Gly Val Pro Ser Lys Phe Ser Gly
 50                  55                  60
Ser Gly Phe Gly Thr Asp Phe Thr Leu Thr Ile Ser Ser Leu Gln Pro
 65                  70                  75                  80
Glu Asp Phe Ala Thr Tyr Tyr Cys Gln Gln Tyr Asn Ile Phe Pro Phe
                 85                  90                  95
Thr Phe Gly Pro Gly Thr Lys Val Asp Val Lys Arg
                100                 105
```

<210> SEQ ID NO 37
<211> LENGTH: 108
<212> TYPE: PRT
<213> ORGANISM: Homo sapiens

<400> SEQUENCE: 37

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Arg Asn Asp
                20                  25                  30
Leu Gly Trp Tyr Gln Gln Lys Pro Gly Lys Ala Pro Lys Arg Leu Ile
            35                  40                  45
Tyr Ala Ala Ser Ser Leu Glu Ser Gly Val Pro Ser Arg Phe Ser Gly
 50                  55                  60
Ser Gly Ser Gly Thr Glu Phe Thr Leu Thr Ile Ser Ser Leu Gln Pro
 65                  70                  75                  80
Glu Asp Phe Ala Thr Tyr Tyr Cys Leu Gln His Asn Ser Tyr Pro Trp
                 85                  90                  95
Thr Phe Gly Gln Gly Thr Lys Val Glu Ile Lys Arg
                100                 105
```

<210> SEQ ID NO 38
<211> LENGTH: 114

```
<212> TYPE: PRT
<213> ORGANISM: Homo sapiens

<400> SEQUENCE: 38

Lys Ile Val Met Thr Gln Thr Pro Leu Ala Leu Pro Val Ile Pro Gly
1               5                   10                  15

Glu Pro Ala Ser Ile Ser Cys Arg Ser Ser Gln Ser Leu Val Asp Ser
            20                  25                  30

Asp Asp Gly Asp Thr Tyr Leu Asp Trp Tyr Leu Gln Lys Pro Gly Gln
        35                  40                  45

Ser Pro Gln Val Leu Ile His Arg Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Ile Tyr Tyr Cys Met His
                85                  90                  95

Arg Ile Glu Phe Pro Phe Thr Phe Gly Gly Gly Thr Lys Val Glu Ile
            100                 105                 110

Lys Arg

<210> SEQ ID NO 39
<211> LENGTH: 108
<212> TYPE: PRT
<213> ORGANISM: Homo sapiens

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Arg Pro Gly Lys Ala Pro Lys Arg Leu Ile
        35                  40                  45

Tyr Ala Ala Ser Ser Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys Arg
            100                 105

<210> SEQ ID NO 40
<211> LENGTH: 113
<212> TYPE: PRT
<213> ORGANISM: Homo sapiens

<400> SEQUENCE: 40

Gly Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Met Glu Ala
            85                  90                  95

Leu Gln Thr Met Cys Ser Phe Gly Gln Gly Thr Lys Leu Glu Ile Lys
            100                 105                 110

Arg

<210> SEQ ID NO 41
<211> LENGTH: 113
<212> TYPE: PRT
<213> ORGANISM: Homo sapiens

<400> SEQUENCE: 41

Gly Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Glu Ala
                85                  90                  95

Leu Gln Thr Met Ser Ser Phe Gly Gln Gly Thr Lys Leu Glu Ile Lys
            100                 105                 110

Arg

<210> SEQ ID NO 42
<211> LENGTH: 114
<212> TYPE: PRT
<213> ORGANISM: Homo sapiens

<400> SEQUENCE: 42

Asp Ile Val Met Thr Gln Thr Pro Leu Phe Leu Pro Val Thr Pro Gly
1               5                   10                  15

Glu Pro Ala Ser Ile Ser Cys Arg Ser Ser Gln Thr Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Arg Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Ile Tyr Tyr Cys Met Gln
                85                  90                  95

His Ile Glu Phe Pro Ser Thr Phe Gly Gln Gly Thr Arg Leu Glu Ile
            100                 105                 110

Lys Arg

<210> SEQ ID NO 43
<211> LENGTH: 107
<212> TYPE: PRT
<213> ORGANISM: Homo sapiens

<400> SEQUENCE: 43

```
Ser Tyr Glu Leu Thr Gln Pro Pro Ser Val Ser Pro Gly Gln
1               5                  10                 15

Thr Ala Ser Ile Thr Cys Ser Gly Asp Lys Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Ser Thr Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu Gly
            100                 105
```

<210> SEQ ID NO 44
<211> LENGTH: 113
<212> TYPE: PRT
<213> ORGANISM: Homo sapiens

<400> SEQUENCE: 44

```
Asn Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Asn Tyr Leu Phe Trp Tyr Leu Gln Lys Pro Gly Gln Ser
        35                  40                  45

Pro Gln Leu Leu Ile Tyr Glu Val Ser Tyr Arg Phe Ser Gly Val Pro
50                  55                  60

Asp Arg Phe Ser Gly Ser Gly Ser Gly Thr Asp Phe Ser Leu Lys Ile
65                  70                  75                  80

Ser Arg Val Glu Ala Glu Asp Val Gly Val Tyr Tyr Cys Met Gln Asn
                85                  90                  95

Ile Gln Pro Pro Leu Thr Phe Gly Gln Gly Thr Arg Leu Glu Ile Lys
            100                 105                 110

Arg
```

<210> SEQ ID NO 45
<211> LENGTH: 108
<212> TYPE: PRT
<213> ORGANISM: Homo sapiens

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Val Gln Pro
65                  70                  75                  80

Glu Asp Phe Val Thr Tyr Tyr Cys Leu Gln His Asn Ser Asn Pro Leu
                85                  90                  95

Thr Phe Gly Gly Gly Thr Lys Val Glu Ile Lys Arg
```

<210> SEQ ID NO 46
<211> LENGTH: 108
<212> TYPE: PRT
<213> ORGANISM: Homo sapiens

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Val Gln Pro
65                  70                  75                  80

Glu Asp Phe Val Thr Tyr Tyr Cys Leu Gln His Asn Ser Asn Pro Leu
                85                  90                  95

Thr Phe Gly Gly Gly Thr Lys Val Glu Ile Lys Arg
            100                 105

<210> SEQ ID NO 47
<211> LENGTH: 114
<212> TYPE: PRT
<213> ORGANISM: Homo sapiens

<400> SEQUENCE: 47

Asp Ile Val Leu Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Arg
            20                  25                  30

Asp Asp Gly Asp Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Ser Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Phe Thr Phe Gly Pro Gly Thr Lys Val Asp Ile
            100                 105                 110

Lys Arg

<210> SEQ ID NO 48
<211> LENGTH: 107
<212> TYPE: PRT
<213> ORGANISM: Homo sapiens

<400> SEQUENCE: 48

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

```
Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105
```

<210> SEQ ID NO 49
<211> LENGTH: 106
<212> TYPE: PRT
<213> ORGANISM: Homo sapiens

<400> SEQUENCE: 49

```
Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
             35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
                100                 105
```

<210> SEQ ID NO 50
<211> LENGTH: 326
<212> TYPE: PRT
<213> ORGANISM: Homo sapiens

<400> SEQUENCE: 50

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
             115                 120                 125

Thr Leu Met Ile Ser Arg Thr Pro Glu Val Thr Cys Val Val Val Asp
 130                 135                 140

Val Ser His Glu Asp Pro Glu Val Gln Phe Asn Trp Tyr Val Asp Gly
 145                 150                 155                 160
```

Val Glu Val His Asn Ala Lys Thr Lys Pro Arg Glu Gln Phe Asn
         165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 51
<211> LENGTH: 454
<212> TYPE: PRT
<213> ORGANISM: Homo sapiens

<400> SEQUENCE: 51

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Trp Tyr Asp Gly Ser Asn Lys Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Glu Lys Asp His Tyr Asp Ile Leu Thr Gly Tyr Asn Tyr Tyr
            100                 105                 110

Tyr Gly Leu Asp Val Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Asn Phe Gly Thr Gln Thr
        195                 200                 205

```
Tyr Thr Cys Asn Val Asp His Lys Pro Ser Asn Thr Lys Val Asp Lys
            210                 215                 220

Thr Val Glu Arg Lys Cys Cys Val Glu Cys Pro Pro Cys Pro Ala Pro
225                 230                 235                 240

Pro Val Ala Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser His Glu Asp Pro Glu Val Gln Phe Asn Trp Tyr Val Asp Gly
            275                 280                 285

Val Glu Val His Asn Ala Lys Thr Lys Pro Arg Glu Glu Gln Phe Asn
            290                 295                 300

Ser Thr Phe Arg Val Val Ser Val Leu Thr Val Val His Gln Asp Trp
305                 310                 315                 320

Leu Asn Gly Lys Glu Tyr Lys Cys Lys Val Ser Asn Lys Gly Leu Pro
            325                 330                 335

Ala Pro Ile Glu Lys Thr Ile Ser Lys Thr Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Met Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 52
<211> LENGTH: 214
<212> TYPE: PRT
<213> ORGANISM: Homo sapiens

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Val Gln Pro
65                  70                  75                  80

Glu Asp Phe Val Thr Tyr Tyr Cys Leu Gln His Asn Ser Asn Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

-continued

```
            115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

METHODS FOR TREATING OBESITY AND NONALCOHOLIC FATTY LIVER DISEASE OR NONALCOHOLIC STEATOHEPATITIS USING GLUCAGON RECEPTOR ANTAGONISTIC ANTIBODIES

RELATED PATENT APPLICATIONS

This application is a U.S. National Stage Application pursuant to 35 U.S.C. § 371 of PCT/US2016/025336, filed Mar. 31, 2016, which claims benefit of U.S. Provisional Application No. 62/142,257, filed on Apr. 2, 2015, incorporated in its entirety by reference herein.

TECHNICAL FIELD

Obesity is a complex medical disorder of appetite regulation and/or metabolism resulting in excessive accumulation of adipose tissue mass. Obesity is an important clinical problem and is becoming an epidemic disease in western cultures, affecting more than one-third of the US adult population. It is estimated that about 97 million adults in the United States are overweight or obese. Obesity is further associated with premature death and with a significant increase in mortality and morbidity from stroke, myocardial infarction, congestive heart failure, coronary heart disease, and sudden death. Obesity also exacerbates many health problems, both independently and in association with other diseases. The primary goals of obesity therapy are to reduce excess body weight, improve or prevent obesity-related morbidity and mortality, and maintain long-term weight loss.

Nonalcoholic fatty liver disease (NAFLD), including its more aggressive form nonalcoholic steatohepatitis (NASH), is also increasing in epidemic proportions concurrent with the obesity epidemic (Sowers J R et al., Cardiorenal Med, 1:5-12, 2011). The dramatic rise in obesity and NAFLD appears to be due, in part, to consumption of a western diet (WD) containing high amounts of fat and sugar (e.g., sucrose or fructose), as fructose consumption in the US has more than doubled in the last three decades (Barrera et al, Clin Liver Dis, 18:91-112, 2014). NAFLD is characterized by macrovesicular steatosis of the liver occurring in individuals who consume little or no alcohol. The histological spectrum of NAFLD includes the presence of steatosis alone, fatty liver and inflammation. NASH is a more serious chronic liver disease characterized by excessive fat accumulation in the liver that, for reasons that are still incompletely understood, induces chronic inflammation which leads to progressive fibrosis (scarring) that can lead to cirrhosis, hepatocellular carcinoma (HCC), eventual liver failure and death (Brunt et al., Am. J. Gastroenterol. 94:2467-2474, 1999; Brunt, Semin. Liver Dis. 21:3-16, 2001; Takahashi Y et al., World J Gastroenterol, 18:2300-2308, 2012).

Although NASH has become more and more prevalent, affecting 2%-5% of Americans and 2%-3% of people in the world (Neuschwander-Tetri B A, Am J MEd Sci, 330:326-335, 2005), its underlying cause is still not clear. It most often occurs in persons who are middle-aged and overweight or obese. Many subjects with NASH have elevated blood lipids (e.g., cholesterol and triglycerides), hyperinsulinemia, insulin resistance, and many have diabetes or prediabetes. But not every obese person or every subject with diabetes has NASH. Furthermore, some subjects with NASH are not obese, do not have diabetes, and have normal blood cholesterol and lipids. NASH can occur without any apparent risk factor and can even occur in children. Thus, NASH is not simply obesity that affects the liver. Currently, no specific therapies for NASH exist. The most important recommendations given to persons with this disease are aerobic exercise, manipulations of diet and eating behavior, and reducing their weight (if obese or overweight).

While there are been continued advancements, there remains a pressing need for more research on the molecular mechanisms that underlie obesity and its medical consequences, as well as new approaches for its treatment. Similarly, there remains a pressing need for new methods of treating or preventing NAFLDs in diabetic and non-diabetic subjects.

DISCLOSURE OF THE INVENTION

The present disclosure is based in part on the inventors' unique insight that isolated antigen binding and antagonizing proteins that specifically bind to the human glucagon receptor may provide for improved, effective therapies for treatment of diet induced obesity (DIO) and treatment of NAFLD/NASH in diabetic and non-diabetic subjects. The present inventors propose that the beneficial therapeutic effects provided by regulating glucose output in DIO and/or NAFLD/NASH subjects (via blocking the glucagon receptor) may include: reducing insulin resistance; reducing or preventing hyperinsulinemia, reducing or preventing fat deposits in the liver; reducing or preventing inflammation in the liver; reducing or preventing the accumulation of lipid, e.g., hepatic triacylglycerol, hepatic diacylglycerol, and ceramides; and preventing injury in the liver.

Thus, in one aspect, the present disclosure comprises a method for treating or preventing NAFLD/NASH in a subject, comprising administering to a subject diagnosed with NAFLD/NASH, or a subject at risk of contracting NAFLD/NASH, a therapeutically effective amount of an isolated antagonistic antigen binding protein that specifically binds to the human glucagon receptor. In various embodiments, the isolated antagonistic antigen binding protein comprises an antibody selected from a fully human antibody, a humanized antibody, a chimeric antibody, a monoclonal antibody, a polyclonal antibody, a recombinant antibody, an antigen-binding antibody fragment, a Fab, a Fab', a Fab$_2$, a Fab'$_2$, a IgG, a IgM, a IgA, a IgE, a scFv, a dsFv, a dAb, a nanobody, a unibody, or a diabody. In various embodiments, the antibody is a fully human monoclonal antibody. In various embodiments, the present disclosure comprises a method for treating NAFLD. In various embodiments, the present disclosure comprises a method for treating NASH.

In another aspect, the present disclosure comprises a method for treating or preventing NAFLD/NASH in a subject, comprising (a) administering to a subject diagnosed with NAFLD/NASH, or a subject at risk of contracting NAFLD/NASH, a therapeutically effective amount of an isolated antagonistic antigen binding protein that specifically binds to the human glucagon receptor, and (b) an anti-obesity agent. In various embodiments, the isolated antagonistic antigen binding protein comprises an antibody selected from a fully human antibody, a humanized antibody, a chimeric antibody, a monoclonal antibody, a polyclonal antibody, a recombinant antibody, an antigen-binding antibody fragment, a Fab, a Fab', a Fab$_2$, a Fab'$_2$, a IgG, a IgM, a IgA, a IgE, a scFv, a dsFv, a dAb, a nanobody, a unibody, or a diabody. In various embodiments, the antibody is a fully human monoclonal antibody. In various embodiments, the present disclosure comprises a method for treating NAFLD. In various embodiments, the present disclosure comprises a method for treating NASH. In various embodiments, the anti-obesity agent is selected from gut-selective MTP inhibitors, CCKa agonists, 5HT2c agonists, MCR4 agonists, lipase inhibitors, opioid antagonists, oleoyl-estrone, obinepitide, pramlintide (SYMLIN®), tesofensine, leptin, bromocriptine, orlistat, AOD-9604, and sibutramine.

In another aspect, the present disclosure relates to methods of treating a subject classified as obese (e.g., having a body mass index (BMI) of 30 kg/m$^2$ or more) comprising administering to the subject a therapeutically effective amount of an isolated antagonistic antigen binding protein that specifically binds to the human glucagon receptor. In various embodiments, the isolated antagonistic antigen binding protein comprises an antibody selected from a fully human antibody, a humanized antibody, a chimeric antibody, a monoclonal antibody, a polyclonal antibody, a recombinant antibody, an antigen-binding antibody fragment, a Fab, a Fab', a Fab$_2$, a Fab'$_2$, a IgG, a IgM, a IgA, a IgE, a scFv, a dsFv, a dAb, a nanobody, a unibody, or a diabody. In various embodiments, the antibody is a fully human monoclonal antibody.

In another aspect, the present disclosure relates to methods of treating a subject classified as obese (e.g., having a body mass index (BMI) of 30 kg/m$^2$ or more) comprising: (a) administering to the subject a therapeutically effective amount of an isolated antagonistic antigen binding protein that specifically binds to the human glucagon receptor, and (b) an anti-obesity agent. In various embodiments, the isolated antagonistic antigen binding protein comprises an antibody selected from a fully human antibody, a humanized antibody, a chimeric antibody, a monoclonal antibody, a polyclonal antibody, a recombinant antibody, an antigen-binding antibody fragment, a Fab, a Fab', a Fab$_2$, a Fab'$_2$, a IgG, a IgM, a IgA, a IgE, a scFv, a dsFv, a dAb, a nanobody, a unibody, or a diabody. In various embodiments, the antibody is a fully human monoclonal antibody. In various embodiments, the anti-obesity agent is selected from gut-selective MTP inhibitors, CCKa agonists, 5HT2c agonists, MCR4 agonists, lipase inhibitors, opioid antagonists, oleoyl-estrone, obinepitide, pramlintide (SYMLIN®), tesofensine, leptin, bromocriptine, orlistat, AOD-9604, and sibutramine.

In another aspect, the present disclosure relates to the use of a non-naturally occurring isolated antagonistic antigen binding protein that specifically binds to the human glucagon receptor for the preparation of a medicament for treatment, prophylaxis and/or prevention of nonalcoholic steatohepatitis (NASH) in a subject in need thereof.

In another aspect, the present disclosure relates to the use of a non-naturally occurring isolated antagonistic antigen binding protein that specifically binds to the human glucagon receptor for the preparation of a medicament for treatment, prophylaxis and/or prevention of nonalcoholic fatty liver disease (NAFLD) in a subject in need thereof.

In another aspect, the present disclosure relates to the use of a non-naturally occurring isolated antagonistic antigen binding protein that specifically binds to the human glucagon receptor for the preparation of a medicament for treatment a subject classified as obese (e.g., having a body mass index (BMI) of 30 kg/m$^2$ or more).

In various embodiments, the isolated antagonistic binding protein binds to a human glucagon receptor with a dissociation constant ($K_D$) of at least about $1 \times 10^{-7}$ M, at least about $1 \times 10^{-8}$ M, at least about $1 \times 10^{-9}$ M, at least about $1 \times 10^{-10}$ M, at least about $1 \times 10^{-11}$ M, or at least about $1 \times 10^{-12}$ M.

In various embodiments, the isolated antagonistic binding protein is a fully human antibody which comprises the amino acid sequence encoding the heavy chain variable region of SEQ ID NO: 2 and the amino acid sequence encoding the light chain variable region of SEQ ID NO: 3.

In various embodiments, the isolated antagonistic protein is a fully human antibody which comprises the amino acid sequence encoding the heavy chain variable region of SEQ ID NO: 4 and the amino acid sequence encoding the light chain variable region of SEQ ID NO: 5.

In various embodiments, the isolated antagonistic protein is a fully human antibody which comprises the amino acid sequence encoding the heavy chain variable region of SEQ ID NO: 6 and the amino acid sequence encoding the light chain variable region of SEQ ID NO: 7.

In various embodiments, the isolated antagonistic protein is a fully human antibody which comprises a heavy chain variable region having the amino acid sequence selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28.

In various embodiments, the isolated antagonistic protein is a fully human antibody which comprises a light chain variable region having the amino acid sequence selected from the group consisting of SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, and SEQ ID NO: 47.

In various embodiments, the isolated antagonistic protein is a fully human antibody which comprises the amino acid sequence encoding the heavy chain variable region of SEQ ID NO: 28 and the amino acid sequence encoding the light chain variable region of SEQ ID NO: 47.

In various embodiments, the isolated antagonistic protein is a fully human antibody which comprises the amino acid sequence encoding the heavy chain of SEQ ID NO: 51 and the amino acid sequence encoding the light chain of SEQ ID NO: 52.

In various embodiments, the isolated antagonistic antigen binding protein that specifically binds the human glucagon receptor will be admixed with a pharmaceutically acceptable carrier to form a pharmaceutical composition that can be systemically administered to the subject via intravenous injection, intramuscular injection, subcutaneous injection, intraperitoneal injection, transdermal injection, intra-arterial injection, intrasternal injection, intrathecal injection, intraventricular injection, intraurethral injection, intracranial injection, intrasynovial injection or via infusions.

MODE(S) FOR CARRYING OUT THE INVENTION

Figure 1:
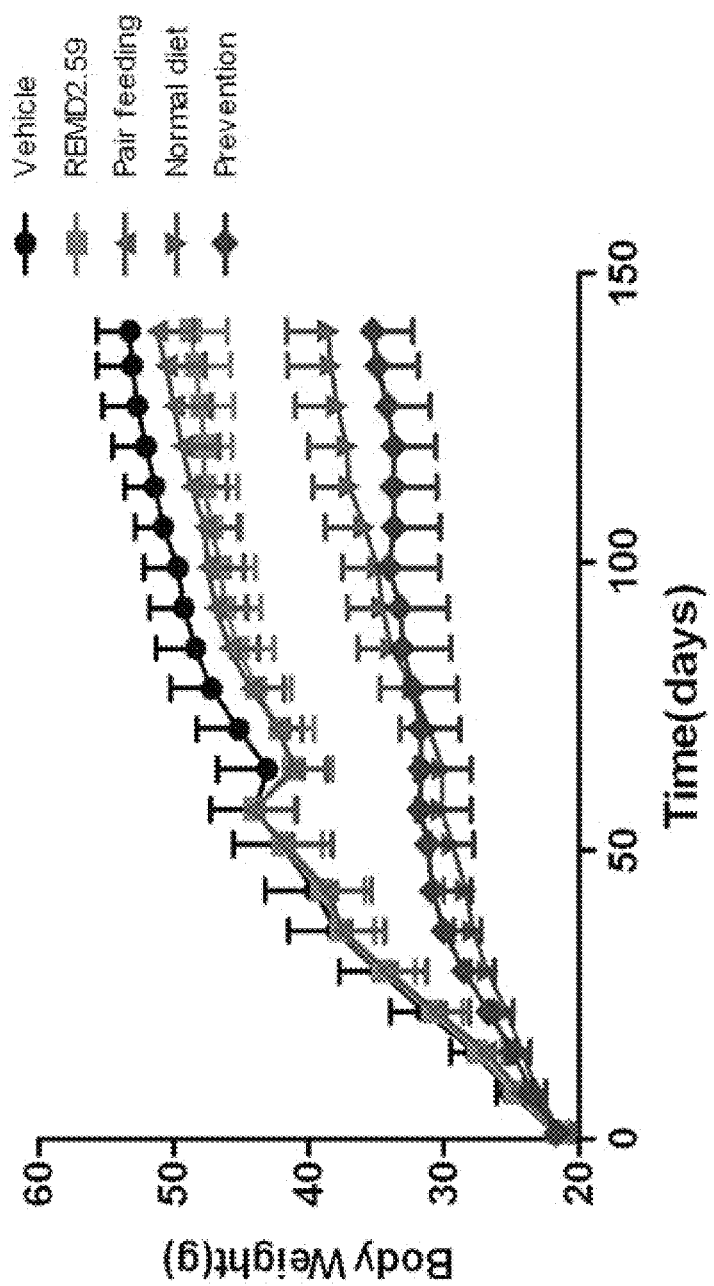
FIG. 1 is a line plot depicting the in vivo effects on body weight (g) for the Vehicle group, REMD2.59 group, Pair feeding group, Normal diet group, and Prevention group as described herein, in a HFD DIO mouse study, evaluated for up to twenty weeks. Treatment commenced on Day 57 (i.e., start of week 9) for all groups but the Prevention group. For the Prevention group, REMD2.59C antibody was administered weekly starting from day 1 of HFD feeding.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those commonly used and well known in the art. The methods and techniques of the present disclosure are generally performed according to conventional methods well known in the art and as described in various general and more specific references that are cited and discussed throughout the present specification unless otherwise indicated. See, e.g., Sambrook et al. Molecular Cloning: A Laboratory Manual, 2nd ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual, Cold Spring Harbor Laboratory Press, Cold Spring Harbor, N.Y. (1990), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those commonly used and well known in the art. Standard techniques are used for chemical syntheses, chemical analyses, pharmaceutical preparation, formulation, and delivery, and treatment of subjects.

Definitions

The terms "peptide" "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric. In certain embodiments, "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond.

Polynucleotide and polypeptide sequences are indicated using standard one- or three-letter abbreviations. Unless otherwise indicated, polypeptide sequences have their amino termini at the left and their carboxy termini at the right, and single-stranded nucleic acid sequences, and the top strand of double-stranded nucleic acid sequences, have their 5' termini at the left and their 3' termini at the right. A particular section of a polypeptide can be designated by amino acid residue number such as amino acids 80 to 119, or by the actual residue at that site such as Ser80 to Ser119. A particular polypeptide or polynucleotide sequence also can be described by explaining how it differs from a reference sequence.

Polypeptides of the disclosure include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" refers to the substitution in a polypeptide of an amino acid with a functionally similar amino acid. The following six groups each contain amino acids that are conservative substitutions for one another:

Alanine (A), Serine (S), and Threonine (T)
   Aspartic acid (D) and Glutamic acid (E)
   Asparagine (N) and Glutamine (Q)
   Arginine (R) and Lysine (K)
   Isoleucine (I), Leucine (L), Methionine (M), and Valine (V)
   Phenylalanine (F), Tyrosine (Y), and Tryptophan (W)

A "non-conservative amino acid substitution" refers to the substitution of a member of one of these classes for a member from another class. In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. Exemplary amino acid substitutions are set forth in Table 1.

TABLE 1

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | |
| Asp | Glu | |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptides as set forth herein using well-known techniques. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a polypeptide that correspond to amino acid residues important for activity or structure in similar polypeptides. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of a polypeptide with respect to its three-dimensional structure. In certain embodiments, one skilled in the art may choose to not make radical changes to amino acid residues predicted to be on the surface of the polypeptide, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

The term "polypeptide fragment" and "truncated polypeptide" as used herein refers to a polypeptide that has an amino-terminal and/or carboxy-terminal deletion as compared to a corresponding full-length protein. In certain embodiments, fragments can be, e.g., at least 5, at least 10, at least 25, at least 50, at least 100, at least 150, at least 200, at least 250, at least 300, at least 350, at least 400, at least 450, at least 500, at least 600, at least 700, at least 800, at least 900 or at least 1000 amino acids in length. In certain embodiments, fragments can also be, e.g., at most 1000, at most 900, at most 800, at most 700, at most 600, at most 500, at most 450, at most 400, at most 350, at most 300, at most 250, at most 200, at most 150, at most 100, at most 50, at most 25, at most 10, or at most 5 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

The terms "polypeptide variant" and "polypeptide mutant" as used herein refers to a polypeptide that comprises an amino acid sequence wherein one or more amino acid residues are inserted into, deleted from and/or substituted into the amino acid sequence relative to another polypeptide sequence. In certain embodiments, the number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length. Variants of the present disclosure include fusion proteins.

A "derivative" of a polypeptide is a polypeptide that has been chemically modified, e.g., conjugation to another chemical moiety such as, for example, polyethylene glycol, albumin (e.g., human serum albumin), phosphorylation, and glycosylation.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. In certain embodiments, the % identity is selected from, e.g., at least 60%, at least 65%, at least 70%, at least 75%, at least 80%, at least 85%, at least 90%, at least 95%, or at least 99% or more sequence identity to a given sequence. In certain embodiments, the % identity is in the range of, e.g., about 60% to about 70%, about 70% to about 80%, about 80% to about 85%, about 85% to about 90%, about 90% to about 95%, or about 95% to about 99%.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. In certain embodiments, the % homology is selected from, e.g., at least 60%, at least 65%, at least 70%, at least 75%, at least 80%, at least 85%, at least 90%, at least 95%, or at least 99% or more sequence homology to a given sequence. In certain embodiments, the % homology is in the range of, e.g., about 60% to about 70%, about 70% to about 80%, about 80% to about 85%, about 85% to about 90%, about 90% to about 95%, or about 95% to about 99%.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, J. Mol. Biol. 215:403-10 (with special reference to the published default setting, i.e., parameters w=4, t=17) and Altschul et al., 1997, Nucleic Acids Res., 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is, e.g., less than about 0.1, less than about 0.01, or less than about 0.001.

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

A protein or polypeptide is "substantially pure," "substantially homogeneous," or "substantially purified" when at least about 60% to 75% of a sample exhibits a single species of polypeptide. A substantially pure polypeptide or protein will typically comprise about 50%, 60%, 70%, 80% or 90% W/W of a protein sample, more usually about 95%, and e.g., will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

An "antigen binding and antagonizing protein" is a protein comprising a portion that binds to an antigen and, optionally, a scaffold or framework portion that allows the antigen binding portion to adopt a conformation that promotes binding of the isolated antagonistic antigen binding protein to the antigen. Examples of antigen binding and antagonizing proteins include antibodies, antibody fragments (e.g., an antigen binding portion of an antibody), antibody derivatives, and antibody analogs. The isolated antagonistic antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the isolated antagonistic antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129 (2003); Roque et al., Biotechnol. Prog. 20:639-654 (2004). In addition, peptide antibody mimetics ("PAMs") can be used, as well as scaffolds based on antibody mimetics utilizing fibronection components as a scaffold.

An isolated antagonistic antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

An "antibody" refers to a protein comprising one or more polypeptides substantially or partially encoded by immunoglobulin genes or fragments of immunoglobulin genes and having specificity to a tumor antigen or specificity to a molecule overexpressed in a pathological state. The recognized immunoglobulin genes include the kappa, lambda, alpha, gamma, delta, epsilon and mu constant region genes, as well as subtypes of these genes and myriad of immunoglobulin variable region genes. Light chains (LC) are classified as either kappa or lambda. Heavy chains (HC) are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition.

In a full-length antibody, each heavy chain is comprised of a heavy chain variable region (abbreviated herein as HCVR or $V_H$) and a heavy chain constant region. The heavy chain constant region is comprised of three domains, $C_{H1}$, $C_{H2}$ and $C_{H3}$ (and in some instances, $C_{H4}$). Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: $FR_1$, $CDR_1$, $FR_2$, $CDR_2$, $FR_3$, $CDR_3$, $FR_4$. The extent of the framework and CDRs has been defined. The sequences of the framework regions of different light or heavy chains are relatively conserved within a species, such as humans. The framework region of an antibody, that is the combined framework regions of the constituent light and heavy chains, serves to position and align the CDRs in three-dimensional space. Immunoglobulin molecules can be of any type (e.g., IgG, IgE, IgM, IgD, IgA and IgY), class (e.g., IgG1, IgG2, IgG 3, IgG4, IgA1 and IgA2) or subclass.

Antibodies exist as intact immunoglobulins or as a number of well characterized fragments. Such fragments include Fab fragments, Fab' fragments, Fab$_2$, F(ab)'$_2$ fragments, single chain Fv proteins ("scFv") and disulfide stabilized Fv proteins ("dsFv"), that bind to the target antigen. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. While various antibody fragments are defined in terms of the digestion of an intact antibody, one of skill will appreciate that such fragments may be synthesized de novo either chemically or by utilizing recombinant DNA methodology. Thus, as used herein, the term antibody encompasses e.g., monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, F(ab')$_2$ fragments, antibody fragments that exhibit the desired biological activity, disulfide-linked Fvs (sdFv), intrabodies, and epitope-binding fragments or antigen binding fragments of any of the above.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and C.sub.H1 domains; an Fv fragment has the $V_L$ and VdH domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, US App. Pub. No. 05/0202512, 04/0202995, 04/0038291, 04/0009507, 03/0039958, Ward et al., Nature 341:544-546 (1989)).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., Science 242:423-26 (1988) and Huston et al., 1988, Proc. Natl. Acad. Sci. USA 85:5879-83 (1988)). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48 (1993), and Poljak et al., Structure 2:1121-23 (1994)). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

An isolated antagonistic antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

An isolated antagonistic antigen binding protein of the present disclosure, including an antibody, "specifically binds" to an antigen, such as the human glucagon receptor if it binds to the antigen with a high binding affinity as determined by a dissociation constant (Kd, or corresponding Kb, as defined below) value of $10^{-7}$ M or less. An isolated antagonistic antigen binding protein that specifically binds to the human glucagon receptor may be able to bind to glucagon receptors from other species as well with the same or different affinities.

An "epitope" is the portion of a molecule that is bound by an isolated antagonistic antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding and antagonizing protein).

The term "blood glucose level", or "level of blood glucose" shall mean blood glucose concentration. In certain embodiments, a blood glucose level is a plasma glucose level. Plasma glucose may be determined in accordance with, e.g., Etgen et al., Metabolism, 49(5): 684-688, 2000) or calculated from a conversion of whole blood glucose concentration in accordance with D'Orazio et al., Clin. Chem. Lab. Med., 44(12):1486-1490, 2006.

The term "normal glucose levels" refers to mean plasma glucose values in humans of less than about 100 mg/dL for fasting levels, and less than about 145 mg/dL for 2-hour post-prandial levels or 125 mg/dL for a random glucose. The term "elevated blood glucose level" or "elevated levels of blood glucose" shall mean an elevated blood glucose level such as that found in a subject demonstrating clinically inappropriate basal and postprandial hyperglycemia or such as that found in a subject in oral glucose tolerance test (oGTT), with "elevated levels of blood glucose" being greater than about 100 mg/dL when tested under fasting conditions, and greater than about 200 mg/dL when tested at 1 hour.

The terms "glucagon inhibitor", "glucagon suppressor" and "glucagon antagonist" are used interchangeably. Each is a molecule that detectably inhibits glucagon signaling. The inhibition caused by an inhibitor need not be complete so long as the inhibition is detectable using an assay that is recognized and understood in the art as being determinative of glucagon signaling inhibition.

A "pharmaceutical composition" refers to a composition suitable for pharmaceutical use in an animal or human. A pharmaceutical composition comprises a pharmacologically and/or therapeutically effective amount of an active agent and a pharmaceutically acceptable carrier. "Pharmaceutically acceptable carrier" refers to compositions that do not produce adverse, allergic, or other untoward reactions when administered to an animal or a human. As used herein "pharmaceutically acceptable carrier" refers to any of the standard pharmaceutical carriers, vehicles, buffers, and carriers, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 21st Ed. 2005, Mack Publishing Co, Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

As used herein, a "therapeutically effective amount" of an isolated antagonistic antigen binding protein that specifically binds the human glucagon receptor refers to an amount of such protein that, when provided to a subject in accordance with the disclosed and claimed methods effects one of the following biological activities: treats obesity; treats NAFLD; treats NASH; or reduces, suppresses, attenuates, or inhibits one or more symptoms of NASH.

The terms "treat", "treating" and "treatment" refer refers to an approach for obtaining beneficial or desired clinical results. Further, references herein to "treatment" include references to curative, palliative and prophylactic treatment. For purposes of this disclosure, beneficial or desired clinical results include, but are not limited to, one or more of the following: improvement in blood glucose to within about 80-180 mg/dL, or to within about 80-170 mg/dL, or to within about 80-160 mg/dL, or to within about 80-150 mg/dL, or to within about 80-140 mg/dL, or an improvement in any one or more conditions, diseases, or symptoms associated with, or resulting from, elevated levels of blood glucose including, but not limited to, hyperglycemia, hyperglucanemia, and hyperinsulinemia.

As used herein and in the appended claims, the singular forms "a," "or," and "the" include plural referents unless the context clearly dictates otherwise. It is understood that aspects and variations of the disclosure described herein include "consisting" and/or "consisting essentially of" aspects and variation.

Reference to "about" a value or parameter herein includes (and describes) variations that are directed to that value or parameter per se. For example, description referring to "about X" includes description of "X".

Obesity

Obesity is a medical condition in which excess body fat has accumulated in multiple tissues, including the liver, to the extent that it may have an adverse effect on health. Typically defined as a body mass index (BMI)(a measurement obtained by dividing a person's weight by the square of the person's height) of 30 kg/m$^2$ or more, the prevalence of obesity has risen significantly in the past decade in the United States and many other developed countries and become a world-wide public health concern.

Obesity is most commonly caused by a combination of excessive food energy intake, lack of physical activity, and genetic susceptibility, although a few cases are caused primarily by genes, endocrine disorders, medications, or psychiatric illness. Obesity increases the likelihood of various diseases, particularly heart disease, type 2 diabetes, NAFLD/NASH, obstructive sleep apnea, certain types of cancer, osteoarthritis, and asthma. Complications are either directly caused by obesity or indirectly related through mechanisms sharing a common cause such as a poor diet or a sedentary lifestyle. The strength of the link between obesity and specific conditions varies. One of the strongest is the link with type 2 diabetes. Excess body fat underlies 64% of cases of diabetes in men and 77% of cases in women.

Current treatment modalities typically include diet and exercise programs, lifestyle management, pharmacotherapy, and surgery. Treatment decisions are made based on severity of obesity, seriousness of associated medical conditions, subject risk status, and subject expectations. Notable improvements in cardiovascular risk and the incidence of diabetes have been observed with weight loss of 5-10% of body weight, supporting clinical guidelines for the treatment of obesity that recommend a target threshold of 10% reduction in body weight from baseline values. Unfortunately, the available pharmacological therapies to facilitate weight loss fail to provide adequate benefit to many obese subjects because of side effects, contraindications or lack of positive response (National Heart, Lung and Blood Institute, Clinical guidelines on the identification, evaluation, and treatment of overweight and obesity in adults: the evidence report, NIH Publication No. 98-4083, September 1998).

Bariatric surgery may be considered as a weight loss intervention for subjects at or exceeding a BMI of 40 kg/m$^2$. Subjects with a BMI of ~35 kg/m$^2$ and with an associated serious medical condition are also candidates for this treatment option. Unfortunately, postoperative complications commonly result from bariatric surgical procedures, including bleeding, embolism or thrombosis, wound complications, deep infections, pulmonary complications, and gastrointestinal obstruction; reoperation during the postoperative period is sometimes necessary to address these complications. Rates of reoperation or conversion surgery beyond the postoperative period depend upon the type of bariatric procedure, and in one study ranged from 17% to 31%. Intestinal absorptive abnormalities, such as micronutrient deficiency and protein-calorie malnutrition, also are typically seen with bypass procedures, requiring lifelong nutrient supplementation. Major and serious adverse outcomes associated with bariatric surgery are common, observed in approximately 4 percent of procedures performed (including death in 0.3 to 2 percent of all subjects receiving laparoscopic banding or bypass surgeries, respectively).

There clearly still exists a pressing need for improved and/or new methods of treatment of obesity, including, e.g., diet induced obesity (DIO). The present disclosure provides antigen binding and antagonizing proteins that specifically bind to the human glucagon receptor that may provide for improved, effective therapies for treatment of DIO in diabetic and non-diabetic subjects.

Nonalcoholic Fatty Liver Disease (NAFLD) and Nonalcoholic Steatohepatitis NASH

Nonalcoholic fatty liver disease (NAFLD) is highly prevalent in the Western population. Recent studies suggest that this disease may occur at a frequency of 70% in obese individuals and 35% in lean individuals (Wanless I R, et al., Hepatology, 12:1106-1110, 1990). NAFLD is characterized by macrovesicular steatosis of the liver occurring in individuals who consume little or no alcohol. The histological spectrum of NAFLD is classified as simple steatosis alone, or nonalcoholic steatohepatitis (NASH). Some epidemiological studies implicate diets higher in saturated fat (Musso G, et al., Hepatology, 37:909-916, 2003). However, NAFLD is also strongly associated with the ingestion of fructose, especially from sweetened beverages (Ouyang X, et al., J Hepatol., 48:993-999, 2008). The classic Western diet is high in both saturated fats and in sugar.

Hepatic insulin resistance (which can lead to hyperglycemia and/or hyperinsulinemia) that develops with consumption of high-fat and high-sugar diets (e.g., simple sugar such as glucose, fructose) is closely linked to NAFLD. Accumulating evidence suggests that hepatic insulin resistance is caused by dysfunction in three pathways of energy metabolism (Samuel et al, Cell, 148:852-871, 2012). First, excess carbohydrate flux (e.g., glucose, fructose) is associated with resistance to the suppressive effect of insulin on hepatic glucose production and excess disposal of carbons via de novo lipogenesis (Id). Second, elevation in lipid synthesis (or reduced lipid secretion/export) leads to accumulation of hepatic triacylglycerols (TAG) which are inert but often track with increased levels of bioactive lipid intermediates diacylglycerols (DAG) and ceramides that putatively lead to hepatic insulin resistance (Kumashiro N et al, Proc Natl Acad Sci USA, 108:16381-16385, 2011). Third, the hepaticsteatosis linked to insulin resistance is associated with mitochondrial dysfunction and altered hepatic fatty acid oxidation (Rector R S et al., J Hepatol, 52:727-736, 2010).

By mechanisms that are not completely understood, NAFLD may progress to a more aggressive form, nonalcoholic steatohepatitis (NASH), or progress to fibrosis, cirrhosis, and hepatocellular carcinoma (HCC). NASH is now accepted as a progressive metabolic liver disease that affects 2%-5% of Americans and that can lead to cirrhosis and permanent liver failure (Brunt et al., supra, 1999; Brunt, supra, 2001; Ludwig et al., J. Gastroenterol. Hepatol. 12:398-403, 1997). The current model of pathogenesis from healthy liver to NASH suggests a two-hit progression. First, insulin resistance causes lipid accumulation in hepatocytes (first hit). Secondly, it is proposed that cellular insults such as oxidative stress, lipid peroxidation, direct lipid toxicity, mitochondrial dysfunction, and/or infection causes hepatic inflammation (second hit), resulting in NASH (Brunt, supra, 2001).

The engorgement of the liver with lipid causes severe insulin resistance in the liver and abnormal glucose production (Samuel et al., J. Biol. Chem. 279:32345-32353, 2004). Steatosis caused by the insulin resistance is believed to sensitize the liver to metabolic injury leading to inflammation, necrosis, and fibrosis (James et al., Lancet 353:1634-1636, 1999; Ludwig et al., Mayo Clin. Proc. 55:434-438, 1980; Day, Gut 50:585-588, 2002; Browning et al., J. Clin. Invest. 114:147-152, 2004). Thus, steatosis is a constant feature of NASH, but NASH is only distinguishable by liver biopsy. The assessment and severity of NASH is made histologically based on the patterns and degrees of hepatic steatosis, inflammation, and injury and, by definition, occurs only in the absence of significant alcohol consumption (Brunt, supra, 2001). While steatosis is seen in both animal and human models, NASH is only fully appreciated in the human condition (Browning et al., supra, 2004). Thus, understanding the clinical variation observed in NASH is critical for the development of therapeutic strategies for this condition.

Currently there are no good clinical markers that allow for the identification of patients with NASH. Similarly, there are no therapies to slow down or alter the course of further disease progression in NASH. Such markers and treatment for NASH are needed in the art. NASH ranks as one of the major causes of cirrhosis in America, behind hepatitis C and alcoholic liver disease. Thus, there exists a need in the art for methods of treating NASH. The present disclosure provides antigen binding and antagonizing proteins that specifically bind to the human glucagon receptor that may provide for improved, effective therapies for treatment and prevention of NASH in diabetic and non-diabetic subjects.

Glucagon Receptor and Antigen Binding and Antagonizing Proteins

Glucagon is a 29 amino acid hormone processed from its pre-pro-form in the pancreatic alpha cells by cell specific expression of prohormone convertase 2 (PC2), a neuroendocrine-specific protease involved in the intracellular maturation of prohormones and proneuropeptides (Furuta et al., J. Biol. Chem. 276: 27197-27202 (2001)). In vivo, glucagon is a major counter-regulatory hormone for insulin actions. During fasting, glucagon secretion increases in response to falling glucose levels. Increased glucagon secretion stimulates glucose production by promoting hepatic glycogenolysis and gluconeogenesis (Dunning and Gerich, Endocrine Reviews, 28:253-283 (2007)). Thus glucagon counterbalances the effects of insulin in maintaining normal levels of glucose in animals.

The biological effects of glucagon are mediated through the binding and subsequent activation of a specific cell surface receptor, the glucagon receptor. The glucagon receptor (GCGR) is a member of the secretin subfamily (family B) of G-protein-coupled receptors. The human GCGR is a 477 amino acid sequence GPCR and the amino acid sequence of GCGR is highly conserved across species (Mayo et al, Pharmacological Rev., 55:167-194, (2003)). The glucagon receptor is predominantly expressed in the liver, where it regulates hepatic glucose output, on the kidney, and on islet β-cells, reflecting its role in gluconeogenesis. The activation of the glucagon receptors in the liver stimulates the activity of adenyl cyclase and phosphoinositol turnover which subsequently results in increased expression of gluconeogenic enzymes including phosphoenolpyruvate carboxykinase (PEPCK), fructose-1,6-bisphosphatase (FB-Pase-1), and glucose-6-phosphatase (G-6-Pase). In addition, glucagon signaling activates glycogen phosphorylase and inhibits glycogen synthase. Studies have shown that higher basal glucagon levels and lack of suppression of postprandial glucagon secretion contribute to diabetic conditions in humans (Muller et al., N Eng J Med 283: 109-115 (1970)). As such, methods of controlling and lowering blood glucose by targeting glucagon production or function using a GCGR antagonist have been explored.

In various embodiments, the antigen binding and antagonizing proteins of the present disclosure may be selected to bind to membrane-bound glucagon receptors as expressed on cells, and inhibit or block glucagon signaling through the glucagon receptor. In various embodiments, the antigen binding and antagonizing proteins of the present disclosure specifically bind to the human glucagon receptor. In various embodiments, the antigen binding and antagonizing proteins binding to the human glucagon receptor may also bind to the glucagon receptors of other species. The polynucleotide and polypeptide sequences for several species of glucagon receptor are known (see, e.g., U.S. Pat. No. 7,947,809, herein incorporated by reference in its entirety for its specific teaching of polynucleotide and polypeptide sequences of a human, rat, mouse and cynomolgus glucagon receptor). In various embodiments of the present disclosure, the antigen binding and antagonizing proteins specifically bind the human glucagon receptor having the amino acid sequence set forth in SEQ ID NO: 1:

```
Glucagon Receptor Human (Homo sapiens) amino acid
sequence (Accession Number AAI04855)
                                          (SEQ ID NO: 1)
MPPCQPQRPLLLLLLLLACQPQVPSAQVMDFLFEKWKLYGDQCHHNLSL

LPPPTELVCNRTFDKYSCWPDTPANTTANISCPWYLPWHHKVQHRFVFK

RCGPDGQWVRGPRGQPWRDASQCQMDGEEIEVQKEVAKMYSSFQVMYTV

GYSLSLGALLLALAILGGLSKLHCTRNAIHANLFASFVLKASSVLVIDG

LLRTRYSQKIGDDLSVSTWLSDGAVAGCRVAAVFMQYGIVANYCWLLVE

GLYLHNLLGLATLPERSFFSLYLGIGWGAPMLFVVPWAVVKCLFENVQC

WTSNDNMGFWWILRFPVFLAILINFFIFVRIVQLLVAKLRARQMHHTDY

KFRLAKSTLTLIPLLGVHEVVFAFVTDEHAQGTLRSAKLFFDLFLSSFQ

GLLVAVLYCFLNKEVQSELRRRWHRWRLGKVLWEERNTSNHRASSSPGH

GPPSKELQFGRGGGSQDSSAETPLAGGLPRLAESPF
```

In various embodiments, the antigen binding and antagonizing proteins of the present disclosure specifically bind glucagon receptors which have at least 70%, at least 75%, at least 80%, at least 85%, at least 90%, at least 95%, at least 96%, at least 97%, at least 98%, or at least 99% identity (as calculated using methods known in the art and described herein) to the glucagon receptors described in the cited references are also included in the present disclosure.

The antigen binding and antagonizing proteins of the present disclosure function to block the interaction between glucagon and its receptor, thereby inhibiting the glucose elevating effects of glucagon. As such, the use of the antigen binding and antagonizing proteins of the present disclosure are an effective means of achieving normal levels of glucose, thereby ameliorating, or preventing one or more symptoms of, or long term complications caused by diabetes including, but not limited to, hyperglycemia, hyperglucanemia, and hyperinsulinemia. The use of the antigen binding and antagonizing proteins of the present disclosure are also an effective means of achieving normal levels of glucose in non-diabetic patients, thereby lowering the risk of hyperglycemia, hyperglucanemia, and hyperinsulinemia in subjects having disorders including, but not limited to, obesity or NAFLDs, and for treating such non-diabetic disorders.

Methods of generating antibodies that bind to antigens such as the human glucagon receptor are known to those skilled in the art. For example, a method for generating a monoclonal antibody that binds specifically to a targeted antigen polypeptide may comprise administering to a mouse an amount of an immunogenic composition comprising the targeted antigen polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the targeted antigen polypeptide. Once obtained, a hybridoma can be propagated in a cell culture, optionally in culture conditions where the hybridoma-derived cells produce the monoclonal antibody that binds specifically to targeted antigen polypeptide. The monoclonal antibody may be purified from the cell culture. A variety of different techniques are then available for testing an antigen/antibody interaction to identify particularly desirable antibodies.

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies. See e.g., Jakobovits et al., Proc. Natl. Acad. Sci. (U.S.A.), 90: 2551-2555, 1993; Jakobovits et al., Nature, 362: 255-258, 1993; Lonberg et al., U.S. Pat. No. 5,545,806; and Surani et al., U.S. Pat. No. 5,545,807.

Antibodies can be engineered in numerous ways. They can be made as single-chain antibodies (including small modular immunopharmaceuticals or SMIPs™), Fab and F(ab')$_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al., Science, 240:1041-1043, 1988; Liu et al., Proc. Natl. Acad. Sci. (U.S.A.), 84:3439-3443, 1987; Liu et al., J. Immunol., 139:3521-3526, 1987; Sun et al., Proc. Natl. Acad. Sci. (U.S.A.), 84:214-218, 1987; Nishimura et al., Canc. Res., 47:999-1005, 1987; Wood et al., Nature, 314:446-449, 1985; and Shaw et al., J. Natl Cancer Inst., 80:1553-1559, 1988).

Methods for humanizing antibodies have been described in the art. In some embodiments, a humanized antibody has one or more amino acid residues introduced from a source that is nonhuman, in addition to the nonhuman CDRs. Humanization can be essentially performed following the method of Winter and co-workers (Jones et al., Nature, 321:522-525, 1986; Riechmann et al., Nature, 332:323-327, 1988; Verhoeyen et al., Science, 239:1534-1536, 1988), by substituting hypervariable region sequences for the corresponding sequences of a human antibody. Accordingly, such "humanized" antibodies are chimeric antibodies (U.S. Pat. No. 4,816,567) wherein substantially less than an intact human variable region has been substituted by the corresponding sequence from a nonhuman species. In practice, humanized antibodies are typically human antibodies in which some hypervariable region residues and possibly some framework region residues are substituted by residues from analogous sites in rodent antibodies.

U.S. Pat. No. 5,693,761 to Queen et al, discloses a refinement on Winter et al. for humanizing antibodies, and is based on the premise that ascribes avidity loss to problems in the structural motifs in the humanized framework which, because of steric or other chemical incompatibility, interfere with the folding of the CDRs into the binding-capable conformation found in the mouse antibody. To address this problem, Queen teaches using human framework sequences closely homologous in linear peptide sequence to framework sequences of the mouse antibody to be humanized. Accordingly, the methods of Queen focus on comparing framework sequences between species. Typically, all available human variable region sequences are compared to a particular mouse sequence and the percentage identity between correspondent framework residues is calculated. The human variable region with the highest percentage is selected to provide the framework sequences for the humanizing project. Queen also teaches that it is important to retain in the humanized framework, certain amino acid residues from the mouse framework critical for supporting the CDRs in a binding-capable conformation. Potential criticality is assessed from molecular models. Candidate residues for retention are typically those adjacent in linear sequence to a CDR or physically within 6 Å of any CDR residue.

In other approaches, the importance of particular framework amino acid residues is determined experimentally once a low-avidity humanized construct is obtained, by reversion of single residues to the mouse sequence and assaying antigen binding as described by Riechmann et al, 1988. Another example approach for identifying important amino acids in framework sequences is disclosed by U.S. Pat. No. 5,821,337 to Carter et al, and by U.S. Pat. No. 5,859,205 to Adair et al. These references disclose specific Kabat residue positions in the framework, which, in a humanized antibody may require substitution with the correspondent mouse amino acid to preserve avidity.

Another method of humanizing antibodies, referred to as "framework shuffling", relies on generating a combinatorial library with nonhuman CDR variable regions fused in frame into a pool of individual human germline frameworks (Dall'Acqua et al., Methods, 36:43, 2005). The libraries are then screened to identify clones that encode humanized antibodies which retain good binding.

The choice of human variable regions, both light and heavy, to be used in making the humanized antibodies is very important to reduce antigenicity. According to the so-called "best-fit" method, the sequence of the variable region of a rodent antibody is screened against the entire library of known human variable-domain sequences. The human sequence that is closest to that of the rodent is then accepted as the human framework region (framework region) for the humanized antibody (Sims et al., J. Immunol., 151:2296, 1993; Chothia et al., J. Mol. Biol., 196:901, 1987). Another method uses a particular framework region derived from the consensus sequence of all human antibodies of a particular subgroup of light or heavy chain variable regions. The same framework may be used for several different humanized antibodies (Carter et al., Proc. Natl. Acad. Sci. (U.S.A.), 89:4285, 1992; Presta et al., J. Immunol., 151:2623, 1993).

The choice of nonhuman residues to substitute into the human variable region can be influenced by a variety of factors. These factors include, for example, the rarity of the amino acid in a particular position, the probability of interaction with either the CDRs or the antigen, and the probability of participating in the interface between the light and heavy chain variable domain interface. (See, for example, U.S. Pat. Nos. 5,693,761, 6,632,927, and 6,639,055). One method to analyze these factors is through the use of three-dimensional models of the nonhuman and humanized sequences. Three-dimensional immunoglobulin models are commonly available and are familiar to those skilled in the art. Computer programs are available that illustrate and display probable three-dimensional conformational structures of selected candidate immunoglobulin sequences.

Inspection of these displays permits analysis of the likely role of the residues in the functioning of the candidate immunoglobulin sequence, e.g., the analysis of residues that influence the ability of the candidate immunoglobulin to bind its antigen. In this way, nonhuman residues can be selected and substituted for human variable region residues in order to achieve the desired antibody characteristic, such as increased affinity for the target antigen(s).

Methods for making fully human antibodies have been described in the art. By way of example, a method for producing an anti-GCGR antibody or antigen binding antibody fragment thereof comprises the steps of synthesizing a library of human antibodies on phage, screening the library with GCGR or an antibody binding portion thereof, isolating phage that bind GCGR, and obtaining the antibody from the phage. By way of another example, one method for preparing the library of antibodies for use in phage display techniques comprises the steps of immunizing a non-human animal comprising human immunoglobulin loci with GCGR or an antigenic portion thereof to create an immune response, extracting antibody-producing cells from the immunized animal; isolating RNA encoding heavy and light chains of antibodies of the disclosure from the extracted cells, reverse transcribing the RNA to produce cDNA, amplifying the cDNA using primers, and inserting the cDNA into a phage display vector such that antibodies are expressed on the phage. Recombinant anti-GCGR antibodies of the disclosure may be obtained in this way.

Again, by way of example, recombinant human anti-GCGR antibodies of the disclosure can also be isolated by screening a recombinant combinatorial antibody library. Preferably the library is a scFv phage display library, generated using human $V_L$ and $V_H$ cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., Bio/Technology, 9:1370-1372 (1991); Hay et al., Hum. Antibod. Hybridomas, 3:81-85, 1992; Huse et al., Science, 246:1275-1281, 1989; McCafferty et al., Nature, 348:552-554, 1990; Griffiths et al., EMBO J., 12:725-734, 1993; Hawkins et al., J. Mol. Biol., 226:889-896, 1992; Clackson et al., Nature, 352:624-628, 1991; Gram et al., Proc. Natl. Acad. Sci. (U.S.A.), 89:3576-3580, 1992; Garrad et al., Bio/Technology, 9:1373-1377, 1991; Hoogenboom et al., Nuc. Acid Res., 19:4133-4137, 1991; and Barbas et al., Proc. Natl. Acad. Sci. (U.S.A.), 88:7978-7982, 1991), all incorporated herein by reference.

Human antibodies are also produced by immunizing a non-human, transgenic animal comprising within its genome some or all of human immunoglobulin heavy chain and light chain loci with a human IgE antigen, e.g., a XenoMouse™ animal (Abgenix, Inc./Amgen, Inc.—Fremont, Calif.). XenoMouse™ mice are engineered mouse strains that comprise large fragments of human immunoglobulin heavy chain and light chain loci and are deficient in mouse antibody production. See, e.g., Green et al., Nature Genetics, 7:13-21, 1994 and U.S. Pat. Nos. 5,916,771, 5,939,598, 5,985,615, 5,998,209, 6,075,181, 6,091,001, 6,114,598, 6,130,364, 6,162,963 and 6,150,584. XenoMouse™ mice produce an adult-like human repertoire of fully human antibodies and generate antigen-specific human antibodies. In some embodiments, the XenoMouse™ mice contain approximately 80% of the human antibody V gene repertoire through introduction of megabase sized, germline configuration fragments of the human heavy chain loci and kappa light chain loci in yeast artificial chromosome (YAC). In other embodiments, XenoMouse™ mice further contain approximately all of the human lambda light chain locus. See Mendez et al., Nature Genetics, 15:146-156, 1997; Green and Jakobovits, J. Exp. Med., 188:483-495, 1998; and WO 98/24893.

In various embodiments, the isolated antagonistic antigen binding protein of the present disclosure utilize an antibody or antigen binding antibody fragment thereof is a polyclonal antibody, a monoclonal antibody or antigen-binding fragment thereof, a recombinant antibody, a diabody, a chimerized or chimeric antibody or antigen-binding fragment thereof, a humanized antibody or antigen-binding fragment thereof, a fully human antibody or antigen-binding fragment thereof, a CDR-grafted antibody or antigen-binding fragment thereof, a single chain antibody, an Fv, an Fd, an Fab, an Fab', or an F(ab')$_2$, and synthetic or semi-synthetic antibodies.

In various embodiments, the isolated antagonistic antigen binding protein of the present disclosure utilize an antibody or antigen-binding fragment that binds to a glucagon receptor antigen with a dissociation constant ($K_D$) of, e.g., at least about $1 \times 10^{-7}$ M, at least about $1 \times 10^{-8}$ M, at least about $1 \times 10^{-9}$ M, at least about $1 \times 10^{-10}$ M, at least about $1 \times 10^{-11}$ M, or at least about $1 \times 10^{-12}$ M. In various embodiments, the isolated antagonistic antigen binding protein of the present disclosure utilize an antibody or antigen-binding fragment that binds to a glucagon receptor antigen with a dissociation constant ($K_D$) in the range of, e.g., at least about $1 \times 10^{-7}$ M to at least about $1 \times 10^{-8}$ M, at least about $1 \times 10^{-8}$ M to at least about $1 \times 10^{-9}$ M, at least about $1 \times 10^{-9}$ M to at least about $1 \times 10^{-10}$ M, at least about $1 \times 10^{-10}$ M to at least about $1 \times 10^{-11}$ M, or at least about $1 \times 10^{-11}$ M to at least about $1 \times 10^{-12}$ M.

Antibodies to the glucagon receptor have been described in, e.g., U.S. Pat. Nos. 5,770,445; 7,947,809; 7,968,686; 8,545,847; 8,771,696; 9,102,732; 9,248,189; European patent application EP2074149A2; EP patent EP0658200B1; U.S. patent publications 2009/0041784; 2009/0252727; 2013/0344538; 2014/0335091; and 20160075778 and PCT publication WO2008/036341. In various embodiments of the present invention, the isolated antagonistic antigen binding protein is an anti-GCGR ("antagonistic") antibody or antigen-binding fragment which comprises the polynucleotide and polypeptide sequences set forth in, e.g., U.S. Pat. Nos. 7,947,809, and 8,158,759, each herein incorporated by reference in its entirety for its specific teaching of polynucleotide and polypeptide sequences of various anti-GCGR antibodies or antigen-binding fragments.

In various embodiments of the present disclosure the antibody may be an anti-GCGR antibody that has the same or higher antigen-binding affinity as that of the antibody comprising the heavy chain variable region sequence as set forth in SEQ ID NO: 2. In various embodiments, the antibody may be an anti-GCGR antibody which binds to the same epitope as the antibody comprising the heavy chain variable region sequence as set forth in SEQ ID NO: 2. In various embodiments, the antibody is an anti-GCGR antibody which competes with the antibody comprising the heavy chain variable region sequence as set forth in SEQ ID NO: 2. In various embodiments, the antibody may be an anti-GCGR antibody which comprises at least one (such as two or three) CDRs of the heavy chain variable region sequence as set forth in SEQ ID NO: 2. In various embodiments, the antibody may be an anti-GCGR antibody which comprises the heavy chain variable region sequence as set forth in SEQ ID NO: 2. In various embodiments, the antibody may be an anti-GCGR antibody which comprises the heavy chain variable region sequence as set forth in SEQ ID NO: 2:

(SEQ ID NO: 2)
QVQLVESGGGVVQPGRSLRLSCAASGFTFSSYGMHWVRQAPGKGLEWVAV
MWYDGSNKDYVDSVKGRFTISRDNSKNTLYLQMNRLRAEDTAVYYCAREK
DHYDILTGYNYYYGLDVWGQGTTVTVSS

In various embodiments of the present disclosure the antibody may be an anti-GCGR antibody that has the same or higher antigen-binding affinity as that of the antibody comprising the light chain variable region sequence as set forth in SEQ ID NO: 3. In various embodiments, the antibody may be an anti-GCGR antibody which binds to the same epitope as the antibody comprising the light chain variable region sequence as set forth in SEQ ID NO: 3. In various embodiments, the antibody is an anti-GCGR antibody which competes with the antibody comprising the light chain variable region sequence as set forth in SEQ ID NO: 3. In various embodiments, the antibody may be an anti-GCGR antibody which comprises at least one (such as two or three) CDRs of the light chain variable region sequence as set forth in SEQ ID NO: 3. In various embodiments, the antibody may be an anti-GCGR antibody which comprises the light chain variable region sequence as set forth in SEQ ID NO: 3. In various embodiments, the antibody may be an anti-GCGR antibody which comprises the light chain variable region sequence as set forth in SEQ ID NO: 3:

(SEQ ID NO: 3)
DIQMTQSPSSLSASVGDRVTITCRASQGIRNDLGWYQQKPGKAPKRLIYA
ASSLQSGVPSRFSGSGSGTEFTLTISSVQPEDFVTYYCLQHNSNPLTFGG
GTKVEIK

In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with the sequences of SEQ ID NOS: 2 or 3.

In various embodiments of the present disclosure the antibody may be an anti-GCGR antibody that has the same or higher antigen-binding affinity as that of the antibody comprising the heavy chain variable region sequence as set forth in SEQ ID NO: 4. In various embodiments, the antibody may be an anti-GCGR antibody which binds to the same epitope as the antibody comprising the heavy chain variable region sequence as set forth in SEQ ID NO: 4. In various embodiments, the antibody is an anti-GCGR antibody which competes with the antibody comprising the heavy chain variable region sequence as set forth in SEQ ID NO: 4. In various embodiments, the antibody may be an anti-GCGR antibody which comprises at least one (such as two or three) CDRs of the heavy chain variable region sequence as set forth in SEQ ID NO: 4. In various embodiments, the antibody may be an anti-GCGR antibody which comprises the heavy chain variable region sequence as set forth in SEQ ID NO: 4. In various embodiments, the antibody may be an anti-GCGR antibody which comprises the heavy chain variable region sequence as set forth in SEQ ID NO: 4:

(SEQ ID NO: 4)
QVQLVESGGGVVQPGRSLRLSCAASGFTFSSYGMHWVRQAPGKGLEWV
AVMWYDGSNKDYVDSVKGRFTISRDNSKNTLYLQMNSLRAEDTAVYYCA
REKDHYDILTGYNYYYGLDVWGQGTTVTVSS

In various embodiments of the present disclosure the antibody may be an anti-GCGR antibody that has the same or higher antigen-binding affinity as that of the antibody comprising the light chain variable region sequence as set forth in SEQ ID NO: 5. In various embodiments, the antibody may be an anti-GCGR antibody which binds to the same epitope as the antibody comprising the light chain variable region sequence as set forth in SEQ ID NO: 5. In various embodiments, the antibody is an anti-GCGR antibody which competes with the antibody comprising the light chain variable region sequence as set forth in SEQ ID NO: 5. In various embodiments, the antibody may be an anti-GCGR antibody which comprises at least one (such as two or three) CDRs of the light chain variable region sequence as set forth in SEQ ID NO: 5. In various embodiments, the antibody may be an anti-GCGR antibody which comprises the light chain variable region sequence as set forth in SEQ ID NO: 5. In various embodiments, the antibody may be an anti-GCGR antibody which comprises the light chain variable region sequence as set forth in SEQ ID NO: 5:

(SEQ ID NO: 5)
DIQMTQSPSSLSASVGDRVTITCRASQGIRNDLGWYQQKPGKAPKRLIYA
ASSLQSGVPSRFSGSGSGTEFTLTISSLQPEDFVTYYCLQHNSNPLTFGG
GTKVEIK

In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with the sequences of SEQ ID NOS: 4 or 5.

In various embodiments of the present disclosure the antibody may be an anti-GCGR antibody that has the same or higher antigen-binding affinity as that of the antibody comprising the heavy chain variable region sequence as set forth in SEQ ID NO: 6. In various embodiments, the antibody may be an anti-GCGR antibody which binds to the same epitope as the antibody comprising the heavy chain variable region sequence as set forth in SEQ ID NO: 6. In various embodiments, the antibody is an anti-GCGR antibody which competes with the antibody comprising the heavy chain variable region sequence as set forth in SEQ ID NO: 6. In various embodiments, the antibody may be an anti-GCGR antibody which comprises at least one (such as two or three) CDRs of the heavy chain variable region sequence as set forth in SEQ ID NO: 6. In various embodiments, the antibody may be an anti-GCGR antibody which comprises the heavy chain variable region sequence as set forth in SEQ ID NO: 6. In various embodiments, the antibody may be an anti-GCGR antibody which comprises the heavy chain variable region sequence as set forth in SEQ ID NO: 6:

(SEQ ID NO: 6)
QVQLVESGGGVVQPGRSLRLSCAASGFTFSSYGMHWVRQAPGKGLEWVA
VMWYDGSNKDYVDSVKGRFTISRDNSKNTLYLQMNRLRAEDTAVYYCAR
EKDHYDILTGYNYYYGLDVWGQGTTVTVSS

In various embodiments of the present disclosure the antibody may be an anti-GCGR antibody that has the same or higher antigen-binding affinity as that of the antibody comprising the light chain variable region sequence as set forth in SEQ ID NO: 7. In various embodiments, the antibody may be an anti-GCGR antibody which binds to the same epitope as the antibody comprising the light chain variable region sequence as set forth in SEQ ID NO: 7. In various embodiments, the antibody is an anti-GCGR antibody which competes with the antibody comprising the light chain variable region sequence as set forth in SEQ ID NO: 7. In various embodiments, the antibody may be an anti-GCGR antibody which comprises at least one (such as two or three) CDRs of the light chain variable region sequence as set forth in SEQ ID NO: 7. In various embodiments, the antibody may be an anti-GCGR antibody which comprises the light chain variable region sequence as set forth in SEQ ID NO: 7. In various embodiments, the antibody may be an anti-GCGR antibody which comprises the light chain variable region sequence as set forth in SEQ ID NO: 7:

```
                                          (SEQ ID NO: 7)
DIQMTQSPSSLSASVGDRVTITCRASQGIRNDLGWYQQKPGKAPKRLIYAA
SSLESGVPSRFSGSGSGTEFTLTISSVQPEDFVTYYCLQHNSNPLTFGGGT
KVEIK
```

In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with the sequences of SEQ ID NOS: 6 or 7.

In various embodiments of the present disclosure the antibody may be an anti-GCGR antibody that has the same or higher antigen-binding affinity as that of the chimeric antibody comprising the heavy chain sequence as set forth in SEQ ID NO: 8. In various embodiments, the antibody may be an anti-GCGR antibody which binds to the same epitope as the antibody comprising the heavy chain sequence as set forth in SEQ ID NO: 8. In various embodiments, the antibody is an anti-GCGR antibody which competes with the antibody comprising the heavy chain sequence as set forth in SEQ ID NO: 8. In various embodiments, the antibody may be an anti-GCGR antibody which comprises at least one (such as two or three) CDRs of the heavy chain sequence as set forth in SEQ ID NO: 8. In various embodiments, the antibody may be an anti-GCGR antibody which comprises the heavy chain sequence as set forth in SEQ ID NO: 8. In various embodiments, the antibody may be an anti-GCGR antibody which comprises the heavy chain sequence as set forth in SEQ ID NO: 8:

```
                                          (SEQ ID NO: 8)
MEFGLSWVFLVALLRGVQCQVQLVESGGGVVQPGRSLRLSCAASGFTFSS

YGMHWVRQAPGKGLEWVAVMWYDGSNKDYVDSVKGRFTISRDNSKNTLYL

QMNRLRAEDTAVYYCAREKDHYDILTGYNYYYGLDVWGQGTTVTVSSAKT

TPPSVYPLAPGSAAQTNSMVTLGCLVKGYFPEPVTVIWNSGSLSSGVHTF

PAVLQSDLYTLSSSVTVPSSTWPSETVTCNVAHPASSTKVDKKIVPRDCG

CKPCICTVPEVSSVFIFPPKPKDVLTITLTPKVTCVVVDISKDDPEVQFS

WFVDDVEVHTAQTQPREEQFNSTFRSVSELPIMHQDWLNGKEFKCRVNSA

AFPAPIEKTISKTKGRPKAPQVYTIPPPKEQMAKDKVSLTCMITDFFPED

ITVEWQWNGQPAENYKNTQPIMDTDGSYFVYSKLNVQKSNWEAGNTFTCS

VLHEGLHNHHTEKSLSHSPGK
```

In various embodiments of the present disclosure the antibody may be an anti-GCGR antibody that has the same or higher antigen-binding affinity as that of the chimeric antibody comprising the light chain sequence as set forth in SEQ ID NO: 9. In various embodiments, the antibody may be an anti-GCGR antibody which binds to the same epitope as the antibody comprising the light chain sequence as set forth in SEQ ID NO: 9. In various embodiments, the antibody is an anti-GCGR antibody which competes with the antibody comprising the light chain sequence as set forth in SEQ ID NO: 9. In various embodiments, the antibody may be an anti-GCGR antibody which comprises at least one (such as two or three) CDRs of the light chain sequence as set forth in SEQ ID NO: 9. In various embodiments, the antibody may be an anti-GCGR antibody which comprises the light chain sequence as set forth in SEQ ID NO: 9. In various embodiments, the antibody may be an anti-GCGR antibody which comprises the light chain sequence as set forth in SEQ ID NO: 9:

```
                                          (SEQ ID NO: 9)
MDMRVPAQLLGLLLLWFPGARCDIQMTQSPSSLSASVGDRVTITCRASQG

IRNDLGWYQQKPGKAPKRLIYAASSLESGVPSRFSGSGSGTEFTLTISSV

QPEDFVTYYCLQHNSNPLTFGGGTKVEIKRADAAPTVSIFPPSSEQLTSG

GASVVCFLNNFYPKDINVKWKIDGSERQNGVLNSWTDQDSKDSTYSMSST

LTLTKDEYERHNSYTCEATHKTSTSPIVKSFNRNEC
```

In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with the sequences of SEQ ID NOS: 8 or 9.

In various embodiments of the present disclosure the antibody may be an anti-GCGR antibody which comprises a heavy chain variable region sequence selected from SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28, and a light chain variable region sequence selected from, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, and SEQ ID NO: 47. In various embodiments, the antibody contains an amino acid sequence that shares an observed homology of, e.g., at least 70%, at least 75%, at least 80%, at least 85%, at least 90%, at least 91%, at least 92%, at least 93%, at least 94%, at least 95%, at least 96%, at least 97%, at least 98%, or at least 99% with the sequences of SEQ ID NOS: 10-28 or SEQ ID NOS: 29-47.

Examples of Anti-GCGR Antibodies

| HCVR | LCVR |
| --- | --- |
| SEQ ID NO: 2 | SEQ ID NO: 3 |
| SEQ ID NO: 4 | SEQ ID NO: 5 |
| SEQ ID NO: 6 | SEQ ID NO: 7 |
| SEQ ID NO: 10 | SEQ ID NO: 29 |
| SEQ ID NO: 11 | SEQ ID NO: 30 |
| SEQ ID NO: 12 | SEQ ID NO: 31 |

| HCVR | LCVR |
|---|---|
| SEQ ID NO: 13 | SEQ ID NO: 32 |
| SEQ ID NO: 14 | SEQ ID NO: 33 |
| SEQ ID NO: 15 | SEQ ID NO: 34 |
| SEQ ID NO: 16 | SEQ ID NO: 35 |
| SEQ ID NO: 17 | SEQ ID NO: 36 |
| SEQ ID NO: 18 | SEQ ID NO: 37 |
| SEQ ID NO: 19 | SEQ ID NO: 38 |
| SEQ ID NO: 20 | SEQ ID NO: 39 |
| SEQ ID NO: 21 | SEQ ID NO: 40 |
| SEQ ID NO: 22 | SEQ ID NO: 41 |
| SEQ ID NO: 23 | SEQ ID NO: 42 |
| SEQ ID NO: 24 | SEQ ID NO: 43 |
| SEQ ID NO: 25 | SEQ ID NO: 44 |
| SEQ ID NO: 26 | SEQ ID NO: 45 |
| SEQ ID NO: 27 | SEQ ID NO: 46 |
| SEQ ID NO: 28 | SEQ ID NO: 47 |

In various embodiments, the isolated antagonistic antibody is a fully human antibody which comprises the amino acid sequence encoding the heavy chain variable region of SEQ ID NO: 28 and the amino acid sequence encoding the light chain variable region of SEQ ID NO: 47.

An isolated anti-GCGR antibody, antibody fragment, or antibody derivative of the present disclosure can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In various embodiments, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lanitto et al., Methods Mol. Biol. 178:303-16 (2002).

In various embodiments, an isolated antigen binding protein of the present disclosure comprises the constant light chain kappa region as set forth in SEQ ID NO: 48, or a fragment thereof. In various embodiments, an isolated antigen binding protein of the present disclosure comprises the constant light chain lambda region as set forth in SEQ ID NO: 49, or a fragment thereof. In various embodiments, an isolated antigen binding protein of the present disclosure comprises a IgG2 heavy chain constant region set forth in SEQ ID NO: 50, or a fragment thereof.

In various embodiments, an isolated antagonistic antigen binding protein of the present disclosure is a fully human anti-GCGR antibody that comprises a heavy chain sequence as set forth in SEQ ID NO: 51 and a light chain as set forth in SEQ ID NO: 52.

In various embodiments of the present disclosure, the isolated antagonistic antigen binding protein is a hemibody.

A "hemibody" is an immunologically-functional immunoglobulin construct comprising a complete heavy chain, a complete light chain and a second heavy chain Fc region paired with the Fc region of the complete heavy chain. A linker can, but need not, be employed to join the heavy chain Fc region and the second heavy chain Fc region. In various embodiments, the hemibody is a monovalent antigen binding protein comprising (i) an intact light chain, and (ii) a heavy chain fused to an Fc region (e.g., an IgG2 Fc region). Methods for preparing hemibodies are described in, e.g., U.S. patent application 2012/0195879, herein incorporated by reference in its entirety herein for purposes of teaching the preparation of such hemibodies.

Pharmaceutical Compositions

In another aspect, the present disclosure provides a pharmaceutical composition comprising an isolated antagonistic antigen binding protein as described herein, with one or more pharmaceutically acceptable carrier(s). The pharmaceutical compositions and methods of uses described herein also encompass embodiments of combinations (co-administration) with other active agents, as detailed below.

Generally, the antagonistic antigen binding proteins of the present disclosure are suitable to be administered as a formulation in association with one or more pharmaceutically acceptable carrier(s). The term 'carrier' is used herein to describe any ingredient other than the compound(s) of the disclosure. The choice of carrier(s) will to a large extent depend on factors such as the particular mode of administration, the effect of the carrier on solubility and stability, and the nature of the dosage form. As used herein, "pharmaceutically acceptable carrier" includes any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, the composition will include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody. Pharmaceutical compositions of the present disclosure and methods for their preparation will be readily apparent to those skilled in the art. Such compositions and methods for their preparation may be found, for example, in Remington's Pharmaceutical Sciences, 19th Edition (Mack Publishing Company, 1995). The pharmaceutical compositions are generally formulated as sterile, substantially isotonic and in full compliance with all GMP regulations of the U.S. Food and Drug Administration.

The pharmaceutical compositions of the present disclosure are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous injection, intraperitoneal injection, intramuscular injection, intrasternal injection, intravenous injection, intraarterial injection, intrathecal injection, intraventricular injection, intraurethral injection, intracranial injection, intrasynovial injection or infusions; or kidney dialytic infusion techniques.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded. Numerous reusable pen and autoinjector delivery devices have applications in the subcutaneous delivery of a pharmaceutical composition of the present disclosure including, but not limited to AUTOPEN™ (Owen Mumford, Inc., Woodstock, UK), DISETRONIC™ (Disetronic Medical Systems, Burghdorf, Switzerland), and HUMALOG MIX 75/25™, HUMALOG™ pen, HUMALIN 70/30™ pen (Eli Lilly and Co., Indianapolis, Ind.).

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain carriers such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the isolated antagonistic antigen binding protein in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation such as vacuum drying and freeze-drying yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin. In various embodiments, the injectable compositions will be administered using commercially available disposable injectable devices.

The isolated antagonistic antigen binding protein of the present disclosure can be administered intranasally or by inhalation, typically in the form of a dry powder (either alone, as a mixture, or as a mixed component particle, for example, mixed with a suitable pharmaceutically acceptable carrier) from a dry powder inhaler, as an aerosol spray from a pressurized container, pump, spray, atomiser (preferably an atomiser using electrohydrodynamics to produce a fine mist), or nebulizer, with or without the use of a suitable propellant, or as nasal drops.

The pressurized container, pump, spray, atomizer, or nebulizer generally contains a solution or suspension of an isolated antagonistic antigen binding protein of the disclosure comprising, for example, a suitable agent for dispersing, solubilizing, or extending release of the active, a propellant(s) as solvent.

Prior to use in a dry powder or suspension formulation, the drug product is generally micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the isolated antagonistic antigen binding protein of the disclosure, a suitable powder base and a performance modifier.

Suitable flavours, such as menthol and levomenthol, or sweeteners, such as saccharin or saccharin sodium, may be added to those formulations of the disclosure intended for inhaled/intranasal administration.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the disclosure are typically arranged to administer a metered dose or "puff" of an antibody of the disclosure. The overall daily dose will typically be administered in a single dose or, more usually, as divided doses throughout the day.

The isolated antagonistic antigen binding protein of the present disclosure may also be formulated for an oral administration. Oral administration may involve swallowing, so that the compound enters the gastrointestinal tract, and/or buccal, lingual, or sublingual administration by which the compound enters the blood stream directly from the mouth. Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Pharmaceutical compositions intended for oral use may be prepared according to any method known to the art for the manufacture of pharmaceutical compositions and such compositions may contain one or more agents selected from the group consisting of sweetening agents in order to provide a pharmaceutically elegant and palatable preparation. For example, to prepare orally deliverable tablets, the isolated antagonistic antigen binding protein is mixed with at least one pharmaceutical carrier, and the solid formulation is compressed to form a tablet according to known methods, for delivery to the gastrointestinal tract. The tablet composition is typically formulated with additives, e.g. a saccharide or cellulose carrier, a binder such as starch paste or methyl cellulose, a filler, a disintegrator, or other additives typically usually used in the manufacture of medical preparations. To prepare orally deliverable capsules, DHEA is mixed with at least one pharmaceutical carrier, and the solid formulation is placed in a capsular container suitable for delivery to the gastrointestinal tract. Compositions comprising isolated antagonistic antigen binding protein may be prepared as described generally in Remington's Pharmaceutical Sciences, 18th Ed. 1990 (Mack Publishing Co. Easton Pa. 18042) at Chapter 89, which is herein incorporated by reference.

In various embodiments, the pharmaceutical compositions are formulated as orally deliverable tablets containing isolated antagonistic antigen binding protein in admixture with non-toxic pharmaceutically acceptable carriers which are suitable for manufacture of tablets. These carriers may be inert diluents, such as calcium carbonate, sodium carbonate, lactose, calcium phosphate or sodium phosphate; granulating and disintegrating agents, for example, maize starch, gelatin or acacia, and lubricating agents, for example, magnesium stearate, stearic acid, or talc. The tablets may be uncoated or they may be coated with known techniques to delay disintegration and absorption in the gastrointestinal track and thereby provide a sustained action over a longer period of time. For example, a time delay material such as glyceryl monostearate or glyceryl distearate alone or with a wax may be employed.

In various embodiments, the pharmaceutical compositions are formulated as hard gelatin capsules wherein the isolated antagonistic antigen binding protein is mixed with an inert solid diluent, for example, calcium carbonate, calcium phosphate, or kaolin or as soft gelatin capsules wherein the isolated antagonistic antigen binding protein is mixed with an aqueous or an oil medium, for example, arachis oil, peanut oil, liquid paraffin or olive oil.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Any method for administering peptides, proteins or antibodies accepted in the art may suitably be employed for administering the isolated antagonistic antigen binding protein of the disclosure.

Methods of Treatment

Due to their interaction with the glucagon receptor, the present antigen binding and antagonizing proteins are useful for lowering blood glucose levels by regulating gluconeogenesis and glycogenlysis and also for the treatment of a wide range of conditions and disorders in which blocking the interaction of glucagon with its receptor is beneficial, while also reducing and or eliminating one or more of the unwanted side effects associated with the current treatments.

In one aspect of the present disclosure, a method for treating a subject diagnosed with a disorder or condition characterized by excessive levels of glucagon (hyperglu-conemia) and/or blood glucose comprising administering to the subject a therapeutically effective amount of an isolated antagonistic antigen binding protein that specifically binds to the human glucagon receptor, is provided. In various embodiments, the antigen binding and antagonizing proteins are fully human monoclonal antibodies and the disorder is obesity. In various embodiments, the antigen binding and antagonizing proteins are fully human monoclonal antibodies and the disorder is NAFLD. In various embodiments, the antigen binding and antagonizing proteins are fully human monoclonal antibodies and the disorder is NASH.

An antagonistic antigen binding protein, in particular a human antibody according to the present disclosure, need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the disclosure is directed to a method comprising administering to a subject an isolated antagonistic antigen binding protein such as a human antibody in an amount and for a time sufficient to induce a sustained improvement over baseline of an indicator that reflects the severity of the particular disorder.

In various embodiments of the present disclosure, obesity is defined as BMI of 30 $kg/m^2$ or more (National Institute of Health, Clinical Guidelines on the Identification, Evaluation, and Treatment of Overweight and Obesity in Adults (1998)). In various other embodiments, the present disclosure is also intended to include a disease, disorder, or condition that is characterized by a body mass index (BMI) of 25 $kg/m^2$ or more, 26 $kg/m^2$ or more, 27 $kg/m^2$ or more, 28 $kg/m^2$ or more, 29 $kg/m^2$ or more, 29.5 $kg/m^2$ or more, or 29.9 $kg/m^2$ or more, all of which are typically referred to as overweight.

An isolated antagonistic antigen binding protein that specifically binds the human glucagon receptor, in particular, the fully human antibodies of the disclosure, may be administered, e.g., once or more than once, at regular intervals over a period of time. In various embodiments, a fully human antibody is administered over a period of at least once a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the fully human antibody is administered until the subject manifests a medically relevant degree of improvement over baseline for the chosen indicator or indicators.

One example of therapeutic regimens provided herein comprise subcutaneous injection of an isolated antagonistic antigen binding protein once a week, or once every two weeks, at an appropriate dosage, to treat a condition in which blood glucose levels play a role. Weekly or monthly administration of isolated antagonistic antigen binding protein would be continued until a desired result is achieved, e.g., the subject's symptoms subside. Treatment may resume as needed, or, alternatively, maintenance doses may be administered.

A subject's levels of blood glucose may be monitored before, during and/or after treatment with an isolated antagonistic antigen binding protein such as a human antibody, to detect changes, if any, in their levels. For some disorders, the incidence of elevated blood glucose may vary according to such factors as the stage of the disease. Known techniques may be employed for measuring glucose levels. Glucagon levels may also be measured in the subject's blood using known techniques, for example, ELISA.

A therapeutically effective dose can be estimated initially from cell culture assays by determining an $IC_{50}$. A dose can then be formulated in animal models to achieve a circulating plasma concentration range that includes the $IC_{50}$ as determined in cell culture. Such information can be used to more accurately determine useful doses in humans. Levels in plasma may be measured by, e.g., HPLC or immunoassays using the anti-idiotypic antibodies specific to the therapeutic drug. The exact composition, route of administration and dosage can be chosen by the individual physician in view of the subject's condition.

Dosage regimens can be adjusted to provide the optimum desired response (e.g., a therapeutic or prophylactic response). For example, a single bolus can be administered, several divided doses (multiple or repeat or maintenance) can be administered over time and the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present disclosure will be dictated primarily by the unique characteristics of the antibody and the particular therapeutic or prophylactic effect to be achieved.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present disclosure.

It is to be noted that dosage values may vary with the type and severity of the condition to be ameliorated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this disclosure may be based on a variety of factors, including the type of disease, the age, weight, sex, medical condition of the subject, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-subject dose-escalation as determined by the skilled artisan. Determining appropriate dosages and regimens are well-known in the relevant art and would be understood to be encompassed by the skilled artisan once provided the teachings disclosed herein.

For administration to human patients, the total monthly dose of the isolated antagonistic antigen binding protein of the disclosure can be in the range of 0.5-1200 mg per patient, 0.5-1100 mg per patient, 0.5-1000 mg per patient, 0.5-900 mg per patient, 0.5-800 mg per patient, 0.5-700 mg per patient, 0.5-600 mg per patient, 0.5-500 mg per patient, 0.5-400 mg per patient, 0.5-300 mg per patient, 0.5-200 mg per patient, 0.5-100 mg per patient, 0.5-50 mg per patient, 1-1200 mg per patient, 1-1100 mg per patient, 1-1000 mg per patient, 1-900 mg per patient, 1-800 mg per patient, 1-700 mg per patient, 1-600 mg per patient, 1-500 mg per patient, 1-400 mg per patient, 1-300 mg per patient, 1-200 mg per patient, 1-100 mg per patient, or 1-50 mg per patient depending, of course, on the mode of administration. For example, an intravenous monthly dose can require about 1-1000 mg/patient. In various embodiments, the isolated antagonistic antigen binding protein of the disclosure can be administered at an intravenous monthly dose of about 1-500 mg per patient. In various embodiments, the isolated antagonistic antigen binding protein of the disclosure can be administered at an intravenous monthly dose of about 1-400 mg per patient. In various embodiments, the isolated antagonistic antigen binding protein of the disclosure can be administered at an intravenous monthly dose of about 1-300 mg per patient. In various embodiments, the isolated antagonistic antigen binding protein of the disclosure can be administered at an intravenous monthly dose of about 1-200 mg per patient. In various embodiments, the isolated antagonistic antigen binding protein of the disclosure can be administered, at an intravenous monthly dose of about 1-150 mg per patient. In various embodiments, the isolated antagonistic antigen binding protein of the disclosure can be administered or at an intravenous monthly dose of about 1-100 mg/patient. In various embodiments, the isolated antagonistic antigen binding protein of the disclosure can be administered at an intravenous monthly dose of about 1-50 mg per patient. The total monthly dose can be administered in single or divided doses and can, at the physician's discretion, fall outside of the typical ranges given herein.

An exemplary, non-limiting weekly, or bi-weekly dosing range for a therapeutically or prophylactically effective amount of an isolated antagonistic antigen binding protein of the disclosure can be 0.001 to 100 mg/kg body weight, 0.001 to 90 mg/kg, 0.001 to 80 mg/kg, 0.001 to 70 mg/kg, 0.001 to 60 mg/kg, 0.001 to 50 mg/kg, 0.001 to 40 mg/kg, 0.001 to 30 mg/kg, 0.001 to 20 mg/kg, 0.001 to 10 mg/kg, 0.001 to 5 mg/kg, 0.001 to 4 mg/kg, 0.001 to 3 mg/kg, 0.001 to 2 mg/kg, 0.001 to 1 mg/kg, 0.010 to 50 mg/kg, 0.010 to 40 mg/kg, 0.010 to 30 mg/kg, 0.010 to 20 mg/kg, 0.010 to 10 mg/kg, 0.010 to 5 mg/kg, 0.010 to 4 mg/kg, 0.010 to 3 mg/kg, 0.010 to 2 mg/kg, 0.010 to 1 mg/kg, 0.1 to 50 mg/kg, 0.1 to 40 mg/kg, 0.1 to 30 mg/kg, 0.1 to 20 mg/kg, 0.1 to 10 mg/kg, 0.1 to 5 mg/kg, 0.1 to 4 mg/kg, 0.1 to 3 mg/kg, 0.1 to 2 mg/kg, 0.1 to 1 mg/kg, 1 to 50 mg/kg, 1 to 40 mg/kg, 1 to 30 mg/kg, 1 to 25 mg/kg, 1 to 20 mg/kg, 1 to 15 mg/kg, 1 to 10 mg/kg, 1 to 7.5 mg/kg, 1 to 5 mg/kg, 1 to 4 mg/kg, 1 to 3 mg/kg, 1 to 2 mg/kg, or 1 mg/kg body weight. It is to be noted that dosage values may vary with the type and severity of the condition to be alleviated. It is to be further understood that for any particular patient, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In various embodiments, the total dose administered will achieve a plasma antibody concentration in the range of, e.g., about 1 to 1000 μg/ml, about 1 to 750 μg/ml, about 1 to 500 μg/ml, about 1 to 250 μg/ml, about 10 to 1000 μg/ml, about 10 to 750 μg/ml, about 10 to 500 μg/ml, about 10 to 250 μg/ml, about 20 to 1000 μg/ml, about 20 to 750 μg/ml, about 20 to 500 μg/ml, about 20 to 250 μg/ml, about 30 to 1000 μg/ml, about 30 to 750 μg/ml, about 30 to 500 μg/ml, about 30 to 250 μg/ml.

In various embodiments, either as monotherapy, or in combination with an anti-obesity agent, the weekly or bi-weekly dose for a therapeutically effective amount of an isolated antagonistic antigen binding protein of the disclosure will be 0.01 mg/kg body weight. In various embodiments, the weekly or bi-weekly dose for a therapeutically effective amount of an isolated antagonistic antigen binding protein of the disclosure will be 0.025 mg/kg body weight. In various embodiments, the weekly or bi-weekly dose for a therapeutically effective amount of an isolated antagonistic antigen binding protein of the disclosure will be 0.05 mg/kg body weight. In various embodiments, the weekly or bi-weekly dose for a therapeutically effective amount of an isolated antagonistic antigen binding protein of the disclosure will be 0.075 mg/kg body weight. In various embodiments, the weekly or bi-weekly dose for a therapeutically effective amount of an isolated antagonistic antigen binding protein of the disclosure will be 0.1 mg/kg body weight. In various embodiments, the weekly or bi-weekly dose for a therapeutically effective amount of an isolated antagonistic antigen binding protein of the disclosure will be 0.25 mg/kg body weight. In various embodiments, the weekly or bi-weekly dose for a therapeutically effective amount of an isolated antagonistic antigen binding protein of the disclosure will be 0.5 mg/kg body weight. In various embodiments, the weekly or bi-weekly dose for a therapeutically effective amount of an isolated antagonistic antigen binding protein of the disclosure will be 0.75 mg/kg body weight. In various embodiments, the weekly or bi-weekly dose for a therapeutically effective amount of an isolated antagonistic antigen binding protein of the disclosure will be 1 mg/kg body weight. In various embodiments, the weekly or bi-weekly dose for a therapeutically effective amount of an isolated antagonistic antigen binding protein of the disclosure will be 1.5 mg/kg body weight. In various embodiments, the weekly or bi-weekly dose for a therapeutically effective amount of an isolated antagonistic antigen binding protein of the disclosure will be 2 mg/kg body weight. In various embodiments, the weekly or bi-weekly dose for a therapeutically effective amount of an isolated antagonistic antigen binding protein of the disclosure will be 2.5 mg/kg body weight. In various embodiments, the weekly or bi-weekly dose for a therapeutically effective amount of an isolated antagonistic antigen binding protein of the disclosure will be 3 mg/kg body weight. In various embodiments, the weekly or bi-weekly dose for a therapeutically effective amount of an isolated antagonistic antigen binding protein of the disclosure will be 3.5 mg/kg body weight. In various embodiments, the weekly or bi-weekly dose for a therapeutically effective amount of an isolated antagonistic antigen binding protein of the disclosure will be 4 mg/kg body weight. In various embodiments, the weekly or bi-weekly dose for a therapeutically effective amount of an isolated antagonistic antigen binding protein of the disclosure will be 4.5 mg/kg body weight. In various embodiments, the weekly or bi-weekly dose for a therapeutically effective amount of an isolated antagonistic antigen binding protein of the disclosure will be 5 mg/kg body weight. In various embodiments, the weekly or bi-weekly dose for a therapeutically effective amount of an isolated antagonistic antigen binding protein of the disclosure will be 5.5 mg/kg body weight. In various embodiments, the weekly or bi-weekly dose for a therapeutically effective amount of an isolated antagonistic antigen binding protein of the disclosure will be 6 mg/kg body weight. In various embodiments, the weekly or bi-weekly dose for a therapeutically effective amount of an isolated antagonistic antigen binding protein of the disclosure will be 6.5 mg/kg body weight. In various embodiments, the weekly or bi-weekly dose for a therapeutically effective amount of an isolated antagonistic antigen binding protein of the disclosure will be 7 mg/kg body weight. In various embodiments, the weekly or bi-weekly dose for a therapeutically effective amount of an isolated antagonistic antigen binding protein of the disclosure will be 7.5 mg/kg body weight. In various embodiments, the weekly or bi-weekly dose for a therapeutically effective amount of an isolated antagonistic antigen binding protein of the disclosure will be 8 mg/kg body weight. In various embodiments, the weekly or bi-weekly dose for a therapeutically effective amount of an isolated antagonistic antigen binding protein of the disclosure will be 8.5 mg/kg body weight. In various embodiments, the weekly or bi-weekly dose for a therapeutically effective amount of an isolated antagonistic antigen binding protein of the disclosure will be 9 mg/kg body weight. In various embodiments, the weekly or bi-weekly dose for a therapeutically effective amount of an isolated antagonistic antigen binding protein of the disclosure will be 9.5 mg/kg body weight. In various embodiments, the weekly or bi-weekly dose for a therapeutically effective amount of an isolated antagonistic antigen binding protein of the disclosure will be 10 mg/kg body weight.

Toxicity and therapeutic index of the pharmaceutical compositions of the disclosure can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effective dose is the therapeutic index and it can be expressed as the ratio $LD_{50}/ED_{50}$. Compositions that exhibit large therapeutic indices are generally preferred.

In various embodiments, single or multiple administrations of the pharmaceutical compositions are administered depending on the dosage and frequency as required and tolerated by the subject. In any event, the composition should provide a sufficient quantity of at least one of the isolated antagonistic antigen binding protein disclosed herein to effectively treat the subject. The dosage can be administered once but may be applied periodically until either a therapeutic result is achieved or until side effects warrant discontinuation of therapy.

The dosing frequency of the administration of the isolated antagonistic antigen binding protein pharmaceutical composition depends on the nature of the therapy and the particular disease being treated. The subject can be treated at regular intervals, such as weekly or monthly, until a desired therapeutic result is achieved. Exemplary dosing frequencies include, but are not limited to: once weekly without break; once weekly, every other week; once every 2 weeks; once every 3 weeks; weakly without break for 2 weeks, then monthly; weakly without break for 3 weeks, then monthly; monthly; once every other month; once every three months; once every four months; once every five months; or once every six months, or yearly.

As used herein, the terms "co-administration", "co-administered" and "in combination with", referring to the isolated antagonistic antigen binding protein of the present disclosure and one or more other therapeutic agent(s), is intended to mean, and does refer to and include the following: simultaneous administration of such combination of isolated antagonistic antigen binding protein of the disclosure and therapeutic agent(s) to a subject in need of treatment, when such components are formulated together into a single dosage form which releases said components at substantially the same time to said subject; substantially simultaneous administration of such combination of isolated antagonistic antigen binding protein of the disclosure and therapeutic agent(s) to a subject in need of treatment, when such components are formulated apart from each other into separate dosage forms which are taken at substantially the same time by said subject, whereupon said components are released at substantially the same time to said subject; sequential administration of such combination of isolated antagonistic antigen binding protein of the disclosure and therapeutic agent(s) to a subject in need of treatment, when such components are formulated apart from each other into separate dosage forms which are taken at consecutive times by said subject with a significant time interval between each administration, whereupon said components are released at substantially different times to said subject; and sequential administration of such combination of isolated antagonistic antigen binding protein of the disclosure and therapeutic agent(s) to a subject in need of treatment, when such components are formulated together into a single dosage form which releases said components in a controlled manner whereupon they are concurrently, consecutively, and/or overlappingly released at the same and/or different times to said subject, where each part may be administered by either the same or a different route.

Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable anti-obesity agents (some of which may also act as anti-diabetic agents as well) include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $β_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists such as velneperit), $PYY_{3-36}$ (including analogs thereof), BRS3 modulator, mixed antagonists of opiod receptor subtypes, thyromimetic agents, dehydroepiandrosterone or an analog thereof, glucocorticoid agonists or antagonists, orexin antagonists, glucagon-like peptide-1 agonists, ciliary neurotrophic factors (such as AXOKINE™ available from Regeneron Pharmaceuticals, Inc., Tarrytown, N.Y. and Procter & Gamble Company, Cincinnati, Ohio), human agouti-related protein (AGRP) inhibitors, histamine 3 antagonists or inverse agonists, neuromedin U agonists, MTP/ApoB inhibitors (e.g., gut-selective MTP inhibitors, such as dirlotapide, JTT130, Usistapide, SLx4090), opioid antagonist, mu opioid receptor modulators, including but not limited to GSK1521498, MetAp2 inhibitors, including but not limited to ZGN-433, agents with mixed modulatory activity at 2 or more of glucagon, GIP and GLP1 receptors, such as MAR-701 or ZP2929, norepinephrine transporter inhibitors, cannabinoid-1-receptor antagonist/inverse agonists, ghrelin agonists/antagonists, oxyntomodulin and analogs, monoamine uptake inhibitors, such as but not limited to tesofensine, an orexin antagonist, combination agents (such as bupropion plus zonisamide, pramlintide plus metreleptin, bupropion plus naltrexone, phentermine plus topiramate), and the like.

In various embodiments, the anti-obesity agent is selected from gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b—tetraaza-benzo[e]azulen-6-yl]-N-isopropyl-acetamide (described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), oleoyl-estrone (CAS No. 180003-17-2), obinepitide (TM30338), pramlintide (SYMLIN™), tesofensine (NS2330), leptin, bromocriptine, orlistat, AOD-9604 (CAS No. 221231-10-3) and sibutramine.

In various embodiments, the combination therapy comprises administering the isolated antagonistic antigen binding protein composition and the second agent composition simultaneously, either in the same pharmaceutical composition or in separate pharmaceutical compositions. In various embodiments, isolated antagonistic antigen binding protein composition and the second agent composition are administered sequentially, i.e., the isolated antagonistic antigen binding protein composition is administered either prior to or after the administration of the second agent composition.

In various embodiments, the administrations of the isolated antagonistic antigen binding protein composition and the second agent composition are concurrent, i.e., the administration period of the isolated antagonistic antigen binding protein composition and the second agent composition overlap with each other.

In various embodiments, the administrations of the isolated antagonistic antigen binding protein composition and the second agent composition are non-concurrent. For example, in various embodiments, the administration of the isolated antagonistic antigen binding protein composition is terminated before the second agent composition is administered. In various embodiments, the administration second agent composition is terminated before the isolated antagonistic antigen binding protein composition is administered.

In various embodiments, the present disclosure comprises a method for treating an overweight or obese subject comprising administering to the subject a therapeutically effective amount of an isolated antagonistic antigen binding protein that specifically binds to the human glucagon receptor.

In various embodiments, the present disclosure comprises a method for treating an overweight or obese subject comprising administering to the subject: (a) a therapeutically effective amount of an isolated antagonistic antigen binding protein that specifically binds to the human glucagon receptor; and (b) an anti-obesity agent.

In various embodiments, the present disclosure comprises a method for treating or preventing NAFLD/NASH in a subject, comprising administering to a subject diagnosed with NAFLD/NASH, or a subject at risk of contracting NAFLD/NASH, a therapeutically effective amount of an isolated antagonistic antigen binding protein that specifically binds to the human glucagon receptor. In various embodiments, the antibody is a fully human monoclonal antibody. In various embodiments, the present disclosure comprises a method for treating NAFLD. In various embodiments, the present disclosure comprises a method for treating NASH.

In various embodiments, the present disclosure comprises a method for treating or preventing NAFLD/NASH in a subject, comprising administering to a subject diagnosed with NAFLD/NASH, or a subject at risk of contracting NAFLD/NASH, (a) a therapeutically effective amount of an isolated antagonistic antigen binding protein that specifically binds to the human glucagon receptor; and (b) an anti-obesity agent. In various embodiments, the antibody is a fully human monoclonal antibody. In various embodiments, the present disclosure comprises a method for treating NAFLD. In various embodiments, the present disclosure comprises a method for treating NASH.

In another aspect, the present disclosure provides methods for treating a subject who is at risk of developing NASH (e.g., subjects who are overweight or obese or subjects with NAFLD) comprising administering to the subject a therapeutically effective amount of an isolated antagonistic antigen binding protein that specifically binds to the human glucagon receptor.

In another aspect, the present disclosure relates to the use of a non-naturally occurring isolated antagonistic antigen binding protein that specifically binds to the human glucagon receptor for the preparation of a medicament for treatment, prophylaxis and/or prevention of nonalcoholic steatohepatitis (NASH) in a subject in need thereof.

In another aspect, the present disclosure relates to the use of a non-naturally occurring isolated antagonistic antigen binding protein that specifically binds to the human glucagon receptor for the preparation of a medicament for treatment, prophylaxis and/or prevention of nonalcoholic fatty liver disease (NAFLD) in a subject in need thereof.

In another aspect, the present disclosure relates to the use of a non-naturally occurring isolated antagonistic antigen binding protein that specifically binds to the human glucagon receptor for the preparation of a medicament for treatment a subject classified as obese (e.g., having a body mass index (BMI) of 30 kg/m$^2$ or more).

The invention having been described, the following examples are offered by way of illustration, and not limitation.

Example 1

In this example, the relationship between regulating glucose output and the development of obesity in various DIO murine models is evaluated. Specifically, the in vivo activity of an anti-GCGR antibody which comprises the heavy chain sequence set forth in SEQ ID NO: 8 and the light chain sequence set forth in SEQ ID NO: 9 ("REMD2.59C") is evaluated in a 20 week DIO murine model using wild-type C57BL/6 mice. Wild-type C57BL/6 mice are commonly used for obesity research, because they show increasing body fat mass, hyperglycemia, and hyperinsulinemia when they are fed a high fat diet ("HFD")(REbuffe-Scrive, M et al., Metabolism, 42:1405-1409, 1993; Surwit, R S., Metabolism 44:645-651, 1995).

In this study, three groups of 10 each wild-type C57BL/6J mice (male, age 4-6 weeks, 20-22 g) are fed ad libitum with a high fat diet (HFD) for 8 weeks (hereinafter "Vehicle Group" or "REMD2.59 Group" or "Pair Feeding Group"). One group of 10 wild-type C57BL/6J mice (male, age 4-6 weeks, 20-22 g) are fed ad libitum with normal diet ("chow") for 8 weeks (hereinafter "Normal Diet Group"). One group of 8 wild-type C57BL/6J (male, age 4-6 weeks, 20-22 g) are fed with a HFD and dosed weekly with 7.5 mg/kg REMD2.59 antibody for 8 weeks (starting on day 1) (hereinafter "Prevention Group"). The mice are kept in laminar flow rooms at constant temperature and humidity with one animal in each cage. Animals are housed in polycarbonate cages and in an environmentally monitored, well-ventilated room maintained at a temperature of (22±2° C.) and a relative humidity of 40%-70%. Fluorescent lighting provided illumination approximately 12 hours per day. The bedding material is soft wood, which is changed once per week. All procedures were conducted in accordance with the National Institutes of Health (NIH) guidelines for the care and use of laboratory animals.

At 8 weeks following the start of the HFD diet, the "Vehicle Group" and the "Pair Feeding Group" remain on HFD and the "Normal Diet Group" remains on chow and are all dosed weekly (starting on day 57 and up thru week 20) via subcutaneous injection with vehicle (PBS). The HFD "REMD2.59 Group" is dosed weekly (starting on day 57 and up thru week 20) via subcutaneous injection with 7.5 mg/kg (10 mL/kg) REMD2.59C antibody. The HFD "Prevention Group" continues to be dosed weekly up thru week 20 via subcutaneous injection with 7.5 mg/kg (10 mL/kg) REMD2.59C antibody. The Study group assignments are outlined in Table 2 below.

TABLE 2

| Group | Diet (Week-1-20) | Weekly Treatment Dose, mg/kg, | Treatment Start Date | Treatment End Date |
|---|---|---|---|---|
| Vehicle Control (N = 10) | HFD | PBS | Week-9 | Week-20 |

TABLE 2-continued

| Group | Diet (Week-1-20) | Weekly Treatment Dose, mg/kg, | Treatment Start Date | Treatment End Date |
|---|---|---|---|---|
| REMD2.59C (N = 10) | HFD | REMD2.59C, 7.5 mg/kg | Week-9 | Week-20 |
| Pair Feeding (N = 10) | HFD | PBS | Week-9 | Week-20 |
| Prevention (N = 8) | HFD | REMD2.59C, 7.5 mg/kg | Week-1 | Week-20 |
| Normal Diet (N = 10) | Normal Diet | PBS | Week-9 | Week-20 |

Body weight is measured weekly throughout the study. Food consumption (food in/food out) is recorded weekly throughout the study. Food consumption is monitored daily for the first week post treatment for the "REMD2.59 Group" and the amount on post-treatment day 7 is then used to feed the "Pair Feeding Group" during week 10. Each week thereafter, food consumption of the "REMD2.59 Group" is monitored weekly and the food consumption amount at the end of each week is used to feed the "Pair Feeding Group" the following week. The chow fed "Normal diet group" is fed the same amount of chow throughout the entire 20 week study.

In addition to body weight and food consumption, various other parameters are measured throughout the 20 week study, including, e.g., i) fasting blood glucose determination was measured via tail veins weekly using Accu-Chek Aviva System® (mice are fasted for 6 hours prior to the test and fasting blood glucose levels); ii) oral glucose tolerance test (OGTT) was performed for all animals at the end of the study to test the repeat dosing effect of REMD Ab2.59. The baseline (time 0) glucose level was measured after 16 hours fast and prior to glucose challenge. Following oral administration of 2 g/kg glucose, the blood glucose levels were measured at different time points (30, 60, 120 min) by using Accu-Chek Performa System; iii) the lipid profile in serum and blood bio-chemistry parameters (ALT, AST, GGT, ALP, TG and TCHO) were tested throughout the study. Blood samples were obtained on week 8, 12, 16 and 20, the samples were immediately processed by centrifugation at 4° C., 4000 g for 15 minutes, and then they were transferred into new test tubes. Lipid profile and blood bio-chemistry parameters were measured by using TOSHIBA TBA-40FR automated biochemical analyzer; iv) the lipid profiles (TG, TCHO, HDL-C and LDL-C) were extracted from the liver of the animal according to the protocol, and then lipid profile were measured by using TOSHIBA TBA-40FR automated biochemical analyzer; v) the insulin level of all study animals were measured on week 8, 12, 16 and 20. GLP-1 and leptin were measured at the end of the study with ELISA method. The blood serum was used for the analysis; and vi) on the termination day, after OGTT study necropsy was conducted. At the end of the study, tissue or organs were collected and the wet weights of the pancreas, white adipose tissue (WAT), muscle (gastrocnemius muscle) and liver were measured. Half of these tissue samples were fixed and brought up to paraffin block for H&E (liver and WAT) or IHC (pancreas) analysis. Hypothalamus, brain, heart and remaining part of pancreas, WAT, muscle, liver were stored at −80° C. or future analysis. The various measurements and/or analysis described above is made as described in the Additional Materials and Methods section below. All statistical tests were conducted, and the level of significance were set at 5% or $P<0.05$. The group means and standard deviation were calculated for all measurement parameters as study designed. A one-way analysis of variance (ANOVA) was used among the groups with software Graph Pad Prism 5.0.

Results

Body Weight and Food Consumption—

Figure 2:
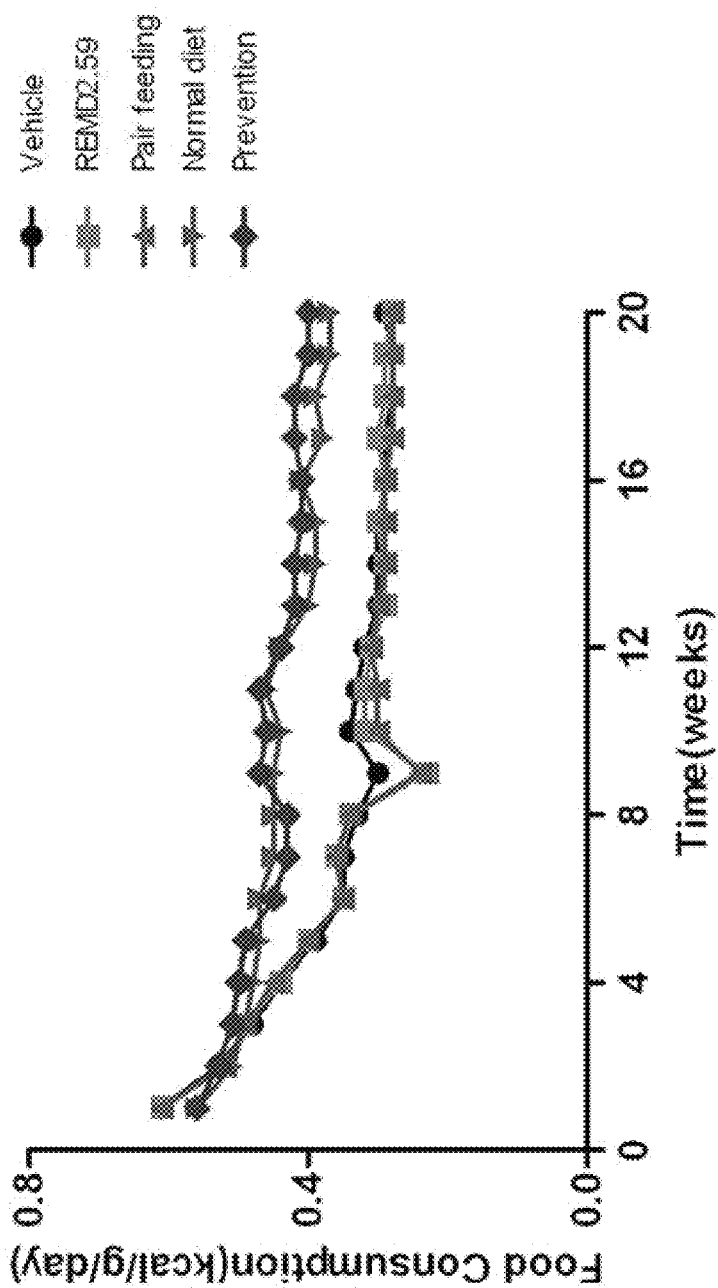
FIG. 2 is a line plot depicting the in vivo effects on food consumption (kcal/g/day) for the Vehicle group, REMD2.59 group, Pair feeding group, Normal diet group, and Prevention group as described herein, in a HFD DIO mouse study, evaluated for up to twenty weeks. Treatment commenced on Day 57 (i.e., start of week 9) for all groups but the Prevention group. For the Prevention group, REMD2.59C antibody was administered weekly starting from day 1 of HFD feeding.

As depicted in FIG. 1, the REMD2.59 Group efficiently reduced weight gain from Week 9 to Week 20. The Pair Feeding Group, which was given the same amount of daily food as that of the REMD2.59 Group from Week 9 to Week 20, showed a similar, but slightly greater weight gain, than the REMD2.59 Group. This observation suggests that the effects of REMD2.59 are not limited to the reduction in food intake. The Prevention Group, which received REMD2.59 weekly injections concurrently with HFD from Week 1 through Week 20, showed the lowest weight gain compared with all other groups, despite the HFD feeding. Specifically, the average body weight of the Prevention Group (35.3±3.0 g) was 34% lower (P<0.01) than the Vehicle Group (53.3±2.4 g), and 9% lower even than the Normal Diet Group (38.6±3.1 g), at the end of the study (on Day 140, or end of Week-20). As depicted in FIG. 2, the Prevention Group consumed the same amount of calories per gram of body weight as the Normal Diet Group. On the other hand, the HFD fed groups (Vehicle Group, REMD2.59 Group and Pair Feeding Group) all consumed nearly the same amount of calories when adjusted by gram of body weight. Nevertheless, taking into consideration of the body weight differences, the Vehicle Group still consumes greater amount of calories per animal, than the REMD2.59 Group and Pair Feeding Groups, since the Vehicle Group has the highest average body weight.

Fasting Blood Glucose—

Figure 3:
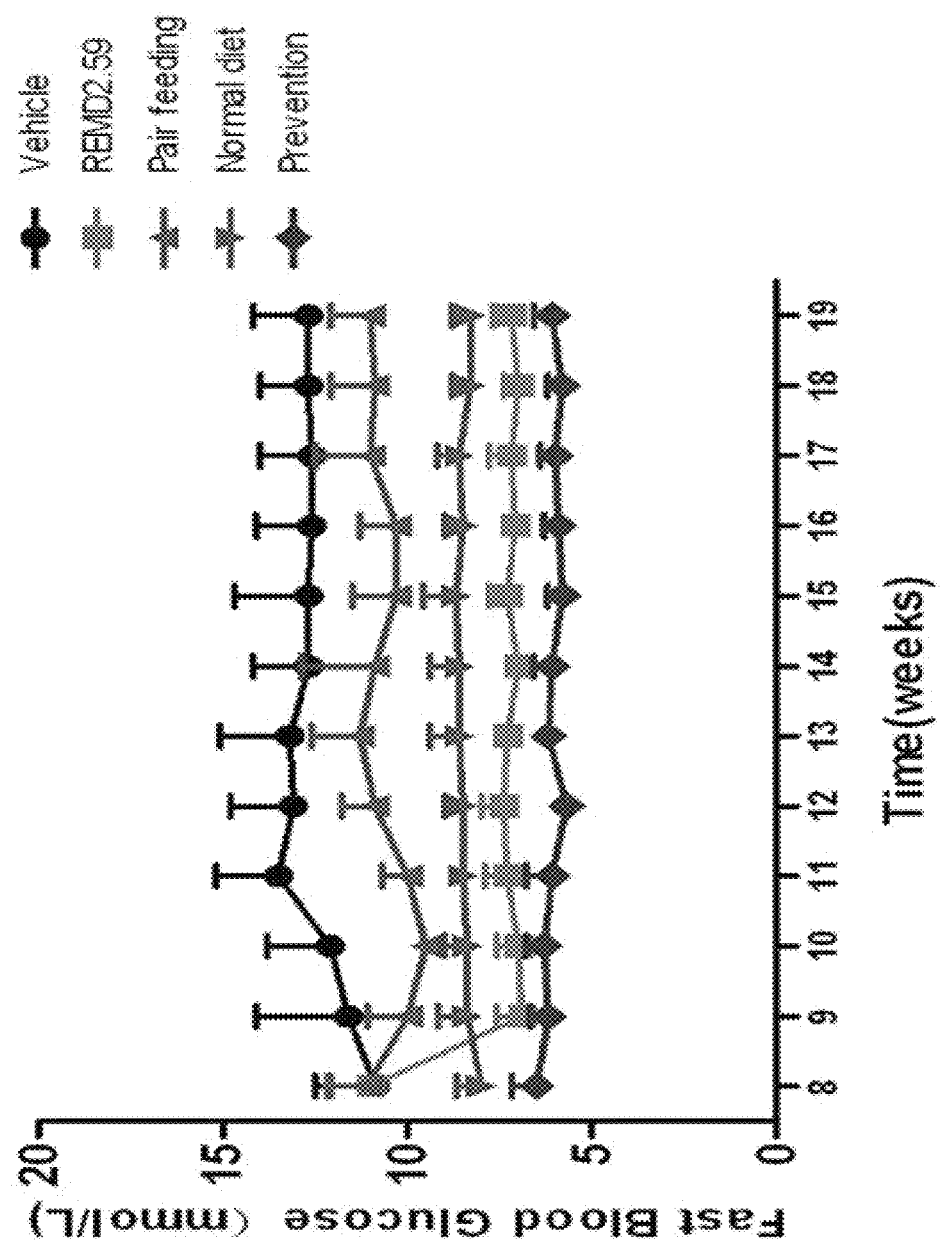
FIG. 3 is a line plot depicting the in vivo effects on blood glucose (mmol/L) for the Vehicle group, REMD2.59 group, Pair feeding group, Normal diet group, and Prevention group as described herein, in a HFD DIO mouse study, evaluated for up to 19 weeks. Treatment commenced on Day 57 (i.e., start of week 9) for all groups but the Prevention group. For the Prevention group, REMD2.59C antibody was administered weekly starting from day 1 of HFD feeding.

As depicted in FIG. 3, REMD2.59 treatment initiated from Week 9 (i.e., the REMD2.59 Group) resulted in markedly lower blood glucose levels than the Vehicle Control Group. This correction of hyperglycemia cannot be explained by the reduced energy consumption alone, since the Pair Feeding Group achieved a much smaller magnitude of glucose lowering than the REMD2.59 Group. The Prevention Group led to the lowest fasting plasma glucose profiles, even lower than the Normal Diet Control Group. Finally, diet-induced obesity is clearly associated with hyperglycemia, as evidenced by the Vehicle Control Group.

Blood Glucose Levels from Oral Glucose Tolerance Test (OGTT)—

Figure 4:
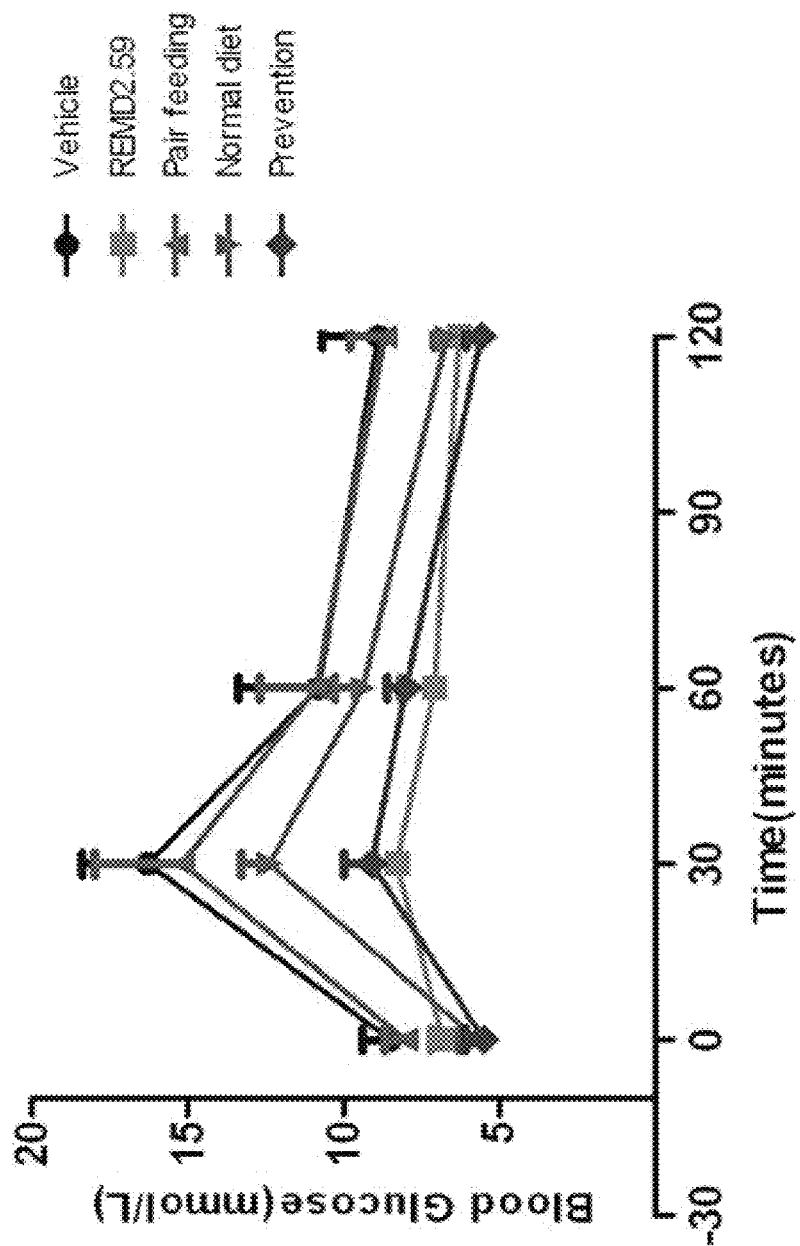
FIG. 4 is a line plot depicting the in vivo effects of repeat dosing of REMD 2.59 on blood glucose (mmol/L) for the Vehicle group, REMD2.59 group, Pair feeding group, Normal diet group, and Prevention group as described herein, in a HFD DIO mouse study, evaluated at week 20. Treatment commenced on Day 57 (i.e., start of week 9) for all groups but the Prevention group. For the Prevention group, REMD2.59C antibody was administered weekly starting from day 1 of HFD feeding. The oral glucose tolerance test (OGTT) was performed for all animals at the end of the study (i.e., week 20).
Figure 5:
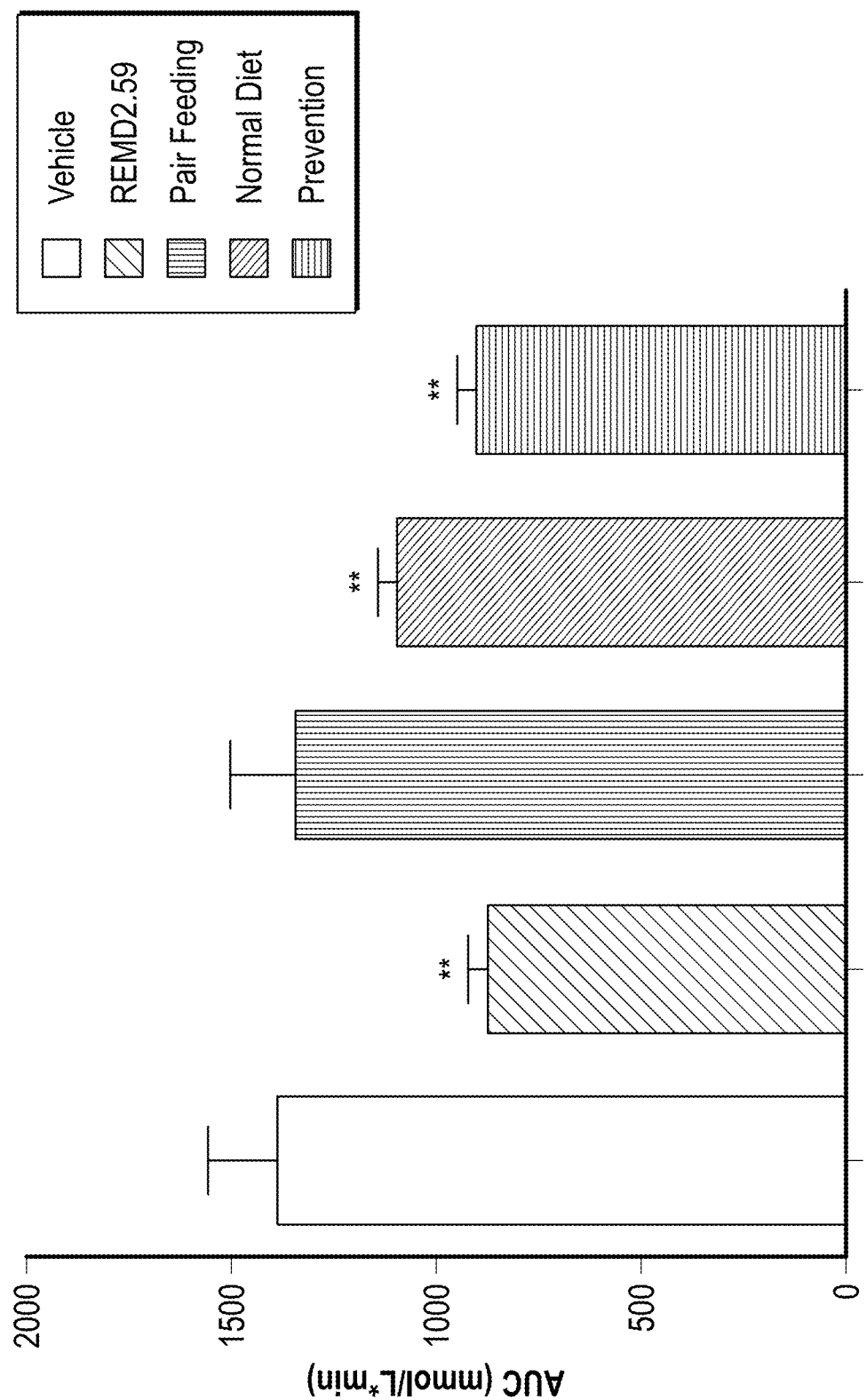
FIG. 5 is a bar graph depicting the AUC levels (mmol/L min blood glucose) for the Vehicle group, REMD2.59 group, Pair feeding group, Normal diet group, and Prevention group as described herein, in a HFD DIO mouse study, evaluated at week 20. Treatment commenced on Day 57 (i.e., start of week 9) for all groups but the Prevention group. For the Prevention group, REMD2.59C antibody was administered weekly starting from day 1 of HFD feeding.

As depicted in FIG. 4, REMD 2.59, given either as treatment (REMD2.59 Group) or as a preventive measure (Prevention Group), resulted in markedly lower blood glucose profiles during an oral glucose tolerance test (OGTT). However, the untreated (Vehicle Group) or food-restricted (Pair-Fed Group) displayed a diabetic OGTT glucose profile, featuring elevated baseline glucose levels and higher glucose excursions during the OGTT, and ending in higher post-OGTT glucose profiles. As depicted in FIG. 5, the OGTT glucose area under the curve (AUC) values appear to confirm the observations, and support the observations depicted in FIG. 4.

Lipid Profile and Blood Biochemistry Data—

Figure 6:
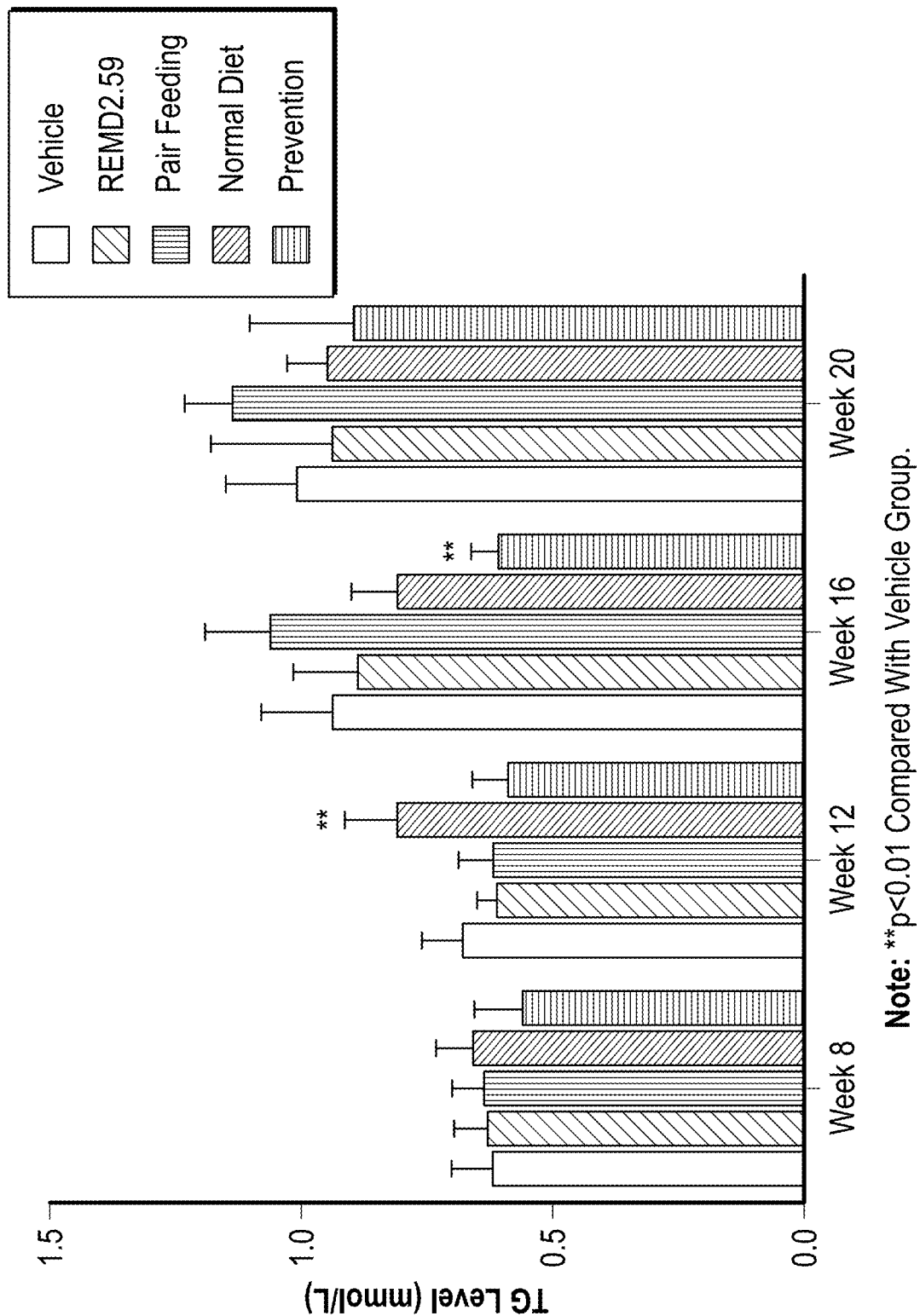
FIG. 6 is a bar graph depicting the in vivo effects on triglyceride (TG) levels (mmol/L) in serum for the Vehicle group, REMD2.59 group, Pair feeding group, Normal diet group, and Prevention group as described herein, in a HFD DIO mouse study, evaluated for 20 weeks. Treatment commenced on Day 57 (i.e., start of week 9) for all groups but the Prevention group. For the Prevention group, REMD2.59C antibody was administered weekly starting from day 1 of HFD feeding.
Figure 7:
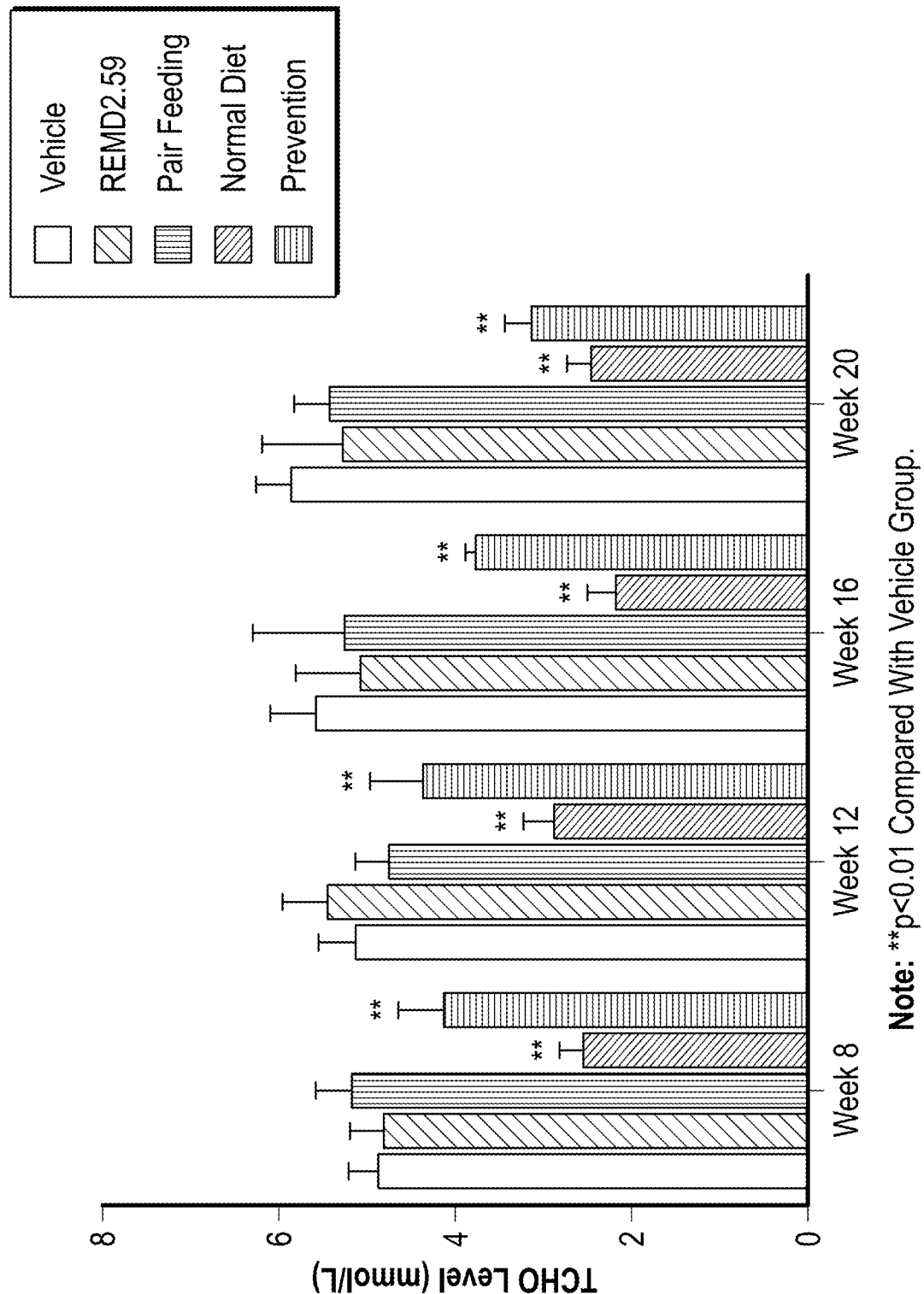
FIG. 7 is a bar graph depicting the in vivo effects on total cholesterol (TCHO) levels (mmol/L) in serum for the Vehicle group, REMD2.59 group, Pair feeding group, Normal diet group, and Prevention group as described herein, in a HFD DIO mouse study, evaluated for 20 weeks. Treatment commenced on Day 57 (i.e., start of week 9) for all groups but the Prevention group. For the Prevention group, REMD2.59C antibody was administered weekly starting from day 1 of HFD feeding.
Figure 8:
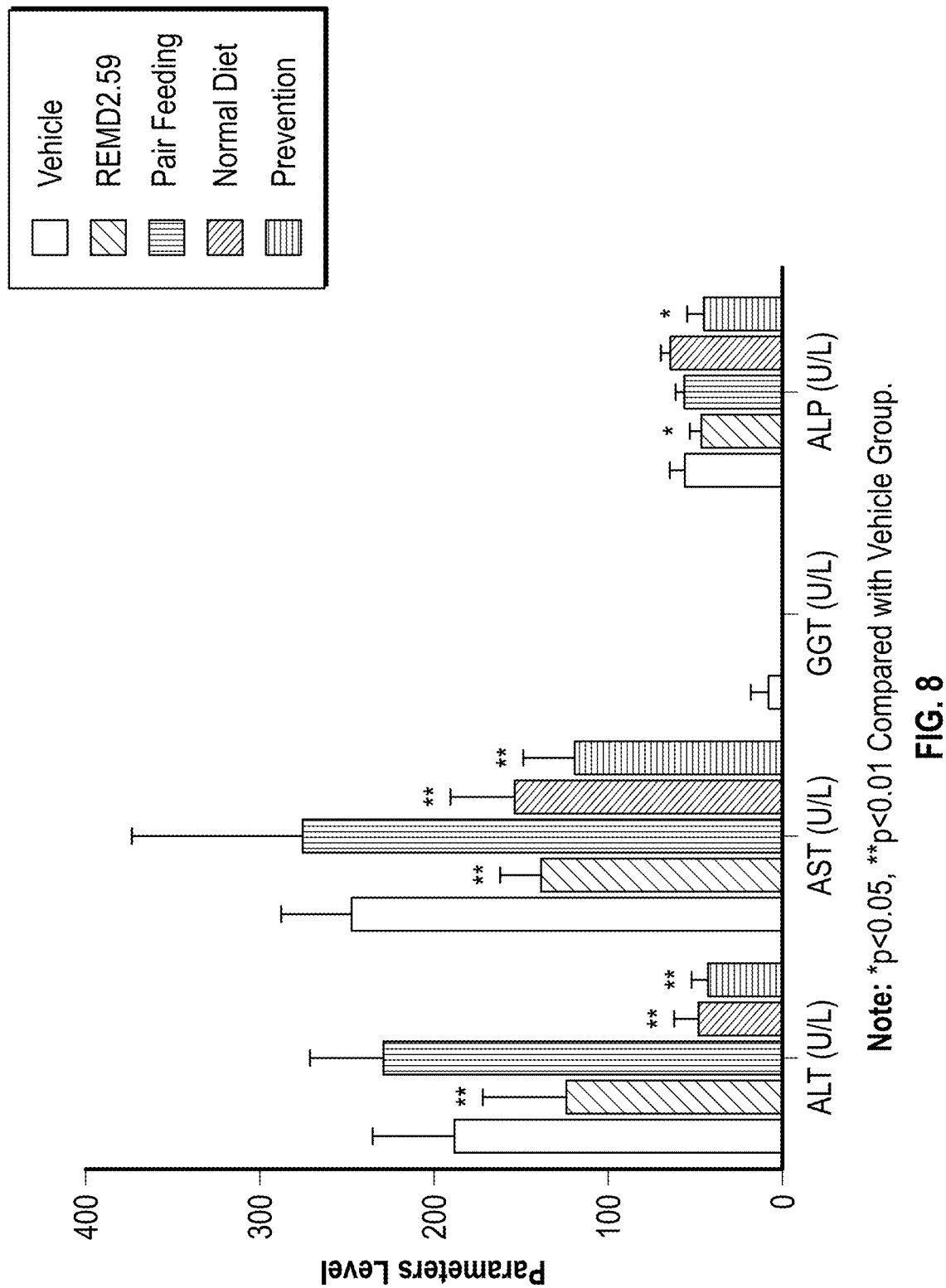
FIG. 8 is a bar graph depicting the in vivo effects on alanine aminotransferase (ALT) levels (U/L), aspartate aminotransferase (AST) levels (U/L), gamma-glutamyl transpeptidase (GGT) levels (U/L), and alkaline phosphatase (ALP) levels (U/L) for the Vehicle group, REMD2.59 group, Pair feeding group, Normal diet group, and Prevention group as described herein, in a HFD DIO mouse study, evaluated at week 20. Treatment commenced on Day 57 (i.e., start of week 9) for all groups but the Prevention group. For the Prevention group, REMD2.59C antibody was administered weekly starting from day 1 of HFD feeding.

As depicted in FIG. 6, triglyceride (TG) levels were not significantly different between the HFD-fed Vehicle Group and the Normal Diet Control Group. REMD2.59 Treatment did not significantly affect TG levels, and although the Prevention Group showed reduced TG levels at Week 16, the changes were not sustained by the end of study. Thus, overall REMD2.59 did not cause any major change in circulating TG levels. As depicted in FIG. 7, the total cholesterol (TCHO) levels were not affected by REMD2.59

Treatment (comparing Vehicle Group vs. REMD2.59 Group), but was significantly reduced by the Prevention Group (up to 47% by Week 20) to a level close to that of the Normal Diet Group.

Lipid Profile in Liver Analysis—

Figure 9:
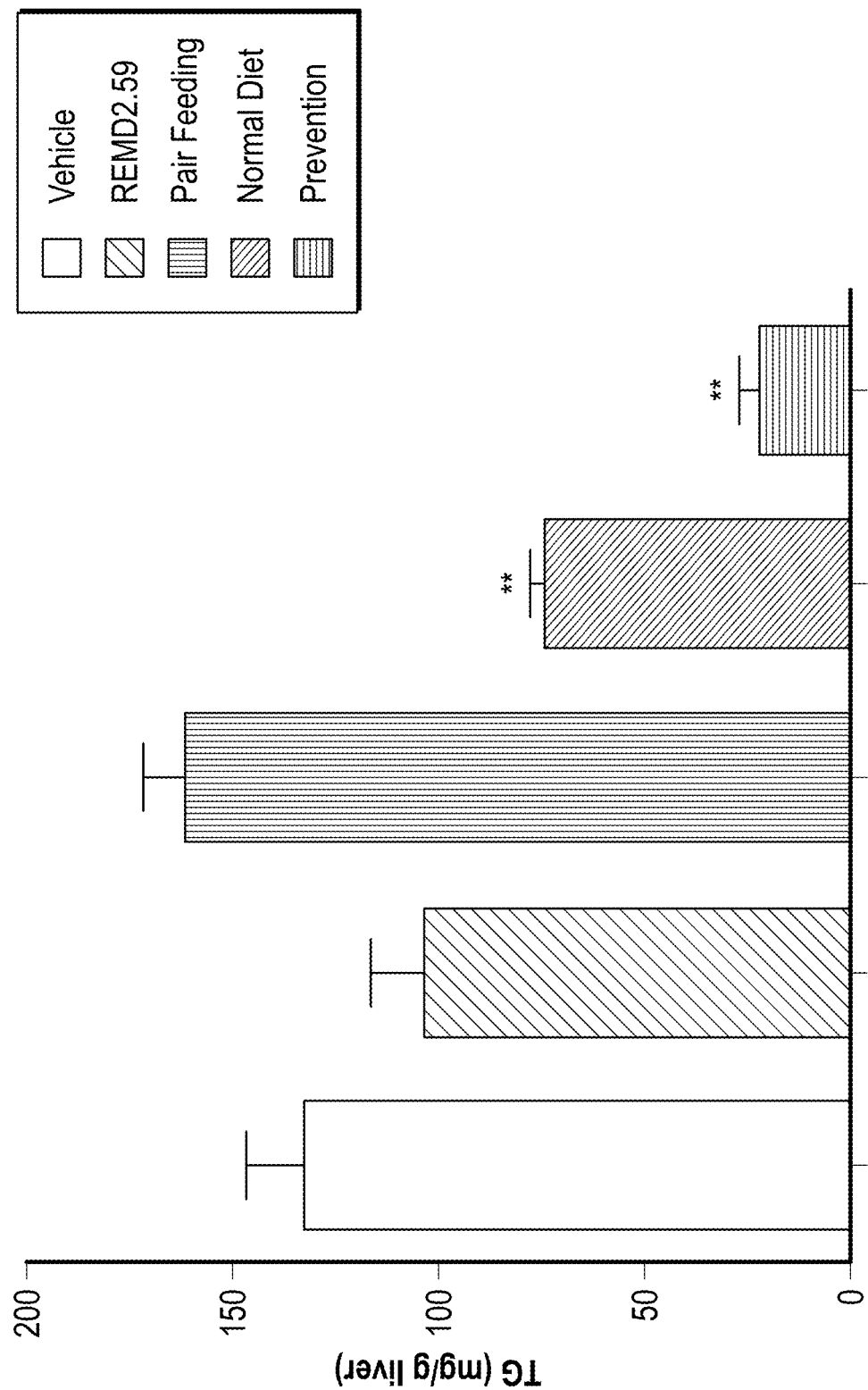
FIG. 9 is a bar graph depicting the in vivo effects on triglyceride (TG) levels (mmol/L) in the liver for the Vehicle group, REMD2.59 group, Pair feeding group, Normal diet group, and Prevention group as described herein, in a HFD DIO mouse study, evaluated at week 20. Treatment commenced on Day 57 (i.e., start of week 9) for all groups but the Prevention group. For the Prevention group, REMD2.59C antibody was administered weekly starting from day 1 of HFD feeding.
Figure 10:
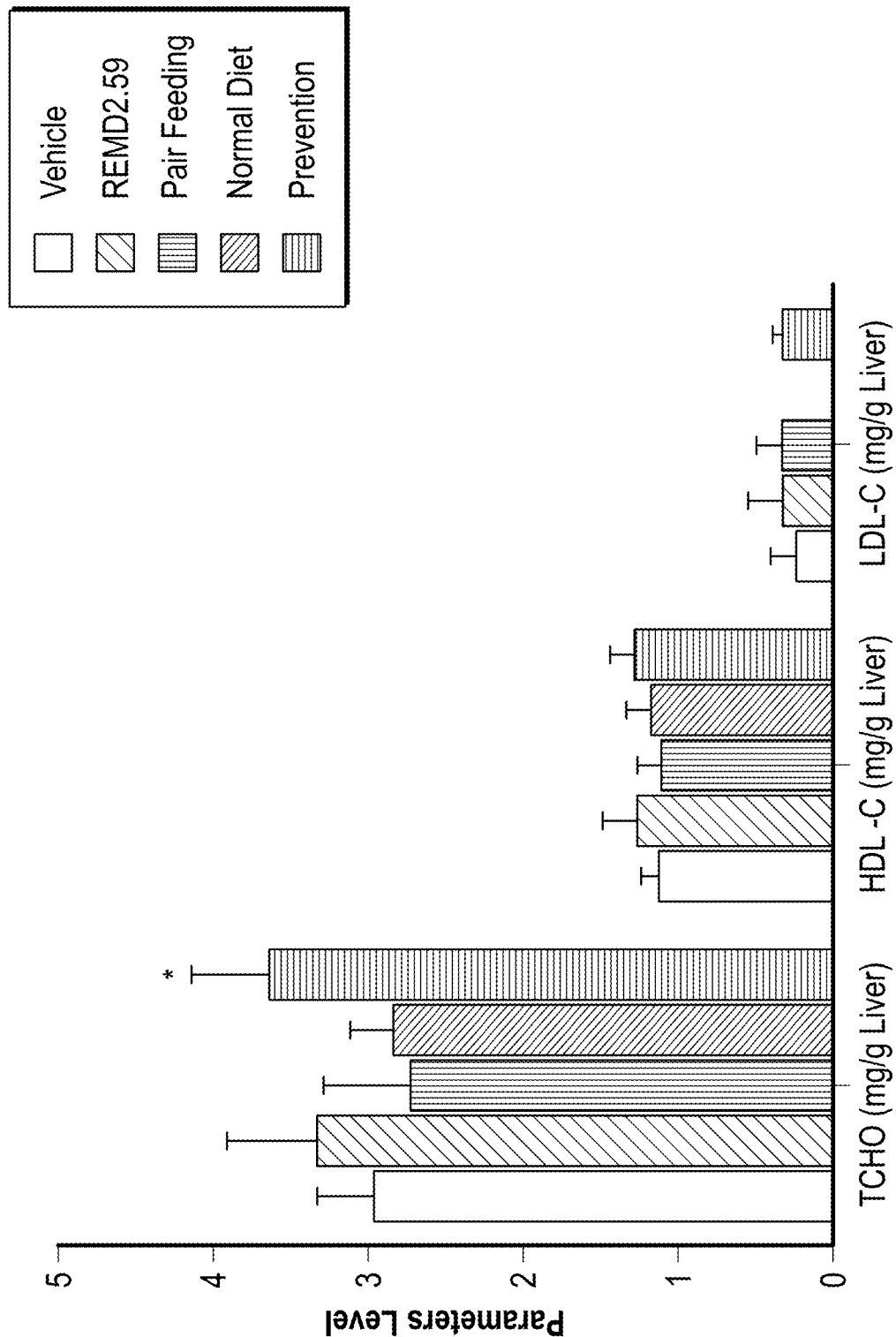
FIG. 10 is a bar graph depicting the in vivo effects on total cholesterol (TCHO) levels (mmol/L), high density lipoprotein cholesterol (HDL-C) levels (mg/g), and low density lipoprotein cholesterol (LDL-C) levels (mg/g) in the liver for the Vehicle group, REMD2.59 group, Pair feeding group, Normal diet group, and Prevention group as described herein, in a HFD DIO mouse study, evaluated at week 20. Treatment commenced on Day 57 (i.e., start of week 9) for all groups but the Prevention group. For the Prevention group, REMD2.59C antibody was administered weekly starting from day 1 of HFD feeding.

As depicted in FIG. 9, REMD2.59 treatment moderately, although statistically insignificantly, reduced TG content in the liver tissue (102.0±45.2 vs. 131.6±46.5 mg/g tissue) in comparison to the Vehicle Group mice. The Prevention Group showed a reduced the liver TG content by 84% (21.4±14.5 vs. 131.6±46.5 mg/g tissue) in comparison to the Vehicle Group. As depicted in FIG. 10, the total cholesterol (TCHO), high density and low density lipoprotein levels (HDL-C and LDL-C) were not significantly affected by REMD2.59 Treatment or Prevention.

Measurement of GLP-1, Insulin and Leptin—

Figure 11:
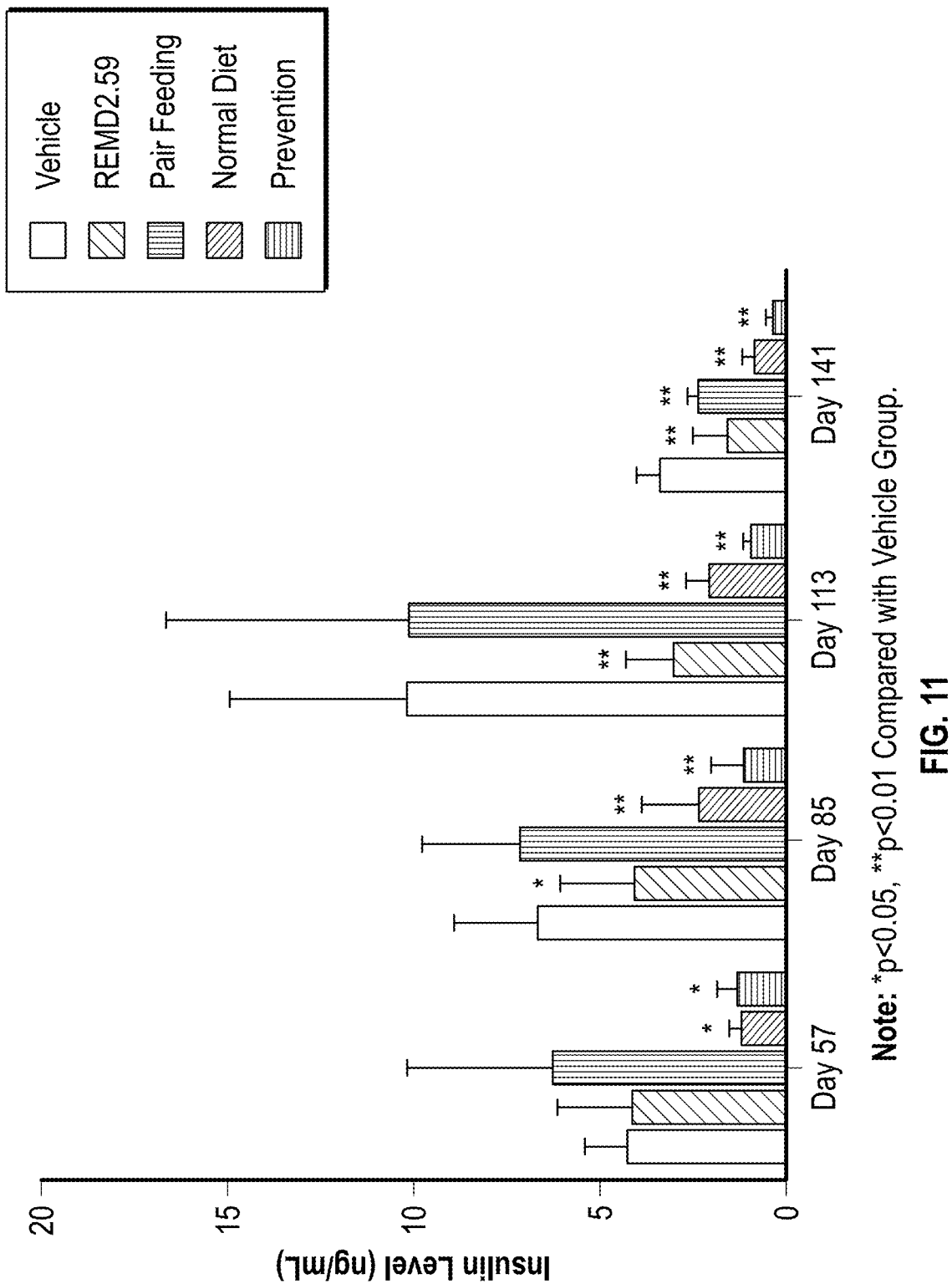
FIG. 11 is a bar graph depicting the in vivo effects on insulin levels (ng/mL) for the Vehicle group, REMD2.59 group, Pair feeding group, Normal diet group, and Prevention group as described herein, in a HFD DIO mouse study, evaluated for 20 weeks. Treatment commenced on Day 57 (i.e., start of week 9) for all groups but the Prevention group. For the Prevention group, REMD2.59C antibody was administered weekly starting from day 1 of HFD feeding. The insulin levels on Day 57, 85, and 113 were tested after 6 hours of fasting, and on Day 141 after fasting for 16 hours (OGTT study was conducted on that day).
Figure 12:
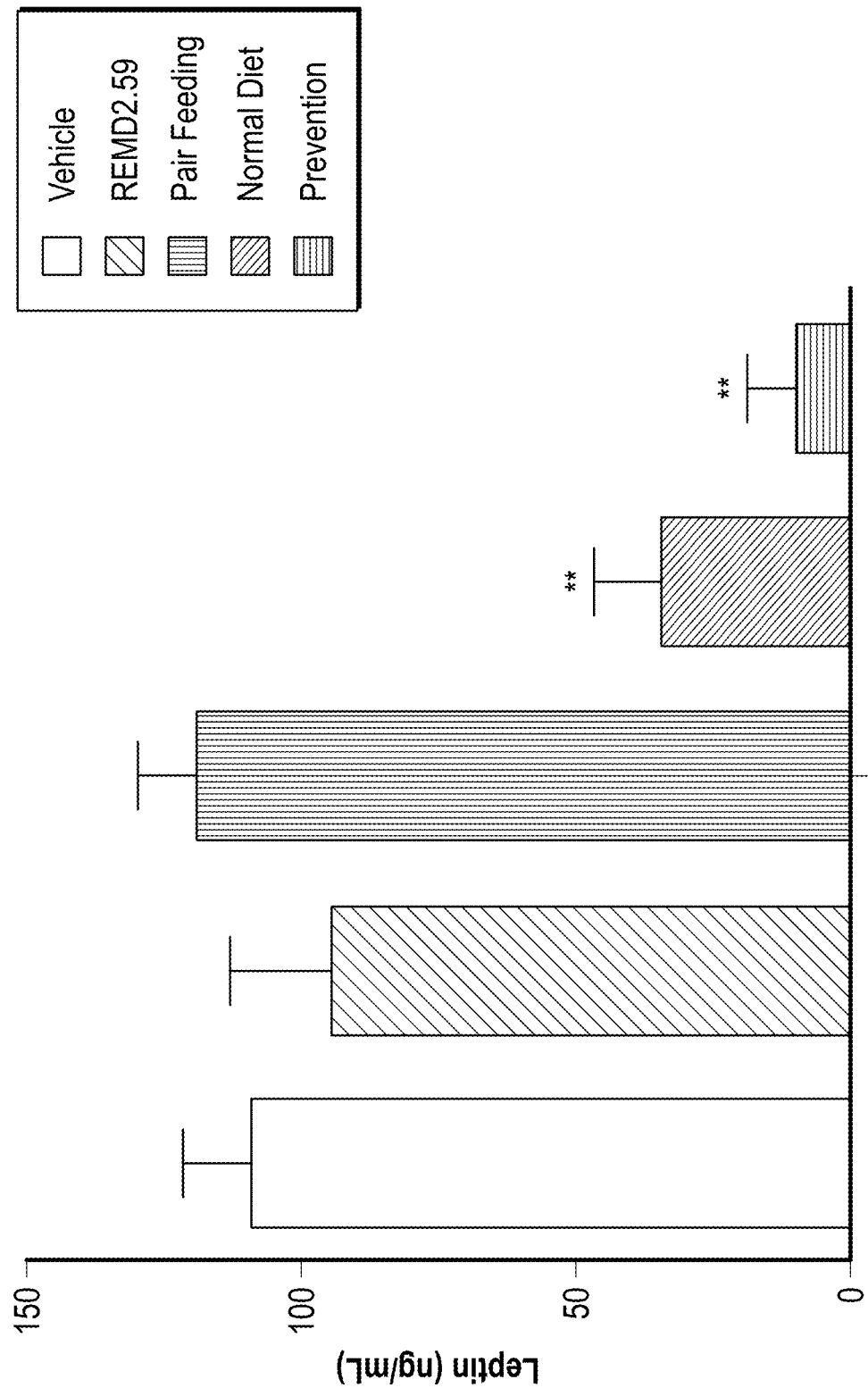
FIG. 12 is a bar graph depicting the in vivo effects on leptin levels (ng/mL) for the Vehicle group, REMD2.59 group, Pair feeding group, Normal diet group, and Prevention group as described herein, in a HFD DIO mouse study, evaluated at week 20. Treatment commenced on Day 57 (i.e., start of week 9) for all groups but the Prevention group. For the Prevention group, REMD2.59C antibody was administered weekly starting from day 1 of HFD feeding. The insulin levels on Day 57, 85, and 113 were tested after 6 hours of fasting, and on Day 141 after fasting for 16 hours (OGTT study was conducted on that day).
Figure 13:
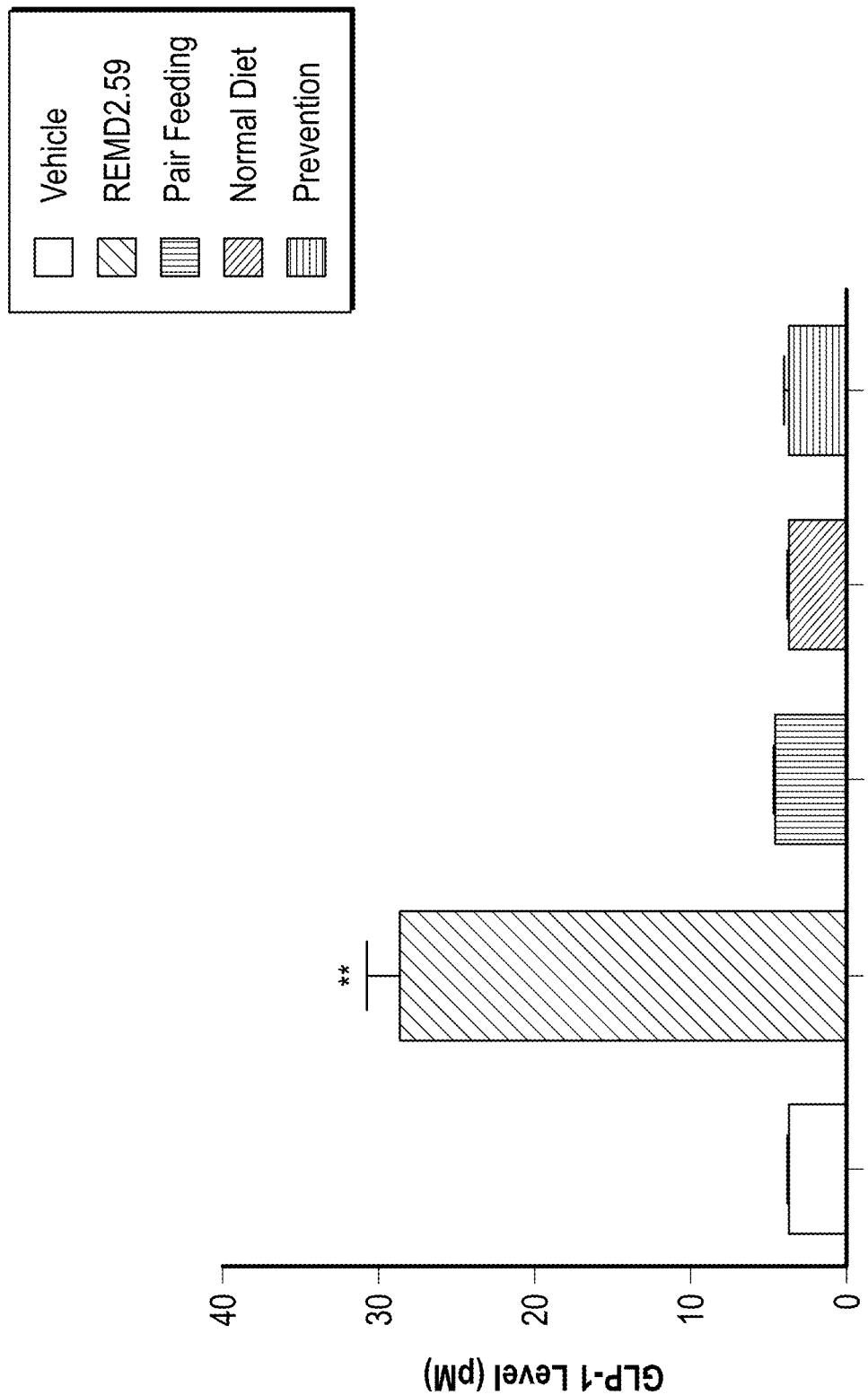
FIG. 13 is a bar graph depicting the in vivo effects on active glucagon-like peptide-1 (GLP-1) levels (pM) for the Vehicle group, REMD2.59 group, Pair feeding group, Normal diet group, and Prevention group as described herein, in a HFD DIO mouse study, evaluated at week 20. Treatment commenced on Day 57 (i.e., start of week 9) for all groups but the Prevention group. For the Prevention group, REMD2.59C antibody was administered weekly starting from day 1 of HFD feeding.

As depicted in FIG. 11, throughout the treatment period and up until the end of the 20-week study, both the REMD2.59 Group and the Prevention Group demonstrated a very robust effect in correcting hyperinsulinemia, as insulin levels were brought back to, or even lower than, the levels seen in the Normal Diet Group. This demonstrates an important biological action for REMD2.59, as in human obesity, type 2 diabetes, and NAFLD/NASH, dyslipidemia is closely associated with hyperinsulinemia. As depicted in FIG. 12, leptin were reduced in the Prevention Group compared to the Vehicle Group, by as much as 92%, and the reduced leptin level was even lower than that of the Normal Diet Group. This is significant in that leptin levels in circulation signifies the extent of adiposity. The REMD2.59 Group reduced leptin levels slightly, although statistically insignificantly. As depicted in FIG. 13, the REMD2.59 Group, but not the Prevention Group, is associated with a 10-fold increase in the circulating active GLP-1 levels, suggesting a contribution by GLP-1 in controlling food intake and other metabolic benefits by blockade of glucagon receptors using REMD2.59. Indeed, REMD2.59 weekly treatment induced a nearly 10-fold increase in the circulating active GLP-1 level, which may account for the additional weight reduction effects.

Histology and Immunohistochemistry Results—

Figure 14:
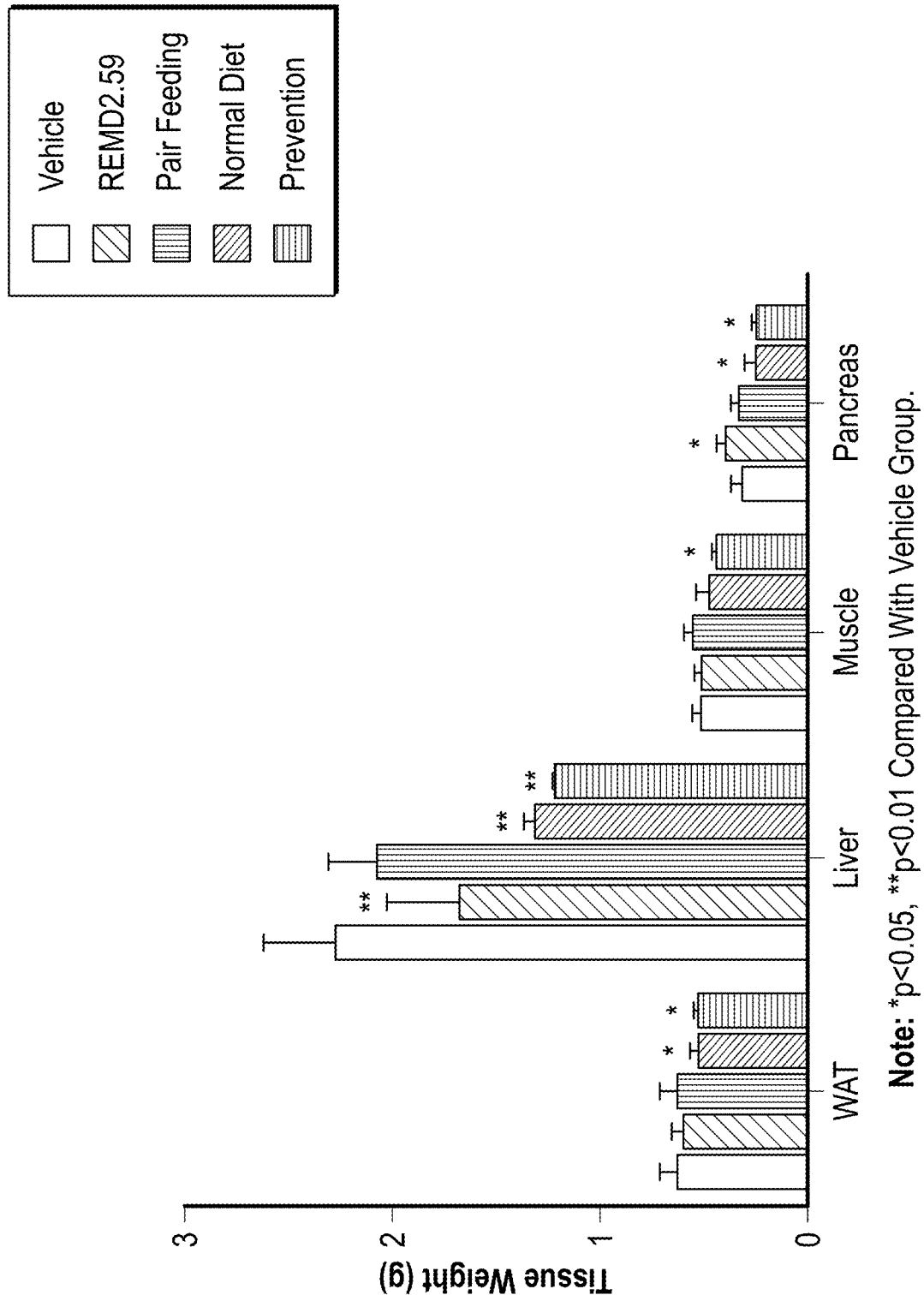
FIG. 14 is a bar graph depicting the wet weight (g) for white adipose tissue (WAT), liver, muscle and pancreas for the Vehicle group, REMD2.59 group, Pair feeding group, Normal diet group, and Prevention group as described herein, in a HFD DIO mouse study, evaluated at week 20. Treatment commenced on Day 57 (i.e., start of week 9) for all groups but the Prevention group. For the Prevention group, REMD2.59C antibody was administered weekly starting from day 1 of HFD feeding.
Figure 15:
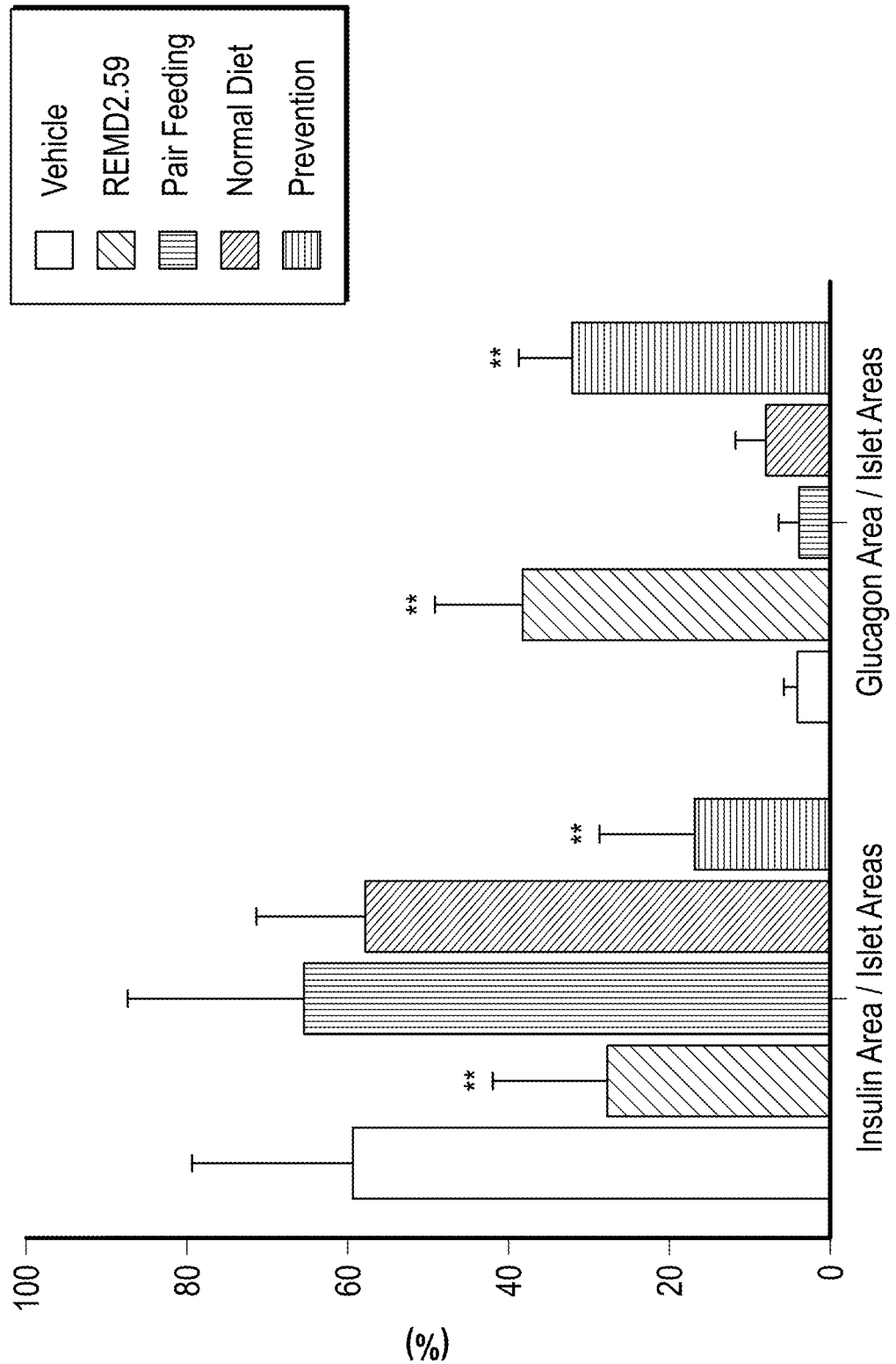
FIG. 15 is a bar graph depicting the IHC results (% insulin area/islet area and % glucagon are/islet area) for the Vehicle group, REMD2.59 group, Pair feeding group, Normal diet group, and Prevention group as described herein, in a HFD DIO mouse study, evaluated at week 20. Treatment commenced on Day 57 (i.e., start of week 9) for all groups but the Prevention group. For the Prevention group, REMD2.59C antibody was administered weekly starting from day 1 of HFD feeding.

As depicted in FIG. 14, the Prevention Group exhibited a significantly reduced the white adipose tissue weight, suggesting that blockade of glucagon receptor is associated with lower adiposity. The Prevention Group also exhibited reduced liver wet weight, which may be related to the reduced fat (TG) and glycogen contents. The REMD2.59 Group exhibited reduced wet liver weight, similarly to the Prevention Group, but slightly increased the pancreatic wet tissue weight, which might be due to the reactive increase in the islet tissue mass. As depicted in FIG. 15, in the immunochemistry (IHC) stained pancreatic sections, the REMD 2.59 Group exhibited reduced insulin area/islet area, similar to the Prevention Group, collectively suggesting that blockade of glucagon receptor signaling attenuated the stimulation to islet beta-cells and to insulin synthesis/secretion. Such a histological finding is in line with the observation that the REMD2.59 Group and Prevention Group exhibited lower insulin levels in circulation (FIG. 11, above). On the other hand, both the REMD2.59 Group and Prevention Group induced marked increases in glucagon area/islet area, suggesting a reactive feedback stimulation of glucagon synthesis/secretion from the islet alpha-cells.

Figure 16:
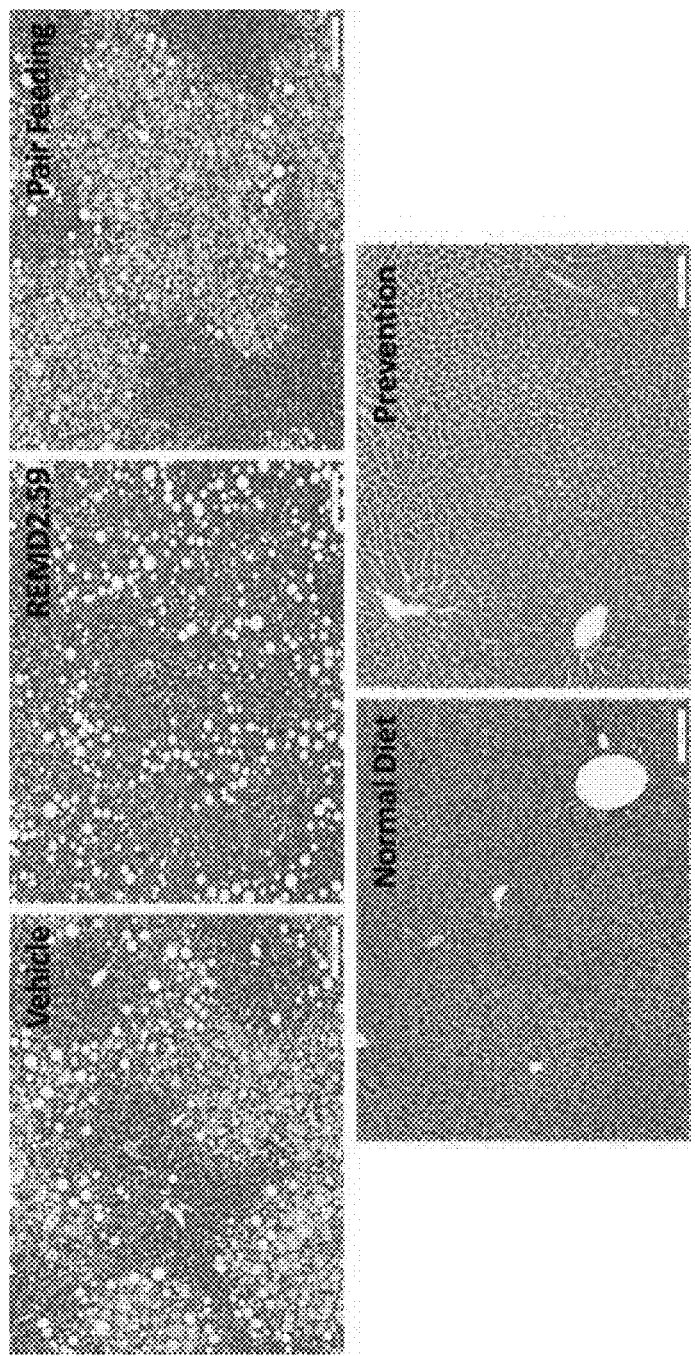
FIG. 16 depicts the results of histological H&E staining (20×10) of various liver sections for the Vehicle group, REMD2.59 group, Pair feeding group, Normal diet group, and Prevention group as described herein, in a HFD DIO mouse study, evaluated at week 20. Treatment commenced on Day 57 (i.e., start of week 9) for all groups but the Prevention group. For the Prevention group, REMD2.59C antibody was administered weekly starting from day 1 of HFD feeding.

As depicted in FIG. 16, the following observations can be derived: 1) the liver tissues from the Vehicle Group show abundance of vacuoles due to fat droplets, which confirms the fatty liver diagnosis of these mice; 2) the liver samples from the REMD2.59 Group appear to show markedly reduced density and sizes of fat droplets, i.e., the areas occupied by overt fat droplets appear to be much smaller than those of the Vehicle Group; 3) the liver tissue samples from the Pair Feeding Group show very little, if any, reduction in the density and sizes of fat droplets from those observed in the Vehicle Group; 4) the liver tissue samples from the Normal Diet Group show very clean liver sections, with virtually no visible fat droplets, comparable to those of the Prevention Group; and 5) the liver tissue samples from the Prevention Group show very clean liver sections, with virtually no visible fat droplets, comparable to those of the Normal Diet Group. The above histological evidence clearly indicates the robust effects of the antagonistic glucagon receptor antibody in correcting, or preventing, the fatty liver changes in the diet-induced obese mice. The histological improvement in fatty liver, as evidenced by the liver histology, is closely associated with the correction of hyperglycemia and hyperinsulinemia, and improvements in glucose and fat metabolism.

Example 2

In view of the significant effects of REMD2.59C treatment demonstrated in Example 1, the relationship between regulating glucose output and the development of NAFLD/NASH in various murine models is evaluated. In this example, the in vivo activity of REMD2.59C is evaluated in the NASH-derived HCC murine model (STAM™ model, Fujii et al, Med Mol Morphol, 46:141-152, 2013). In STAM™ model, C57BL/6J mice are injected with a single subcutaneous injection of 200 μg STZ at 2 days after birth and put on a HFD or chow after 4 weeks of age. In male mice, this combined STZ-HFD treatment results in the development of steatosis and diabetes after 1 week after feeding HFD, and with continued HFD the male mice develop fibrosis, cirrhosis and hepatocellular carcinoma (HCC) along with hyperglycemia and moderate hyperlipidemia, thus closely resembling human NASH. The male mice treated only with STZ and the female mice treated with STZ-HFD develop diabetes, but not HCC.

In this study, four groups of 10 each wild-type C57BL/6J mice (male, age 4-6 weeks, 20-22 g) are injected with a single subcutaneous injection of 200 μg STZ at 2 days after birth and put on a HFD after 4 weeks of age ("STZ-HFD groups") and one group of 10 wild-type C57BL/6J mice (male, age 4-6 weeks, 20-22 g) are injected with a single subcutaneous injection of 200 μg STZ at 2 days after birth and fed with normal diet (chow) after 4 weeks of age ("STZ-Chow group"). The STZ-Chow group continues on chow throughout the 24 week study and the STZ-HFD groups continue on HFD throughout the 24 week study.

At age 5 weeks, the STZ-Chow group is dosed weekly via subcutaneous injection with vehicle (PBS) up until age 24 weeks, and one STZ-HFD group is dosed weekly with 7.5 mg/kg REMD2.59 antibody up to age 24 weeks. At age 8 weeks, one STZ-HFD group is dosed weekly with 2.5 mg/kg REMD2.59 antibody up to age 24 weeks, one STZ-HFD group is dosed weekly with 5.0 mg/kg REMD2.59 antibody up to age 24 weeks, and one STZ-HFD group is dosed weekly with 7.5 mg/kg REMD2.59 antibody up to age 24 weeks.

Various parameters are measured throughout the 24 week study, including, e.g., i) body weight (once a week); ii) fasting blood glucose determination (mice are fasted for 6 hours prior to the test and fasting blood glucose levels are measured via tail veins weekly using Accu-Chek Aviva System®; iii) serum hemoglobin-A1c (HbA1c) determination; iv) serum GLP-1 determination; v) serum insulin and leptin levels via radioimmunoassay (Linco, St. Charles, Mo.); vi) serum alanine aminotransferase (ALT) determination; vii) serum adioponectin determination; viii) serum lipids (e.g., total cholesterol, LDL, HDL and triglycerides) determination; and ix) gamma-glutamyl transpeptidase (CGT) determination. For items iii)-ix), blood samples are collected pre-dose and at the end of the study into tubes without any anticoagulant, immediately centrifuged and the serum transferred into separate sample tubes for evaluation. The various measurements and/or analysis described above is made as described in the Additional Materials and Methods section below.

At the end of the study, livers are rapidly excised, rinsed in ice-cold saline, and weighed. Aliquots of liver are snap frozen in liquid nitrogen and kept at −80° C. until being analyzed. A portion of each liver is fixed in 10% formalin for proper histological analysis of the liver. Liver triglyceride (TG) content, diacylglyceride (DG) content, and ceramide content measurements are made as described in the Additional Materials and Methods section below. Inflammation, central vein fibrosis, and portal tract fibrosis will be evaluated as described in the Additional Materials and Methods section below.

In view of the results demonstrated in Example 1, it is expected that treatment of the wild-type mice using an anti-GCGR antibody will provide beneficial therapeutics effects which may include, e.g., reducing insulin resistance; reducing or preventing hyperinsulinemia, reducing or preventing fat deposits in the liver; reducing or preventing inflammation in the liver; reducing or preventing the accumulation of lipid, e.g., hepatic triacylglycerol, hepatic diacylglycerol, and ceramides; and preventing injury in the liver, and that the development of NAFLD/NASH in such mice may be prevented or treated, thus reducing the risk of the diabetic subject from developing HCC.

Example 3

In view of the significant effects of REMD2.59C treatment demonstrated in Example 1, the in vivo activity of REMD2.59C is evaluated in a murine model of NASH, using db/db mice. The study will be a 24 week study. An additional 48 week study may also be performed. db/db mice from the C57BL/6 background are purchased from Jackson Laboratory (Bar Harbor, Me.). db/db mice are hyperleptinemic, obese and diabetic mice. db/db mice that are fed a methionine and choline deficient (MCD) diet spontaneously develop hepatic steatosis, which progresses to NASH (Wortham et al., Dig Dis Sci., 53(10): 2761-2774, 2008 October). Six mice each of db/db at age 10-12 weeks are fed ad libitum with either a methionine and choline deficient (MCD) diet (MP Biomedicals Solon, Ohio, cat. no. 960439) or the same diet supplemented with methionine and choline (MCDS) diet (MP Biomedicals cat. no. 960441) for 4 weeks, or a HFD+fructose Western Diet (WD)(#58Y1, TestDiet, St Louis, Mo.), or chow (Control Diet)(#58Y2, TestDiet, St Louis, Mo.) for 24 weeks. Mice are housed individually in steel microisolator cages at 22° C. with a 12-h/12-h, light/dark cycle. All procedures were conducted in accordance with the National Institutes of Health (NIH) guidelines for the care and use of laboratory animals. The mice are dosed weekly or bi-weekly via subcutaneous injection with either vehicle (10 mM sodium acetate, 5% sorbitol, and 0.004% polysorbate 20), 2.5 mg/kg REMD2.59C antibody ("Low Dose"), or 5 mg/kg REMD2.59C antibody ("High Dose") for 4 weeks or 24 weeks, as appropriate. The dose administered will not exceed 10 mg/kg per month.

Various parameters are measured throughout the 4 week or 24 week study, including, e.g., i) body weight (once a week); ii) fasting blood glucose determination (mice are fasted for 6 hours prior to the test and fasting blood glucose levels are measured via tail veins weekly using Accu-Chek Aviva System®; iii) serum hemoglobin-A1c (HbA1c) determination; iv) serum GLP-1 determination; v) serum insulin and leptin levels via radioimmunoassay (Linco, St. Charles, Mo.); vi) serum alanine aminotransferase (ALT) determination; vii) serum adioponectin determination; viii) serum lipids (e.g., total cholesterol, LDL, HDL and triglycerides (TG)) determination; and ix) gamma-glutamyl transpeptidase (CGT) determination. For items iii)-ix), blood samples are collected pre-dose and at the end of the study into tubes without any anticoagulant, immediately centrifuged and the serum transferred into separate sample tubes for evaluation. The various measurements and/or analysis described above is made as described in the Additional Materials and Methods section below.

At the end of the study, livers are rapidly excised, rinsed in ice-cold saline, and weighed. Aliquots of liver are snap frozen in liquid nitrogen and kept at −80° C. until being analyzed. A portion of each liver is fixed in 10% formalin for proper histological analysis of the liver. Liver triglyceride (TG) content, diacylglyceride (DG) content, and ceramide content measurements are made as described in the Additional Materials and Methods section below. Inflammation, central vein fibrosis, and portal tract fibrosis will be evaluated as described in the Additional Materials and Methods section below.

In view of the results demonstrated in Example 1, it is expected that treatment of the db/db mice using an anti-GCGR antibody will provide beneficial therapeutics effects which may include, e.g., reducing insulin resistance; reducing or preventing hyperinsulinemia, reducing or preventing fat deposits in the liver; reducing or preventing inflammation in the liver; reducing or preventing the accumulation of lipid, e.g., hepatic triacylglycerol, hepatic diacylglycerol, and ceramides; and preventing injury in the liver, and that the development of NAFLD/NASH in such mice may be prevented or treated.

Example 4

This Example describes a randomized, double-blind, placebo-controlled, parallel group, multiple dose study to evaluate the safety, pharmacokinetics and pharmacodynamic effects of weekly treatment using a fully human anti-GCGR antibody in subjects diagnosed with NASH. The treatment may last a period up to 6 or 12 months, long enough to observe and quantitate treatment efficacy and safety.

Treatment groups include a placebo group and treatment groups to be treated with various dosages of a fully human anti-GCGR antibody which comprises the heavy chain sequence set forth in SEQ ID NO: 51 and the light chain sequence set forth in SEQ ID NO: 52 ("REMD-477"). Examples of non-placebo treatment groups will include, e.g., subjects who receive injections of either 0.01 mg/kg, 0.025 mg/kg, 0.05 mg/kg, 0.075 mg/kg, 0.1 mg/kg, 0.25 mg/kg, 0.5 mg/kg, 0.75 mg/kg, 1.0 mg/kg, 1.5 mg/kg, 2.0 mg/kg, 2.5 mg/kg, 5 mg/kg, 7.5 mg/kg, or 10 mg/kg REMD-477 per week, and subjects who receive injections of either 0.01 mg/kg, 0.025 mg/kg, 0.05 mg/kg, 0.075 mg/kg, 0.1 mg/kg, 0.25 mg/kg, 0.5 mg/kg, 0.75 mg/kg, 1.0 mg/kg, 1.5 mg/kg, 2.0 mg/kg, 2.5 mg/kg, 5 mg/kg, 7.5 mg/kg, or 10 mg/kg REMD-477 weekly.

Primary outcome measures will include, e.g., change in percentage of liver fat content by MRI at: baseline, at 4-week or 8-week intervals, until the end of study; change in the proportion of REMD-477 treated patients relative to placebo achieving improvement of liver fibrosis by at least one stage, at the end of study, in comparison to the baseline assessment; and change in liver enzyme and metabolic markers, including Aspartate Transaminase (AST), Alanine Transaminase (ALT), Bilirubin and Alkaline phosphatase (ALP), at: baseline, at 4-week intervals, until the end of study. Secondary outcome measures will include, e.g., change in fasting plasma glucose levels, average of daily morning glucose after an overnight fast, at pre-treatment baseline, and at weekly intervals until the end of study; change in plasma insulin levels at pre-treatment baseline, and at weekly intervals until the end of study; change in hemoglobin A1c levels (indicator of chronic glucose control) at pre-treatment baseline, and at 4-week or 8-week intervals until the end of study; change in glucose profiles at oral glucose tolerance tests (OGTT), measured at 0, 30, 60, 90 and 120 min after an oral glucose load, at pre-treatment baseline, and at 8-week intervals until the end of study; composite long term outcome measured by the number of patients with the onset of any adjudicated events, including cirrhosis, all-cause mortality, and liver-related clinical outcomes, at the Baseline and the end of study; and changes in scores of the Quality of Life (36-Item Short-Form Health Survey [SF-36]) Questionnaire.

Additional Materials and Methods

Body Weights:

Body weights of all animals are measured weekly throughout the duration of the various studies.

Food Consumption:

Food consumption of all animals are measured daily and/or weekly throughout the duration of the various studies.

Blood Glucose:

The mice were fasted 6 hours prior to blood glucose test from 9 am to 3 pm, and fast blood glucose levels were measured via tail veins on weekly basis by using Accu-Chek Performa System.

Oral Glucose Tolerance Test:

To test the repeat dosing effect of REMD Ab2.59, OGTT was performed for all animals at the end of the study. The baseline (time 0) glucose level was measured after 16 hours fast and prior to glucose challenge. Following oral administration of 2 g/kg glucose, the blood glucose levels were measured at different time points (30, 60, 120 min) by using Accu-Chek Performa System.

Blood Chemistry Analysis:

The lipid profile of every $2^{nd}$ week and terminal blood bio-chemistry parameters (ALT, AST, GGT, ALP) were tested. Blood samples were obtained on week 8, 12, 16 and 20, the samples were immediately processed by centrifugation at 4° C., 4000 g for 15 minutes, and then they were transferred into new test tubes. Lipid profile and blood bio-chemistry parameters were measured by using TOSHIBA TBA-40FR automated biochemical analyzer.

Measurement of Lipid Profile in Liver:

The lipid profiles (TG, TCHO, HDL-C and LDL-C) were extracted from the liver of the animal according to the protocol, and then lipid profile were measured by using TOSHIBA TBA-40FR automated biochemical analyzer.

ELISA Kits Analysis:

The insulin level of all study animals were measured on week 8, 12, 16 and 20. GLP-1 and leptin were measured at the end of the study with ELISA method. The blood serum was used for the analysis.

Liver Weight:

At the end of the study, livers are rapidly excised, rinsed in ice-cold saline, and weighed. Aliquots of liver are snap frozen in liquid nitrogen and kept at −80° C. until being analyzed. A portion of each liver is fixed in 10% formalin for histology.

Liver TG/DG/Ceramide Content:

Liver triglyceride (TG), diacylglyceride (DG), and ceramide content of all animals are measured at the end of the study. Liver samples are homogenized in 50 mM Tris-HCl buffer, pH 7.4, containing 150 mM NaCl, 1 mM EDTA, and 1 μM PMSF and lipids isolated by extraction into chloroform with appropriate internal standards included for each protocol. Extracted lipids were resuspended and diluted in methanol/chloroform (4:1, by volume) before analysis by electrospray ionization-mass spectrometry using a Thermo Electron TSQ Quantum Ultra instrument (San Jose, Calif.). DG molecular species were quantified as sodiated adducts using selected reaction monitoring as previously described with intensity of each species normalized to that of the internal standard di-20:0 DG (Demarco V G et al., Endocrinology, 154:159-171, 2013). TG aliphatic groups were quantified by TG fingerprinting techniques with neutral loss scanning for the loss of each fatty acid from the TG species and comparisons to that of the neutral loss 268 which is derived from the internal standard Tri-17:1 TG (Han et al., Anal Biochem, 295:88-100, 2001). Individual ceramide molecular species were quantified in negative ion mode using neutral loss 256 by comparing the ion intensity of individual molecular species to that of the internal standard (17:0 ceramide) after corrections for type I and type II $^{13}$C isotope effects.

Histology and Immunohistochemistry:

Formalin-fixed liver tissue is processed, and 5-μm-thick paraffin sections are stained with hematoxylin and eosin (H&E) and Masson's trichrome for histological analysis. Inflammation is evaluated on H&E-stained sections and is given a score from 0 to 3 as follows: 0, no inflammation; 1, mild; 2, moderate; 3, severe. The degree of fibrosis is assessed by digital morphometry. Five discrete regions of a trichrome-stained sections from each mouse are randomly selected and within each region identified a portal track and central vein to be digitally photographed. Photographs are obtained with a ×20 objective with the portal tracks or central veins of interest in the center of the field, thus obtaining five portal/periportal and five central/pericentral fields of interest for each mouse. For each field of interest the pixels corresponding to fibrosis are measured based on a narrow band of the blue spectrum corresponding to the stain of clear-cut fibrosis in each specimen, carefully excluding the normal stromal collagen in those areas. The number of pixels corresponding to fibrosis is measured as a percentage of the total pixels of each image using the Image Processing Tool Kit, version 5.0 (Reindeer Graphics, Asheville, N.C.). The results of the five portal/periportal and five central/pericentral fields from each specimen are averaged, and fibrosis is expressed as a percentage of total cross-sectional area for each animal.

Methionine and Choline Deficient (MCD) Diet:

Of the dietary approaches discussed herein, MCD diets produce the most severe NASH phenotype in the shortest time frame. MCD diet is high in sucrose and fat, but lacks methionine and choline, which are essential for hepatic beta-oxidation and the production of very low density lipoprotein (VLDL). This results in the accumulation of intrahepatic lipid and decreased VLDL synthesis (Anstee et al., Int J Exp Pathol, 87(1):1-16, 2006). MCD diets will quickly induce measurable hepatic steatosis (mainly macrovesicular) in rodents by 2-4 weeks and this progresses to inflammation and fibrosis shortly thereafter. Fat levels in MCD diets can vary, though typically they contain about 20% fat by energy. Importantly, unlike human or other diet-induced rodent models of NAFLD, rodents fed MCD diets lose weight (due to a vastly lower caloric intake) and do not become insulin resistant. Since most humans with NASH are obese and insulin resistant, this represents an important difference in how MCD diets model human NASH.

High-Fat Diets (HFD):

HFD are well-known to increase body weight, body fat and induce insulin resistance in rodent models. HFD can also increase liver fat levels quite rapidly (within days) as well as hepatic insulin resistance before significant increases in peripheral fat deposition occur. Chronically, HFD-induced liver fat accumulation may not follow a linear progression and liver fat levels may actually decrease, then increase again during prolonged HFD feeding. When fed for equal lengths of time, HFD feeding results in 10-fold lower liver fat levels compared to what accumulates on an MCD diet. In general, HFD feeding does not produce liver fibrosis and only mild steatosis as compared to MCD diets, thus highlighting an important difference between these dietary regimes. It is important to remember that the term 'HFD' encompasses a wide variety of diet formulas and diets of different composition can be expected to alter the liver phenotype in various ways. An exemplary HFD diet may consist of 36% fat derived-calories (9% corn oil and 27% butter) and 43.2% carbohydrate-derived calories without sugar. HFD (Research Diets, D12492, HFD) was used in these studies.

HFD+Fructose Diet (Western Diet ("WD")):

An exemplary WD may consist of 36% fat derived-calories (9% corn oil and 27% butter), which is the same as HFD, and 43.2% carbohydrate-derived calories with e.g., fructose (e.g., 30% sugar-derived calories).

Murine Models of NASH:

The anti-GCGR antibodies of the present disclosure may be evaluated in any of the other various published murine models of NASH (see, e.g. Poekes et al., Archives of Public Health, 72(1): 07, 2014; Adorini et al., Drug Discovery Today, 17:988-997, 2012; Farrell et al., Liver Int., 34(7): 1084-93, 2014; Rooyen et al, Gastroenterology, 141(4): 1393-1403, 2011; Ishimoto et al., Hepatology, 58(5):1632-1643, 2013; Farrell et al., Gut and Liver, 6(2):149-171, 2012; Sahai et al., Am J Physiol Gastrointest Liver Physiol, 287:G1035-G1043, 2004; Wortham et al., Dig Dis Sci, 53(10):2761-2774, 2008; Lieber et al, Am J Clin Nutr, 79:502-509, 2004).

All of the articles and methods disclosed and claimed herein can be made and executed without undue experimentation in light of the present disclosure. While the articles and methods of this disclosure have been described in terms of preferred embodiments, it will be apparent to those of skill in the art that variations may be applied to the articles and methods without departing from the spirit and scope of the disclosure. All such variations and equivalents apparent to those skilled in the art, whether now existing or later developed, are deemed to be within the spirit and scope of the disclosure as defined by the appended claims. All patents, patent applications, and publications mentioned in the specification are indicative of the levels of those of ordinary skill in the art to which the disclosure pertains. All patents, patent applications, and publications are herein incorporated by reference in their entirety for all purposes and to the same extent as if each individual publication was specifically and individually indicated to be incorporated by reference in its entirety for any and all purposes. The disclosure illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

SEQUENCE LISTINGS

The amino acid sequences listed in the accompanying sequence listing are shown using standard three letter code for amino acids, as defined in 37 C.F.R. 1.822. This disclosure includes a Sequence Listing in computer readable form (ST25 format text file) prepared through the use of software program PatentIn and is identical to the accompanying sequence listings.

SEQ ID NO: 1 is the amino acid sequence of a human glucagon receptor (GCGR) molecule (Accession Number AA104855).

SEQ ID NO: 2 is the amino acid sequence encoding the heavy chain variable region of a fully human anti-GCGR antibody. SEQ ID NO: 3 is the amino acid sequence encoding the light chain variable region of a fully human anti-GCGR antibody.

SEQ ID NO: 4 is the amino acid sequence encoding the heavy chain variable region of a fully human anti-GCGR antibody. SEQ ID NO: 5 is the amino acid sequence encoding the light chain variable region of a fully human anti-GCGR antibody.

SEQ ID NO: 6 is the amino acid sequence encoding the heavy chain variable region of a fully human anti-GCGR antibody. SEQ ID NO: 7 is the amino acid sequence encoding the light chain variable region of a fully human anti-GCGR antibody.

SEQ ID NO: 8 is the amino acid sequence encoding the heavy chain of a chimeric anti-GCGR antibody. SEQ ID NO: 9 is the amino acid sequence encoding the light chain of a chimeric anti-GCGR antibody.

SEQ ID NOS: 10-28 are amino acid sequences encoding the heavy chain variable regions of various fully human anti-GCGR antibodies.

SEQ ID NOS: 29-47 are amino acid sequences encoding the light chain variable regions of various fully human anti-GCGR antibodies.

SEQ ID NO: 48 is the amino sequence encoding the kappa light chain constant region. SEQ ID NO: 49 is the amino sequence encoding the lambda light chain constant region.

SEQ ID NO: 50 is the amino sequence encoding the IgG2 heavy chain constant region.

SEQ ID NO: 51 is the amino acid sequence encoding the heavy chain of a human anti-GCGR antibody. SEQ ID NO: 52 is the amino acid sequence encoding the light chain of a human anti-GCGR antibody.

SEQUENCE LISTINGS

SEQ ID NO: 1-Amino acid sequence of a human glucagon receptor (GCGR) molecule
MPPCQPQRPLLLLLLLLACQPQVPSAQVMDFLFEKWKLYGDQCHHNLSLLPPPTELVCNRTFD
KYSCWPDTPANTTANISCPWYLPWHHKVQHRFVFKRCGPDGQWVRGPRGQPWRDASQCQ
MDGEEIEVQKEVAKMYSSFQVMYTVGYSLSLGALLLALAILGGLSKLHCTRNAIHANLFASFVLK
ASSVLVIDGLLRTRYSQKIGDDLSVSTWLSDGAVAGCRVAAVFMQYGIVANYCWLLVEGLYLH
NLLGLATLPERSFFSLYLGIGWGAPMLFVVPWAVVKCLFENVQCWTSNDNMGFWWILRFPVFL
AILINFFIFVRIVQLLVAKLRARQMHHTDYKFRLAKSTLTLIPLLGVHEVVFAFVTDEHAQGTLRSA
KLFFDLFLSSFQGLLVAVLYCFLNKEVQSELRRRWHRWRLGKVLWEERNTSNHRASSSPGHG
PPSKELQFGRGGGSQDSSAETPLAGGLPRLAESPF SEQ ID NO: 2-Amino acid sequence of a HCVR of a human antibody that binds GCGR
QVQLVESGGGVVQPGRSLRLSCAASGFTFSSYGMHWVRQAPGKGLEWVAVMWYD
GSNKDYVDSVKGRFTISRDNSKNTLYLQMNRLRAEDTAVYYCAREKDHYDILTGYNY
YYGLDVWGQGTTVTVSS SEQ ID NO: 3-Amino acid sequence of a LCVR of a human antibody that binds GCGR
DIQMTQSPSSLSASVGDRVTITCRASQGIRNDLGWYQQKPGKAPKRLIYAASSLQSGV
PSRFSGSGSGTEFTLTISSVQPEDFVTYYCLQHNSNPLTFGGGTKVEIK SEQ ID NO: 4-Amino acid sequence of a HCVR of a human antibody that binds GCGR
QVQLVESGGGVVQPGRSLRLSCAASGFTFSSYGMHWVRQAPGKGLEWV
AVMWYDGSNKDYVDSVKGRFTISRDNSKNTLYLQMNSLRAEDTAVYYCAREKDHYDI
LTGYNYYYGLDVWGQGTTVTVSS SEQ ID NO: 5-Amino acid sequence of a LCVR of a human antibody that binds GCGR
DIQMTQSPSSLSASVGDRVTITCRASQGIRNDLGWYQQKPGKAPKRLIYAASSLQSGV
PSRFSGSGSGTEFTLTISSLQPEDFVTYYCLQHNSNPLTFGGGTKVEIK SEQ ID NO: 6-Amino acid sequence of a HCVR of a human antibody that binds GCGR
QVQLVESGGGVVQPGRSLRLSCAASGFTFSSYGMHWVRQAPGKGLEWVAVMWYD
GSNKDYVDSVKGRFTISRDNSKNTLYLQMNRLRAEDTAVYYCAREKDHYDILTGYNY
YYGLDVWGQGTTVTVSS SEQ ID NO: 7-Amino acid sequence of a LCVR of a human antibody that binds GCGR
DIQMTQSPSSLSASVGDRVTITCRASQGIRNDLGWYQQKPGKAPKRLIYAASSLESGV
PSRFSGSGSGTEFTLTISSVQPEDFVTYYCLQHNSNPLTFGGGTKVEIK SEQ ID NO: 8-Amino acid sequence of a heavy chain of a chimeric antibody that binds GCGR
MEFGLSWVFLVALLRGVQCQVQLVESGGGVVQPGRSLRLSCAASGFTFSSYGMHWVRQAPG
KGLEWVAVMWYDGSNKDYVDSVKGRFTISRDNSKNTLYLQMNRLRAEDTAVYYCAREKDHY
DILTGYNYYYGLDVWGQGTTVTVSSAKTTPPSVYPLAPGSAAQTNSMVTLGCLVKGYFPEPVT
VTWNSGSLSSGVHTFPAVLQSDLYTLSSSVTVPSSTWPSETVTCNVAHPASSTKVDKKIVPRD
CGCKPCICTVPEVSSVFIFPPKPKDVLTITLTPKVTCVVVDISKDDPEVQFSWFVDDVEHTAQT
QPREEQFNSTFRSVSELPIMHQDWLNGKEFKCRVNSAAFPAPIEKTISKTKGRPKAPQVYTIPP
PKEQMAKDKVSLTCMITDFFPEDITVEWQWNGQPAENYKNTQPIMDTDGSYFVYSKLNVQKS
NWEAGNTFTCSVLHEGLHNHHTEKSLSHSPGK SEQ ID NO: 9-Amino acid sequence of a light chain of a chimeric antibody that binds GCGR
MDMRVPAQLLGLLLLWFPGARCDIQMTQSPSSLSASVGDRVTITCRASQGIRNDLGWYQQKP
GKAPKRLIYAASSLESGVPSRFSGSGSGTEFTLTISSVQPEDFVTYYCLQHNSNPLTFGGGTKV
EIKRADAAPTVSIFPPSSEQLTSGGASVVCFLNNFYPKDINVKWKIDGSERQNGVLNSWTDQDS
KDSTYSMSSTLTLTKDEYERHNSYTCEATHKTSTSPIVKSFNRNEC SEQ ID NO: 10-Amino acid sequence of a HCVR of a human antibody that binds GCGR
QVQLVESGGGVVQPGRSLRLSCAASGFTFSNYGMHWVRQAPGKGLEWVAVILSDGRNKYYA
DSVKGRFTISRDNSKNTLYLQMNSLRAEDTAVYYCARDDYEILTGYGYYGMDVWGQGTTVTV
SS SEQ ID NO: 11-Amino acid sequence of a HCVR of a human antibody that binds GCGR
QVQLVESGGGVVQPGRSLRLSCAASGFTFSSYGMHWVRQAPGKGLEWVAVILNDGRNKYYA
DSVKGRFTISRDNSKNTLYLQMNSLRAEDTAVYYCARDDYEILTGYGYYGMDVWGQGTTVTV
SS SEQ ID NO: 12-Amino acid sequence of a HCVR of a human antibody that binds GCGR
QVQLQQSGPGLVKPSQTLSLTCAISGDSVSSNGAAWNWIRQSPSRGLEWLGRTYYRSKWYY
DYAGSVKSRININPDTSKNQFSLQVNSVTPEDTAVYYCTRDRSSGWNEGYYYYGMDVWGQG
TTVTVSS SEQ ID NO: 13-Amino acid sequence of a HCVR of a human antibody that binds GCGR
QVQLVESGGGVVQPGRSLRLSCAASGFTFSSYDIHWVRQAPGKGLEWVAVLSSDGNNKYCA
DSVKGRFTISRDNSKNTLYLQMNSLRTEDTAVYYCAREEVYYDILTGYYDYYGMDVWGQGTTV
TVSS SEQ ID NO: 14-Amino acid sequence of a HCVR of a human antibody that binds GCGR
QVQLQESGPGLVKPSETLSLTCTVSGGSISTYFWTWIRQFPGKGLEWIGYIFYSGSTNYNPSLK
SRVTISVDTSKNQFSLKLSSVTAADTAVYYCAREGYYDILTGEDYSGMDVWGQGTTVTVSS

SEQUENCE LISTINGS

SEQ ID NO: 15-Amino acid sequence of a HCVR of a human antibody that binds GCGR
QVQLQQSGPGLVKPSQILSLICAISGDRVSSNGAAWNWIRQSPSRGLEWLGRTYYRSKWYYD
YAGSVKSRININPDTSKNQFSLQVNSVTPEDTAVYYCARDRSSGWNEGYYYYGMDVWGQGT
TVTVSS SEQ ID NO: 16-Amino acid sequence of a HCVR of a human antibody that binds GCGR
QVQLQESGPGLVKPSETLSLTCTVSGGSISTYFWTWIRQFPGEGLEWIGYIFYSGNTNYNPSLT
SRVTISVDTSKNQFSLKLSSVTAADTAVYYCAREGYYDILTGEDYSYGIDVWGQGTTVTVSS SEQ ID NO: 17-Amino acid sequence of a HCVR of a human antibody that binds GCGR
QVQLVESGGGVVQPGRSLRLSCAASGFIFSSYGMHWVRQAPGKGLEWVAVISNDGSNKYYA
DFVKGRFTISRDNSKNTLYLQMNSLRAEDTAVYYCAREDYDILTGNGVYGMDVWGQGTTVTV
SS SEQ ID NO: 18-Amino acid sequence of a HCVR of a human antibody that binds GCGR
EVQLVESGGGLVQPGGSLRLSCAASGFTFSSYTMNWVRQAPGKGLEWVSYISGSSSLIYYAD
SVKGRFTISRDNAKNSLYLHMNSLRDEDTAVYYCARARYNWNDYYGMDVWGQGTTVTVSS SEQ ID NO: 19-Amino acid sequence of a HCVR of a human antibody that binds GCGR
QVQLVESGGGVVQPGRSLRLSCAASGFAFSSYGIHWVRQAPGKGLEWVAGIWYDGSNKYYA
DSVKGRFTVSRDNSKNTLYLQMNSLRAEDTAVYYCARLFDAFDIWGQGTMVTVSS SEQ ID NO: 20-Amino acid sequence of a HCVR of a human antibody that binds GCGR
EVQLVESGGGLVQPGGSLRLSCAASGFIFSSYTMNWVRQAPGKGLEWVSYISSSSSLIYYADS
VKGRFTISRDNAKNSLYLQMNSLRDEDTAVYYCARSDYYGSGSYYKGNYYGMDVWGQGTTV
TVSS SEQ ID NO: 21-Amino acid sequence of a HCVR of a human antibody that binds GCGR
QVQLVESGGGVVQPGRSLRLSCAASGFTFSSYGMHWVRQAPGKGLEWVTIIWSDGINKYYAD
SVKGRFTISRDNSKNTLNLQMNSLRAEDTAVYYCARERGLYDILTGYYDYYGIDVWGQGTTVT
VSS SEQ ID NO: 22-Amino acid sequence of a HCVR of a human antibody that binds GCGR
QVQLVESGGGVVQPGRSLRLSCAASGFTFSSYGMHWVRQAPGKGLEWVTIIWSDGINKYYAD
SVKGRFTISRDNSKNTLNLQMNSLRAEDTAVYYCARERGLYDILTGYYDYYGIDVWGQGTTVT
VSS SEQ ID NO: 23-Amino acid sequence of a HCVR of a human antibody that binds GCGR
EVQLVESGGGLVKPGGSLRLSCAASGITFRSYSMNWVRQAPGKGLEWVSAISSSSSYIYYADS
VKGRFTISRDNAKNSVYLQMNSLRAEDTAVYYCARGRYGMDVWGQGTTVTVSS SEQ ID NO: 24-Amino acid sequence of a HCVR of a human antibody that binds GCGR
QVQLVESGGGVVQPGRSLRLSCAASGSTFRSYDMHWVRQAPGKGLEWVAVISYDGSNKYYG
DSVKGRLTISRDNSKNTLYLQMNSLRAEDTAVYYCARDQYDILTGYSSDAFDIWGQGTMVTV
SS SEQ ID NO: 25-Amino acid sequence of a HCVR of a human antibody that binds GCGR
QVQLVESGGGVVQPGRSLRLSCAASGFTFSRYGMHWVRQAPGKGLEWVAVIWYDGSHKYY
EDSVKGRFTISRDNSKNTLYLQMNSLRADDTGVYYCARVGYGSGWYEYYYHYGMDVWGQGT
TVTVSS SEQ ID NO: 26-Amino acid sequence of a HCVR of a human antibody that binds GCGR
QVQLVESGGGVVQPGRSLRLSCAASGFTFSSYGMHWVRQAPGKGLEWVAVMWYDGSNKDY
VDSVKGRFTISRDNSKNTLYLQMNRLRAEDTAVYYCAREKDHYDILTGYNYYYGLDVWGQGTT
VTVSS SEQ ID NO: 27-Amino acid sequence of a HCVR of a human antibody that binds GCGR
QVQLVESGGGVVQPGRSLRLSCAASGFTFSSYGMHWVRQAPGKGLEWVAVMWYDGSNKDY
VDSVKGRFTISRDNSKNTLYLQMNRLRAEDTAVYYCAREKDHYDILTGYNYYYGLDVWGQGTT
VTVSS SEQ ID NO: 28-Amino acid sequence of a HCVR of a human antibody that binds GCGR
QVQLVESGGGVVQPGRSLRLSCAASGITFSSYGMHWVRQAPGKGLEWVASIWYDGSNKYYV
DSVKGRFTIFRDNSKKTLYLQMNRLRAEDTAVYYCARLGGGFDYWGQGTLVTVSS SEQ ID NO: 29-Amino acid sequence of a LCVR of a human antibody that binds GCGR
DIQMTQSPSSLSASVGDRVTITCRASQDISNYLAWFQKKPGKAPKSLIYVVSSLQSGVPSRFSG
SGSGTDFTLTINNLQPEDFATYYCQQYNHYPLTFGGGTRVEIKR SEQ ID NO: 30-Amino acid sequence of a LCVR of a human antibody that binds GCGR
DIQMTQSPSSLSASVGDRVTITCRASQDISNYLAWFQQRPGKAPKSLIYVVSSLQSGVPSRFSG
SGSGTDFTLTISNLQPEDFATYFCQQYNHYPLTFGGGTKVEIKR SEQ ID NO: 31-Amino acid sequence of a LCVR of a human antibody that binds GCGR
DIQMTQFPSSLSASIGDRVTITCQASQDISNFLNWFQQKPGKAPKLLIYDASDLETGVPSRFSGS
GAGTDFTFTISSLQPEDIATYFCQQYDDLPLTFGGGTRVDIKR -continued

SEQUENCE LISTINGS

SEQ ID NO: 32-Amino acid sequence of a LCVR of a human antibody that binds GCGR
DIQMTQSPSSLSASVGDRVTITCRASQGIRNDLGWYQQKPGKAPKRLIYAASSLQSGVPSRFS
GSGSGTEFTLTISSLQPEDFATYYCLQHNSNPLTFGGGTKVEIKR SEQ ID NO: 33-Amino acid sequence of a LCVR of a human antibody that binds GCGR
QNVLTQSPGTLSLSPGERVTLSCRASQSVSSSYLAWYQQKPGQAPRLLIFGVSSRATGIPDRF
SGSGSGTDFSLTISRLEPEDFAVYYCQQYGNSPFTFGPGTKVDIKR SEQ ID NO: 34-Amino acid sequence of a LCVR of a human antibody that binds GCGR
DIQMTQFPSSLSASIGDRVTITCQASQDISNFLNWFQQKPGKAPKLLIYDASDLETGVPSRFSGS
GAGTDFTFTISSLQPEDVATYFCQQYDNLPLTFGGGTKVDIKR SEQ ID NO: 35-Amino acid sequence of a LCVR of a human antibody that binds GCGR
ENVLTQSPGTLSLSPGERATLSCRASQSVTSSYLAWYQQKPGQAPRLLIFGVSSRATGIPDRF
SGSGSGTDFSLTISRLEPEDFAVYYCQQYGNSPFTFGPGTKVDIKR SEQ ID NO: 36-Amino acid sequence of a LCVR of a human antibody that binds GCGR
DIQMTQSPSSLSASVGDRVTITCRASQGIDMYLAWFQQKPGKAPKSLIYAASSLQSGVPSKFS
GSGFGTDFTLTISSLQPEDFATYYCQQYNIFPFTFGPGTKVDVKR SEQ ID NO: 37-Amino acid sequence of a LCVR of a human antibody that binds GCGR
DIQMTQSPSSLSASVGDRVTITCRASQGIRNDLGWYQQKPGKAPKRLIYAASSLESGVPSRFS
GSGSGTEFTLTISSLQPEDFATYYCLQHNSYPWTFGQGTKVEIKR SEQ ID NO: 38-Amino acid sequence of a LCVR of a human antibody that binds GCGR
KIVMTQTPLALPVIPGEPASISCRSSQSLVDSDDGDTYLDWYLQKPGQSPQVLIHRLSYRASGV
PDRFSGSGSGTDFTLKISRVEAEDVGIYYCMHRIEFPFTFGGGTKVEIKR SEQ ID NO: 39-Amino acid sequence of a LCVR of a human antibody that binds GCGR
DIQMTQSPSSLSASVGDRVTITCRASQGIRNDLGWYQQRPGKAPKRLIYAASSLQTGVPSRFS
GSGSGTEFTLTISSLQPEDFATYYCLQHNSYPWTFGQGTKVEIKR SEQ ID NO: 40-Amino acid sequence of a LCVR of a human antibody that binds GCGR
GIVLTQSPLSLPVTPGEPASISCRSSQSLLHSNGYNYLDWYLQKPGQSPQLLIYLGSNRASGVP
DRFSGSGSGTDFTLKISRVEAEDVGVYYCMEALQTMCSFGQGTKLEIKR SEQ ID NO: 41-Amino acid sequence of a LCVR of a human antibody that binds GCGR
GIVLTQSPLSLPVTPGEPASISCRSSQSLLHSNGYNYLDWYLQKPGQSPQLLIYLGSNRASGVP
DRFSGSGSGTDFTLKISRVEAEDVGVYYCMEALQTMSSFGQGTKLEIKR SEQ ID NO: 42-Amino acid sequence of a LCVR of a human antibody that binds GCGR
DIVMTQTPLFLPVTPGEPASISCRSSQTLLDSDDGNTYLDWYLQKPGQSPQRLIYTLSYRASGV
PDRFSGSGSGTDFTLKISRVEAEDVGIYYCMQHIEFPSTFGQGTRLEIKR SEQ ID NO: 43-Amino acid sequence of a LCVR of a human antibody that binds GCGR
SYELTQPPSVSVSPGQTASITCSGDKLGDKYASWYQQKPGQSPVLVIYQSTKRPSGIPERFSG
SNSGNTATLTISGTQAMDEADYYCQAWDSSTVVFGGGTKLTVLG SEQ ID NO: 44-Amino acid sequence of a LCVR of a human antibody that binds GCGR
NIVMTQTPLSLSVTPGQPASISCKSSQSLLHSDGKNYLFWYLQKPGQSPQLLIYEVSYRFSGVP
DRFSGSGSGTDFSLKISRVEAEDVGVYYCMQNIQPPLTFGQGTRLEIKR SEQ ID NO: 45-Amino acid sequence of a LCVR of a human antibody that binds GCGR
DIQMTQSPSSLSASVGDRVTITCRASQGIRNDLGWYQQKPGKAPKRLIYAASSLQSGVPSRFS
GSGSGTEFTLTISSVQPEDFVTYYCLQHNSNPLTFGGGTKVEIKR SEQ ID NO: 46-Amino acid sequence of a LCVR of a human antibody that binds GCGR
DIQMTQSPSSLSASVGDRVTITCRASQGIRNDLGWYQQKPGKAPKRLIYAASSLESGVPSRFS
GSGSGTEFTLTISSVQPEDFVTYYCLQHNSNPLTFGGGTKVEIKR SEQ ID NO: 47-Amino acid sequence of a LCVR of a human antibody that binds GCGR
DIVLTQTPLSLPVTPGEPASISCRSSQSLLDRDDGDTYLDWYLQKPGQSPQLLIYTLSYRASGV
PDRFSGSGSGTDFSLKISRVEAEDVGVYYCMQRIEFPFTFGPGTKVDIKR SEQ ID NO: 48-Amino acid sequence of the constant light chain kappa region
RTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC SEQ ID NO: 49-Amino acid sequence of the constant light chain lambda region
GQPKAAPSVTLFPPSSEELQANKATLVCLISDFYPGAVTVAWKADSSPVKAGVETTTPSKQSN
NKYAASSYLSLTPEQWKSHRSYSCQVTHEGSTVEKTVAPTECS SEQ ID NO: 50-Amino sequence of the IgG2 heavy chain constant region
ASTKGPSVFPLAPCSRSTSESTAALGCLVKDYFPEPVTVSWNSGALTSGVHTFPAVLQSSGLY
SLSSVVTVPSSNFGTQTYTCNVDHKPSNTKVDKTVERKCCVECPPCPAPPVAGPSVFLFPPKP
KDTLMISRTPEVTCVVVDVSHEDPEVQFNWYVDGVEVHNAKTKPREEQFNSTFRVVSVLTVVH

```
QDWLNGKEYKCKVSNKGLPAPIEKTISKTKGQPREPQVYTLPPSREEMTKNQVSLTCLVKGFY
PSDIAVEWESNGQPENNYKTTPPMLDSDGSFFLYSKLTVDKSRWQQGNVFSCSVMHEALHNH
YTQKSLSLSPGK

SEQ ID NO: 51-Amino acid sequence of a HC of a human antibody that binds GCGR
QVQLVESGGGVVQPGRSLRLSCAASGFTFSSYGMHWVRQAPGKGLEWVAVMWYD
GSNKDYVDSVKGRFTISRDNSKNTLYLQMNRLRAEDTAVYYCAREKDHYDILTGYN
YYYGLDVWGQGTTVTVSSASTKGPSVFPLAPCSRSTSESTAALGCLVKDYFPEPVTVSWN
SGALTSGVHTFPAVLQSSGLYSLSSVVTVPSSNFGTQTYTCNVDHKPSNTKVDKTVERKCCVE
CPPCPAPPVAGPSVFLFPPKPKDTLMISRTPEVTCVVVDVSHEDPEVQFNWYVDGVEVHNAKT
KPREEQFNSTFRVVSVLTVVHQDWLNGKEYKCKVSNKGLPAPIEKTISKTKGQPREPQVYTLP
PSREEMTKNQVSLTCLVKGFYPSDIAVEWESNGQPENNYKTTPPMLDSDGSFFLYSKLTVDKS
RWQQGNVFSCSVMHEALHNYTQKSLSLSPGK SEQ ID NO: 52-Amino acid sequence of a LC of a human antibody that binds GCGR
DIQMTQSPSSLSASVGDRVTITCRASQGIRNDLGWYQQKPGKAPKRLIYAASSLQSGV
PSRFSGSGSGTEFTLTISSVQPEDFVTYYCLQHNSNPLTFGGGTKVEIKRTVAAPSVFIF
PPSDEQLKSGTASVVCLLNNFYPREAKVQWKVDNALQSGNSQESVTEQDSKDSTYSLSSTLTL
SKADYEKHKVYACEVTHQGLSSPVTKSFNRGEC
```

What is claimed is:

1. A method for treating nonalcoholic steatohepatitis (NASH) in a subject comprising administering to a subject diagnosed with NASH a therapeutically effective amount of an isolated fully human antibody that specifically binds to the human glucagon receptor and which comprises the amino acid sequence encoding the heavy chain of SEQ ID NO: 51 and the amino acid sequence encoding the light chain of SEQ ID NO: 52.

2. A method according to claim 1, wherein the therapeutically effective amount of the isolated antagonistic antigen binding protein is selected from the group consisting of 0.001 to 100 mg/kg, 0.001 to 90 mg/kg, 0.001 to 80 mg/kg, 0.001 to 70 mg/kg, 0.001 to 60 mg/kg, 0.001 to 50 mg/kg, 0.001 to 40 mg/kg, 0.001 to 30 mg/kg, 0.001 to 20 mg/kg, 0.001 to 10 mg/kg, 0.001 to 5 mg/kg, 0.001 to 4 mg/kg, 0.001 to 3 mg/kg, 0.001 to 2 mg/kg, and 0.001 to 1 mg/kg body weight per week.

3. A method according to claim 2, wherein the therapeutically effective amount of the isolated antagonistic antigen binding protein is 0.01 to 10 mg/kg body weight per week.

4. A method according to claim 1, said method further comprising administering an anti-obesity agent to said subject, wherein the anti-obesity agent is selected from gut-selective microsomal triglyceride transport protein (MTP) inhibitors, Cholecystokinin-A (CCKa) agonists, serotonin 5HT2c agonists, melanocortin 4 receptor (MCR4) agonists, lipase inhibitors, opioid antagonists, oleoyl-estrone, obinepitide, pramlintide (SYMLIN®), tesofensine, leptin, bromocriptine, orlistat, Advanced Obesity Drug-9604 (AOD-9604), and sibutramine.

5. A method for treating nonalcoholic fatty liver disease (NAFLD) in a subject comprising administering to a subject diagnosed with NAFLD a therapeutically effective amount of an isolated fully human antibody that specifically binds to the human glucagon receptor and which comprises the amino acid sequence encoding the heavy chain of SEQ ID NO: 51 and the amino acid sequence encoding the light chain of SEQ ID NO: 52.

6. A method according to claim 5, said method further comprising administering an anti-obesity agent to said subject, wherein the anti-obesity agent is selected from gut-selective MTP inhibitors, CCKa agonists, serotonin 5HT2c agonists, MCR4 agonists, lipase inhibitors, opioid antagonists, oleoyl-estrone, obinepitide, pramlintide (SYMLIN®), tesofensine, leptin, bromocriptine, orlistat, AOD-9604, and sibutramine.

7. A method of treating a subject classified as obese (e.g., having a body mass index (BMI) of 30 kg/m² or more) comprising administering to the subject a therapeutically effective amount of an isolated fully human antibody that specifically binds to the human glucagon receptor and which comprises the amino acid sequence encoding the heavy chain of SEQ ID NO: 51 and the amino acid sequence encoding the light chain of SEQ ID NO: 52.

8. A method according to claim 7, said method further comprising administering an anti-obesity agent to said subject, wherein the anti-obesity agent is selected from gut-selective MTP inhibitors, CCKa agonists, serotonin 5HT2c agonists, MCR4 agonists, lipase inhibitors, opioid antagonists, oleoyl-estrone, obinepitide, pramlintide (SYMLIN®), tesofensine, leptin, bromocriptine, orlistat, AOD-9604, and sibutramine.

* * * * *